(12) United States Patent
Muller et al.

(10) Patent No.: US 8,557,991 B2
(45) Date of Patent: Oct. 15, 2013

(54) PROCESS FOR PREPARING ENANTIOMERICALLY PURE INDOLOPYRIDINES

(75) Inventors: Bernd Muller, Constance (DE); Helmut Schlemper, Radolfzell (DE)

(73) Assignee: 4SC AG, Planegg-Martinsried (DE)

( * ) Notice: Subject to any disclaimer, the term of this patent is extended or adjusted under 35 U.S.C. 154(b) by 277 days.

(21) Appl. No.: 12/920,990

(22) PCT Filed: Mar. 5, 2009

(86) PCT No.: PCT/EP2009/052599
§ 371 (c)(1),
(2), (4) Date: Nov. 30, 2010

(87) PCT Pub. No.: WO2009/109620
PCT Pub. Date: Sep. 11, 2009

(65) Prior Publication Data
US 2011/0077404 A1 Mar. 31, 2011

(30) Foreign Application Priority Data
Mar. 5, 2008 (EP) .................................... 08004055

(51) Int. Cl.
*C07D 471/14* (2006.01)
*C07D 471/04* (2006.01)

(52) U.S. Cl.
USPC ............................................. 546/64; 546/85

(58) Field of Classification Search
USPC ...................................................... 546/64, 85
See application file for complete search history.

(56) References Cited

U.S. PATENT DOCUMENTS 6,143,757 A    11/2000    Daugan et al.

FOREIGN PATENT DOCUMENTS

WO    WO 2007/096393 A1    8/2007

OTHER PUBLICATIONS

International Search Report of PCT/EP2009/052599 (Jun. 2, 2009).
A. Daugan et al., "The Discovery of Tadalafil: A Novel and Highly Selective PDE5 Inhibitor. 1: 5,6,11,11a-Tetrahydro-1H-Imidazo[1',5':1,6]pyrido[3,4-b]indole-1,3(2H)-dione Analogues," J. Med. Chem., vol. 46 (2003) pp. 4525-4532.
M. F. Brana et al., "One-Pot Synthesis of a 2-Dialkylaminoalkyl-Substituted Tetrahydro-β-Carboline-Hydantoin System," Liebigs Ann. Chem., No. 8 (1992) pp. 867-869.
P. Miguel et al., "Synthesis of New Derivatives of β-Carboline-Hydantoin," J. Heterocyclic Chem., vol. 27 (1990) pp. 703-706.
P. Miguel et al., "Synthesis of Tetrahydroimidazo[1,5-b]-β-carboline Derivatives with Complex Basic Substituents," J. Heterocyclic Chem., vol. 31 (1994) pp. 1235-1239.
N. Sunder-Plassmann et al., "Synthesis and Biological Evaluation of New Tetrahydro-β-Carbolines as Inhibitors of the Mitotic Kinesin Eg5," Bioorganic & Medicinal Chemistry, vol. 13 (2005) pp. 6094-6111.

*Primary Examiner* — Charanjit Aulakh
(74) *Attorney, Agent, or Firm* — Millen, White, Zelano & Branigan, P.C.

(57) ABSTRACT

Disclosed is a novel process for the preparation of pharmacologically interesting indolopyridine derivatives containing tetracyclic tetrahydro-11-carboline-hydantoines linked to a basic side chain and the corresponding salts, which can be used as Eg5 inhibitors, with very high overall chemical yield and enantiomeric purity.

20 Claims, No Drawings

PROCESS FOR PREPARING ENANTIOMERICALLY PURE INDOLOPYRIDINES

FIELD OF APPLICATION OF THE INVENTION

The invention relates to a novel process for the preparation of pharmacologically interesting indolopyridine derivatives containing tetracyclic tetrahydro-β-carboline-hydantoines linked to a basic side chain and the corresponding salts, which can be used as Eg5 inhibitor, with very high overall chemical yield and enantiomeric purity.

KNOWN TECHNICAL BACKGROUND

International patent application WO 2007/096393 A1 (Applicant: Nycomed) describes the preparation of racemic tetrahydro-β-carboline-hydantoines linked to a basic side chain by hydantoine-annulation of Pictet-Spengler β-carboline with (among others) haloethyl-isocyanate, with subsequent amination reaction of the haloethyl-sidechain. The halooethyl-isocyanates (Hal=Br, Cl, I) are applied as bifunctional reagents, to act both as building block in the heterocyclization step, leading to the hydantoine-moiety and as a linker to a broad range of different residues added to the tetrahydro-indolopyridine-core structure. This concept allows to effectively set up a compound library with broad diversity.

U.S. Pat. No. 6,143,757A (Applicant: ICOS Corp.) describes the preparation of cis- and trans-fused tetrahydro-1H-imidazo[1',5":1,6]pyrido[3,4-b]indole-1,3(2H)-dione analogues as a novel class of highly potent and selective PDE5 inhibitors. The heterocyclization to the hydantoine unit is achieved with carbonyldiimidazole-activation of primary amines, including N,N-dimethyl-ethane-1,2-diamine.

A. Daugan et al., J. Med. Chem., 2003, Vol. 46, 4525-32, also describes the procedure of U.S. Pat. No. 6,143,757A for reaction of trans-substituted racemic β-carbolines, obtaining the 2-(dimethylamino)ethyl-derivative in 64.5% after crystallization.

M. F. Brana et al., Lieb. Ann. Chemie, 1992, 867-869, describes a "one-pot synthesis of a 2-dialkylaminoalkyl-substituted tetrahydro-β-carboline-hydantoine system", "as a new and convenient method for the synthesis of pharmacologically interesting compounds containing the tetrahydro-β-carboline-hydantoin moiety linked to a basic chain." Various diamino substituted alkyl-spacers, including N,N-dimethyl-1,2-diamino-ethane were treated with carbonyldiimidazole prior to the annulation step. Annulation products were obtained in moderate yields (38-50%) as racemic mixtures.

Sunder-Plassmann et al., Bioorg. Med. Chem. 13 (22), 2005, 6094-6111 describes "Synthesis and Biological evaluation of new tetrahydro-β-carbolines as inhibitors of the mitotic kinesin Eg5", starting from 1-(3-hydroxyphenyl)-carboline-3-carboxylic acids and various alkyl-isocyanate-building blocks.

None of the processes cited above appear to be suitable for the industrial large scale preparation of enantiomerically pure (stereomerically pure) tetracyclic tetrahydro-β-carboline-hydantoines linked to a basic chain with the required overall efficiency.

As described above, prior art processes for hetero-annulation reactions building up a hydantoine ring with a basic side chain, is only available for racemic β-carboline compounds missing the alkyl-substitution in 3-position (i.e. with reduced sterical hindrance at the β-carboline framework) and with insufficient chemical yield. The two-step approach with haloethyl-isocyanate-coupling followed by halogen-amine-substitution, described in WO2007/096393 needs the search for an alternative process due to the critical toxicity of haloethylisocyanates, namely bromo- or chloroethylisocyanate, together with the additional work-demand for the twostep procedure. Besides that, there are difficulties in driving the annulation reactions to sufficient yields above ca. 50%, not to forget additional problems during the amination step, which is hampered by the very low solubility of produced haloethyl-hydantoine plus safety and ecology issues running the process with low boiling dimethylamine in a pressurized reactor.

DESCRIPTION OF THE INVENTION

It has now been found that tetracyclic tetrahydro-β-carboline-hydantoines linked to a basic side chain can be prepared in high yield and with a high enantiomeric purity in the process described as follows.

The inventive process starts with enantiomerically pure (stereomerically pure) tryptophane derivatives and avoids an amination step by using carbonyldiimidazole derivatized amino compounds. (see advantage of the inventive process below)

The invention thus relates in a first aspect to a process for the preparation of compounds of formula I

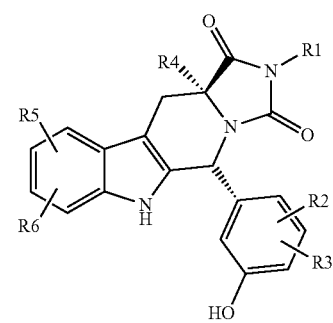

in which
R1 is 2-7C-alkyl substituted by —N(R111)R112, in which
R111 is 1-4C-alkyl, 2-4C-alkenyl, 2-4C-alkenyl, 3-7C-cycloalkyl, 3-7C-cycloalkyl-1-4C-alkyl, hydroxy-2-4C-alkyl, 1-4C-alkoxy-2-4C-alkyl, 1N-(1-4C-alkyl)-pyrazolyl, 1N—(H)-pyrazolyl, isoxazolyl, or completely or partially fluorine-substituted 1-4C-alkyl,
R112 is hydrogen, 1-4C-alkyl, 3-7C-cycloalkyl, or 3-7C-cycloalkyl-1-4C-alkyl,
or R111 and R112 together and with inclusion of the nitrogen atom, to which they are bonded, form a ring Het, in which
Het is piperidin-1-yl, morpholin-4-yl, thiomorpholin-4-yl, S-oxo-thiomorpholin-4-yl, S,S-dioxo-thiomorpholin-4-yl, pyrrolidin-1-yl, azetidin-1-yl, homopiperidin-1-yl, 4N—(R113)-piperazin-1-yl, 4N—(R113)-homopiperazin-1-yl, 2,5-dihydro-pyrrol-1-yl, 1,2,3,6-tetra-hydropyridin-1-yl, pyrrol-1-yl, pyrazol-1-yl, imidazol-1-yl, triazol-1-yl, or tetrazol-1-yl, in which
R113 is hydrogen, 1-4C-alkyl, 3-7C-cycloalkyl, 3-7C-cycloalkyl-1-4C-alkyl, 1-4C-alkylcarbonyl, amidino, or completely or partially fluorine-substituted 1-4C-alkyl,
wherein said Het may be optionally substituted by one or two substituents independently selected from fluorine and 1-4C-alkyl,
R2 is hydrogen, 1-4C-alkyl, halogen, trifluoromethyl, 1-4C-alkoxy or hydroxyl, R3 is hydrogen, 1-4C-alkyl, halogen, trifluoromethyl or 1-4C-alkoxy, R4 is 1-4C-alkyl, 3-7C-cycloalkyl or 3-7C-cycloalkyl-1-4C-alkyl, R5 is 1-4C-alkyl, halogen, 1-4C-alkoxy, trifluoromethyl, cyano, hydroxyl, phenyl-1-4C-alkoxy, 1-4C-alkoxy-2-4C-alkoxy, hydroxy-2-4C-alkoxy, 3-7C-cycloalkoxy, 3-7C-cycloalkyl-1-4C-alkoxy, or completely or predominantly fluorine-substituted 1-4C-alkoxy, R6 is hydrogen, 1-4C-alkyl or halogen, and the salts of these compounds, which process comprises the steps of a) providing an enantiomerically pure (stereomerically pure) tryptophane derivative of formula IVa,

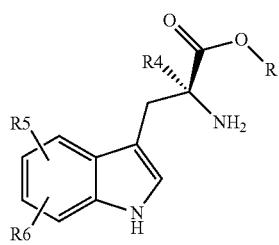

IVa wherein R is methyl or ethyl and R4, R5, R6 are as defined above, b) Pictet Spengler Reaction of the compounds of formula IVa with 3-hydroxybenzaldehyde of formula III,

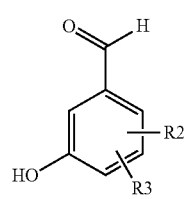

III wherein R2, R3 are as defined above, to obtain a mixture of compounds of formulae IIa and IIb,

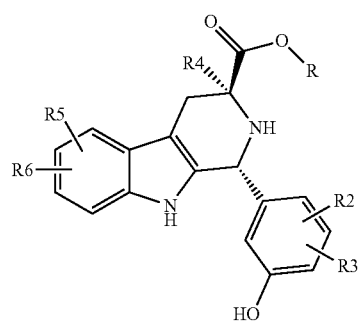

IIa

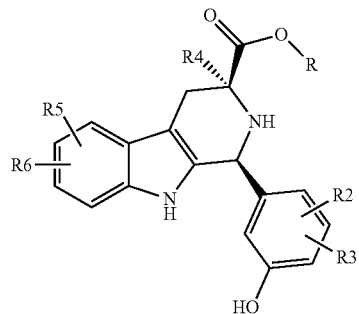

IIb wherein R, R2, R3, R4, R5, R6 are as defined above, separation of the compounds of formulae IIa and IIb to obtain compounds of formula IIa, c) optional protection of the compounds of formula IIa at the 3-hydroxyphenyl moiety to obtain compounds of formula IIa*

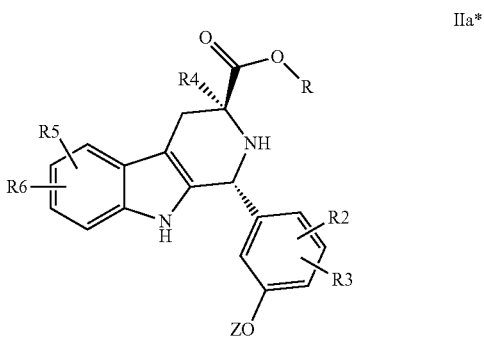

IIa* wherein R, R2, R3, R4, R5, R6 are as defined above and Z is a protective group, d) heterocyclization of the compounds of formula IIa* or the compounds of formula IIa by means of in situ prepared isocyanate R1-N=C=O by adding a reaction mixture of carbonyldiimidazole and an amine R1NH2 in a solvent to obtain compounds of formula Ia,

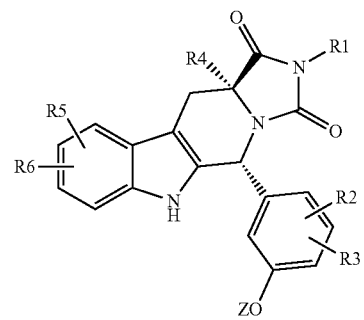

Ia wherein R1-R6 and Z are as defined above, or to obtain the compounds of formula I, e) deprotection at the 3-hydroxyphenyl moiety of compounds of formula Ia to obtain the compounds of formula I, provided that compounds of the formula IIa have been protected at the 3-hydroxyphenyl moiety in step c), f) optional conversion of the compounds of formula I into salts.

The process is described in detail as follows:

The Starting Material Compound IVa (Step a)

Enantiomerically pure (stereomerically pure) starting compounds IVa may be obtained according to art-known processes, such as e.g. from the corresponding racemates (compounds of formula IV as shown in reaction scheme 1 below) for example, by means of salt formation of the racemic compounds with optically active acids, preferably carboxylic acids (examples of optically active acids which may be mentioned in this connection are the enantiomeric forms of mandelic acid, tartaric acid, O,O'-dibenzoyltartaric acid, camphoric acid, quinic acid, glutamic acid, pyroglutamic acid, malic acid, camphorsulfonic acid, 3-bromocamphorsulfonic acid, α-methoxyphenylacetic acid, α-methoxy-α-trifluoromethylphenylacetic acid and 2-phenylpropionic acid), subsequent resolution of the salts [e.g. by (fractional) crystallization from a suitable solvent] and release of the desired compound from the salt; by kinetic resolution of the racemic compounds, such as by enzymatic racemate resolution, e.g. during enzymatic saponification of the corresponding racemic amino acid esters using e.g. a suitable lipase (such as e.g. in analogy to the procedure described by Houng et al. Chirality 1996, 8, 418-422); or by stereoselective amino acid synthesis, e.g. using an appropriate chiral auxiliary; or by chromatographic separation of racemic compounds on chiral separating columns. Thus, enantiomerically pure tryptophans may be obtained, for example, as described in Tetrahedron Letters 39 (1998), 9589-9592, or analogously or similarly thereto, such as e.g. enantiomerically pure α-methyl-tryptophans, α-ethyl-tryptophans or α-isopropyl-tryptophans may be obtained as described therein starting from N-Boc-(3-bromomethyl)-indole and enantiomerically pure alanine, 2-amino-butyric acid or valine, respectively.

Enantiomerically pure 5-methoxy-α-methyl-tryptophane methyl ester can be obtained by chromatographic separation of the corresponding racemate on chiral separating columns, such as e.g. Daicel CHIRALPAK AD-RH or Daicel CHIRALPAK AD-H; or by means of salt formation of the corresponding racemate with optically active acids, such as e.g. mandelic acid, pyroglutamic acid or, particularly, (S,S)-di-p-anisoyl-tartaric acid, subsequent resolution of the salt [e.g. by (fractional) crystallization from a suitable solvent, such as e.g. ethyl acetate or acetone] and release of the desired compound from the salt.

Compounds of formula IV, in which R is methyl or ethyl, and R4, R5 and R6 have the meanings given above, are accessible as shown in Reaction scheme 1, and as described in WO2007/096393.

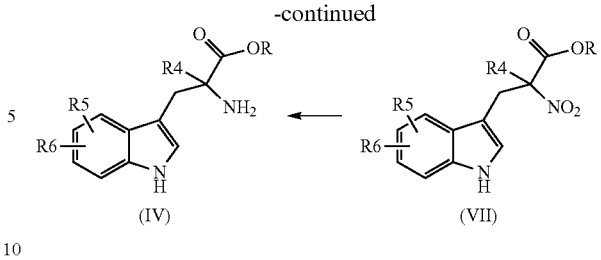

Starting from compounds of formula X, in which R5 and R6 have the meanings mentioned above, the corresponding compounds of formula VIII can be obtained by aminomethylation reaction (Mannich reaction) customary known per se to the person skilled in the art.

Compounds of formula VIII are reacted with compounds of formula IX, in which R is methyl or ethyl and R4 has the meanings given above, in a nucleophilic substitution reaction to give corresponding compounds of formula VII. Said substitution reaction can be carried out as it is known for the skilled person or as described in the following examples, or analogously or similarly thereto.

Compounds of formula VII are subjected to a reduction reaction of the nitro group to obtain corresponding amine compounds of formula VI. Said reduction reaction can be carried out as habitual per se to the skilled person, such as, for example, by catalytic hydrogenation, e.g. in the presence of a noble metal catalyst such as palladium on active carbon or, particularly, Raney nickel. Optionally, a catalytic amount of an acid, such as, for example, hydrochloric acid, can be added to the solvent. Alternatively, the reduction may be carried out using a hydrogen-producing mixture, for example, metals such as zinc, zinc-copper couple or iron with organic acids such as acetic acid or mineral acids such as hydrochloric acid.

The hydrogenation of VII can be connected with the optical resolution step described below.

Optionally, ester compounds of formula VI can be converted into the corresponding free acids by art-known saponification reaction. Optionally, the free acids of compounds of formula VI can be also re-converted into the corresponding esters, particularly methyl esters, by art-known esterification reaction, e.g. using thionylchloride/methanol.

Compounds of formula IX are known, commercially available (such as e.g. ethyl 2-nitro-propionate or ethyl 2-nitro-butyrate) or can be obtained according to known procedures.

Methyl 2-nitro-propionate is known e.g. from H. L. Finkbeiner, G. W. Wagner J. Org. Chem. 1963, 28, 215-217).

In more detail, compounds of formula IX, in which R is methyl or ethyl and R4 has the meanings given above, can be obtained as outlined in reaction scheme 2.

Reaction scheme 1

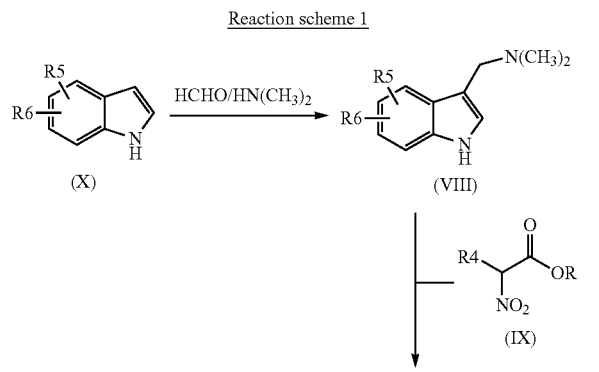

Reaction scheme 2:

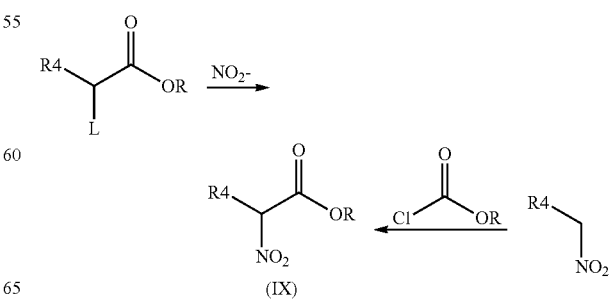

Compounds of formula IX can be prepared by reaction of compounds of formula R4-CH$_2$—NO$_2$, in which R4 has the meanings given above, e.g. cyclopropyl, with a chloroformic acid ester, such as e.g. described in Ram et al. Synthesis 1986, 133-135, or analogously or similarly thereto.

Alternatively, compounds of formula IX can be prepared by reaction of compounds of formula R4-C(H)L-CO$_2$R, in which L is a suitable leaving group, e.g. iodine, and R4 has the meanings given above, e.g. isopropyl, with a suitable nitrite reagent, e.g. sodium nitrite or silver nitrite, such as e.g. described in J. Am. Chem. Soc. 77, 6654 (1955), or analogously or similarly thereto.

Compounds of formula R4-CH$_2$—NO$_2$ and R4-C(H)L-CO$_2$R are known or can be obtained analogously or similarly to known procedures (e.g. compounds of formula R4-C(H)L-CO$_2$R can be obtained via Finkelstein reaction); such as e.g. nitromethyl-cyclopropane can be obtained as described in Helv. Chim. Acta 1982, 65, 137-161 and 2-iodo-3-methyl-butyric acid ethyl ester can be obtained from 2-bromo-3-methyl-butyric acid ethyl ester as described in Org. Lett. 1999, 1, 1419-1422, or analogously or similarly thereto.

Compounds of formula X are known or can be obtained according to known procedures or as described in the following examples or analogously or similarly thereto.

Thus, e.g. 5-methoxy-1H-indole, 5-chloro-1H-indole, 5-bromo-1H-indole, 5-fluoro-1H-indole and 5-trifluoromethyl-1H-indole are commercially available.

Compounds of formula X, which are ether compounds, are obtained from the corresponding alcohol compounds by art-known etherification reaction. Thus, e.g. compounds of formula X, in which R5 is hydroxyl, can be converted into corresponding ether compounds in a manner as described in the following examples, or analogously or similarly thereto.

Thus, e.g. compounds of formula X, in which R5 is hydroxyl, can be converted into the corresponding compounds of formula X, in which R5 is ethoxy, propoxy, isopropoxy, cyclopropylmethoxy, difluoromethoxy or trifluoromethoxy, by alkylating reaction using an appropriate alkylating reagent.

Preferably the enantiomerically pure (stereomerically pure) tryptophane derivative of the formula IVa is provided by optical resolution of a racemic tryptophane-ester of formula IV,

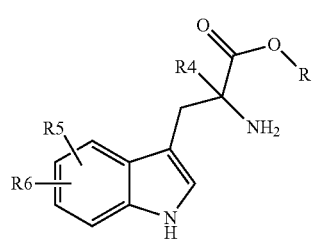

IV wherein R is methyl or ethyl and R4, R5 and R6 are as defined above,
by salt formation with optically active acids and subsequent resolution of the salt by crystallization from a solvent system to obtain an enantiomerically pure (stereomerically pure) tryptophane derivative salts of formula IVa*,

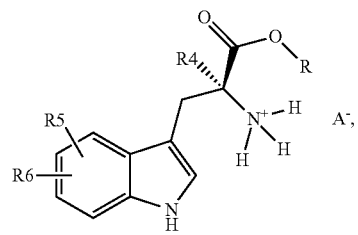

IVa* wherein R, R4, R5 and R6 are as defined above and A is the anion derived from the optically active acid, and
subsequent liberation of compounds of formula IVa,

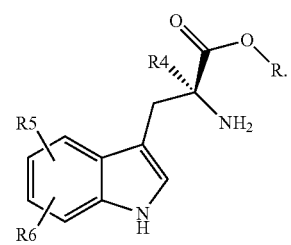

IVa

Thus a particular preferred process of the present invention for the preparation of compounds of formula I comprises the steps of
a) optical resolution of a racemic tryptophane-ester of formula IV,

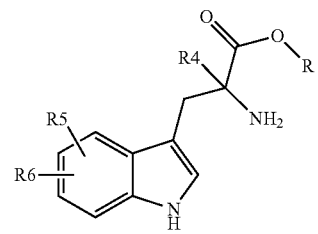

IV wherein R is methyl or ethyl and R4, R5 and R6 are as defined above,
by salt formation with optically active acids and subsequent resolution of the salt by crystallization from a solvent system to obtain an enantiomerically pure (stereomerically pure) tryptophane derivative salts of formula IVa*,

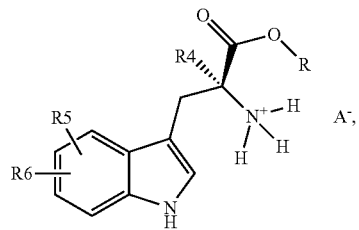

IVa* wherein R, R4, R5 and R6 are as defined above and A is the anion derived from the optically active acid, and subsequent liberation of compounds of formula IVa,

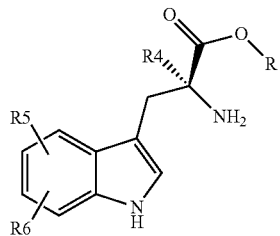

b) Pictet Spengler Reaction of the compounds of formula IVa with 3-hydroxybenzaldehyde of formula III,

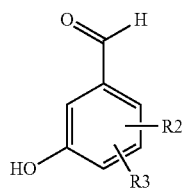

wherein R2, R3 are as defined above, to obtain a mixture of compounds of formulae IIa and IIb,

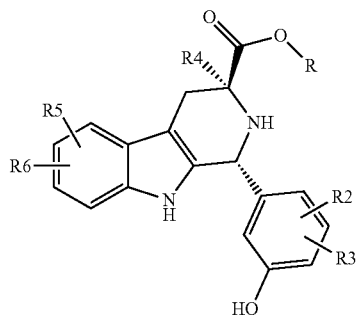

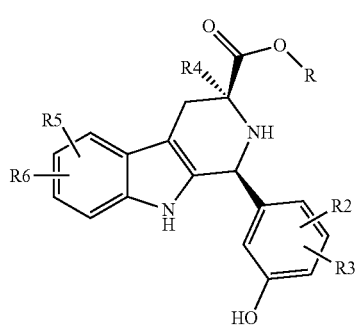

wherein R, R2, R3, R4, R5, R6 are as defined above,
separation of the compounds of formulae IIa and IIb to obtain compounds of formula IIa, c) optional protection of the compounds of formula IIa at the 3-hydroxyphenyl moiety to obtain compounds of formula IIa*,

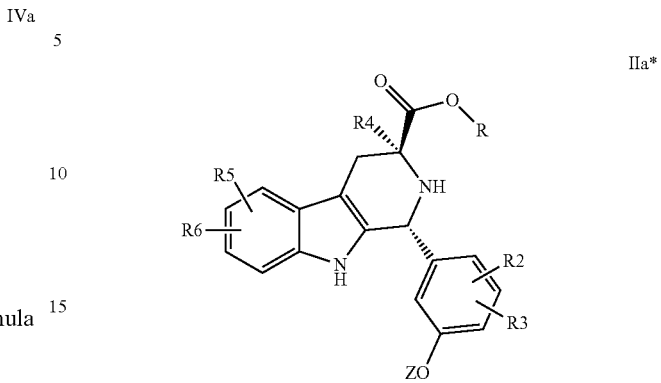

wherein R, R2, R3, R4, R5, R6 are as defined above and Z is a protective group, d) heterocyclization of the compounds of formula IIa* or the compounds of formula IIa by means of in situ prepared isocyanate R1-N=C=O by adding a reaction mixture of carbonyldiimidazole and an amine R1NH2 in a solvent to obtain compounds of formula Ia,

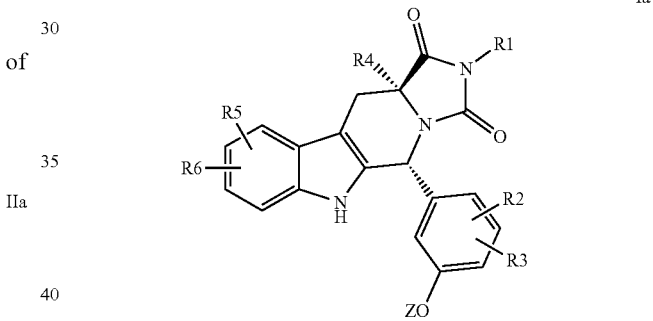

wherein R1-R6 and Z are as defined above, or to obtain the compounds of formula I, e) deprotection at the 3-hydroxyphenyl moiety of compounds of formula Ia to obtain the compounds of formula I, provided that compounds of the formula IIa have been protected at the 3-hydroxyphenyl moiety in step c), f) optional conversion of the compounds of formula I into salts.

As optically active acids, preferably carboxylic acids selected from the enantiomeric forms of mandelic acid, tartaric acid, O,O'-dibenzoyltartaric acid, Di(p-anisoyl)tartaric acid), camphoric acid, quinic acid, glutamic acid, pyroglutamic acid, malic acid, camphorsulfonic acid, 3-bromocamphorsulfonic acid, α-methoxyphenylacetic acid, α-methoxy-α-trifluoro-methylphenylacetic acid and 2-phenylpropionic acid) can be used. More preferably enantiomeric forms of tartaric acid, O,O'-dibenzoyltartaric acid, or Di(p-anisoyl)tartaric acid such as (2S,3S)-(+)-Di(p-anisoyl) tartaric acid are used, most preferably (2S,3S)-(+)-Di(p-anisoyl)tartaric acid (Synonym: (S,S)-Di-p-anisoyltartaric acid) or D-DATA) is used.

Especially Successful Resolution of Racemic Compounds IV

Most preferably the enantiomerically pure (stereomerically pure) tryptophane derivative of the formula IVa is provided by a method of separating the enantiomerically pure compound of formula IVa from a racemic mixture of compounds IV the method comprising: treating the racemic mixture of compounds IV with (2S,3S)-(+)-Di(p-anisoyl)tartaric acid to separate the desired enantiomer from the racemic mixture. By using (2S,3S)-(+)-Di(p-anisoyl)tartaric acid, enantiomers with very good optical purity could be obtained in very good yields.

To prepare compounds IVa, the racemic compounds IV are treated with D-DATA in a solvent at room temperature or slightly warmed up within a range of room temperature up to 70° C. and the resulting diastereomeric salt is allowed to crystallize slowly at room temperature. Suitable solvents are alcohols, such as methanol, ethanol, propanol, 2-propanol, esters such as ethylacetate, 2-propylacetate and mixtures thereof. Preferred solvents are mixtures such as ethanol/toluene or ethanol/2-propylacetate, particularly preferred is a mixture of ethanol/2-propylacetate.

The pure crystallized salts are then treated with a basic solution, usually at room temperature, to generate the free desired enantiomer. Suitable basic solutions are aqueous basic solutions such as aqueous ammonia solutions or aqueous NaOH solutions. Preferred basic solutions are aqueous ammonia solutions.

The optical purity of compound IVa obtained by this method is greater 96% ee by chiral HPLC.

The optical resolution is thus most preferably carried out according to reaction scheme 3

Reaction scheme 3

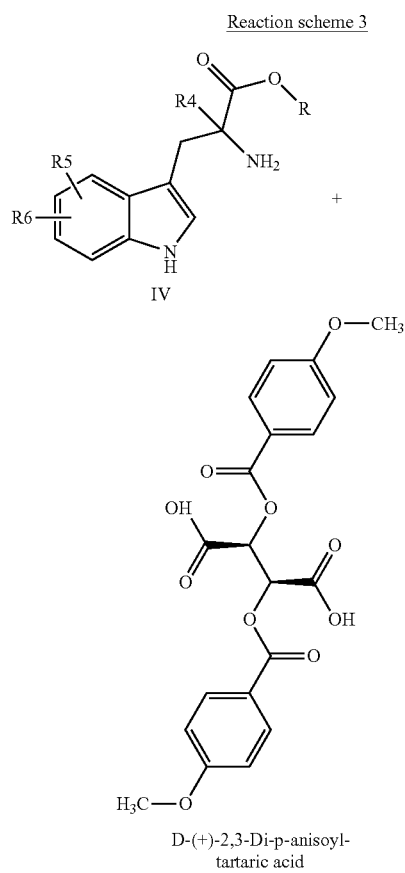

D-(+)-2,3-Di-p-anisoyl-tartaric acid

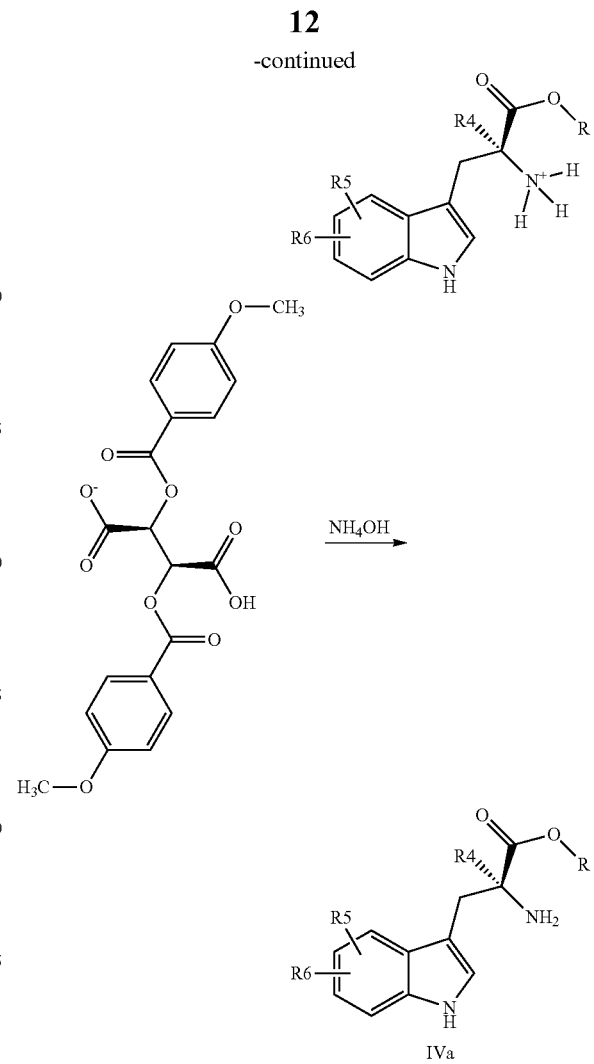

As mentioned above it is possible to connect the hydrogenation of compound VII of Scheme 1 to the optical resolution step according to reaction scheme 3a.

Reaction scheme 3a

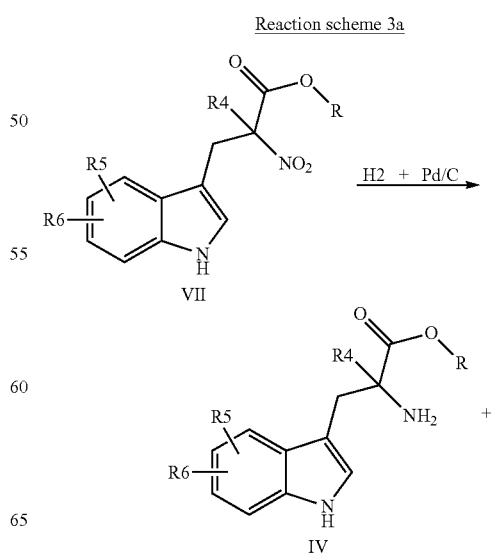

13

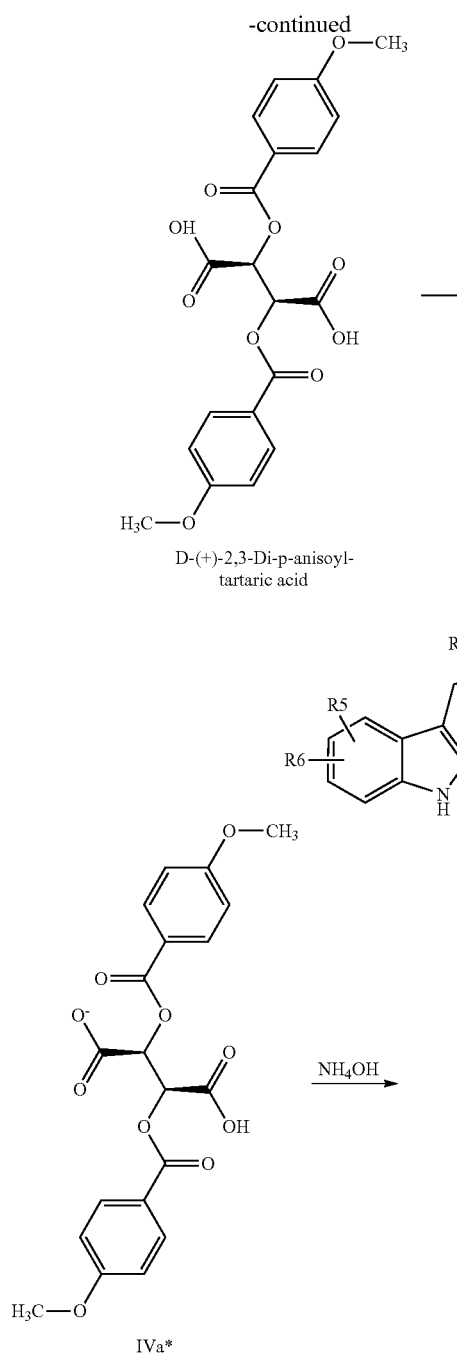

D-(+)-2,3-Di-p-anisoyl-
tartaric acid

Step b): Pictet Spengler Cyclisation Starting from Enantiomerically Pure Trypthophan Derivatives or from its Salts.

As shown in the synthesis route outlined in scheme 4 below, enantiomerically pure ester compounds of formula IVa (particularly, the ethyl esters or, especially, methyl esters of formula IVa), in which R, R4, R5 and R6 have the meanings given above, are condensed and cyclized in a Pictet-Spengler reaction with benzaldehydes of formula III, in which R2 and R3 have the meanings mentioned above, to give the corresponding compounds of formulae IIa and/or IIb, mostly as a mixture.

It is also possible to connect the liberation of the optical pure tryptophane derivative from its salt (IVa* to IVa) with the subsequent Pictet Spengler Reaction by simply changing the solvent.

Said Pictet-Spengler reaction can be carried out as it is known to the skilled person or as described in the following examples, advantageously in the presence of a suitable acid as a catalyst or promotor (e.g. trifluoroacetic acid) in a suitable solvent, for example dichloromethane or, particularly toluene, at room temperature or elevated temperature.

Compounds of formula III are known or can be obtained in a known manner, for example by formylation of appropriate aromatic compounds, e.g. via hydroxymethylation and subsequent oxidation to the aldehyde, or by reduction of appropriate benzoic acid derivatives to the aldehyde.

Reaction scheme 4:

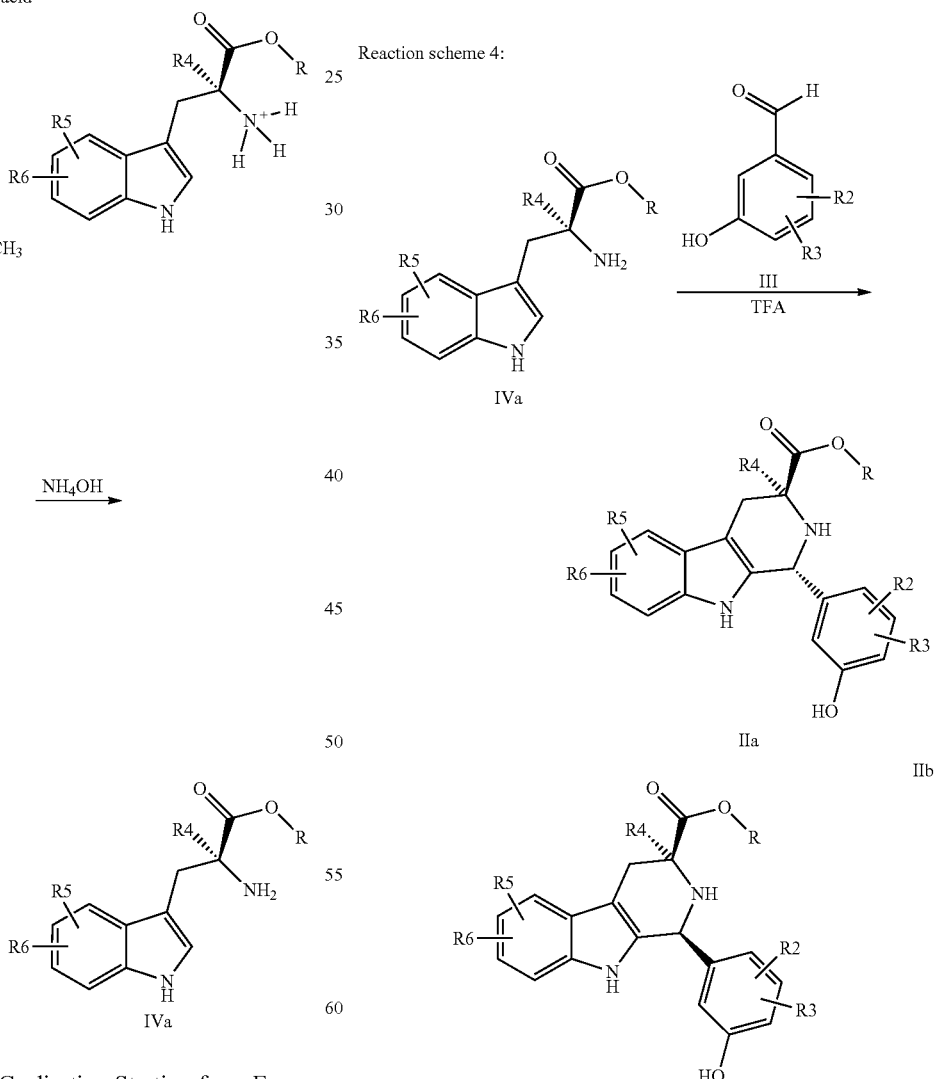

To obtain the compounds of formula IIa in high yield and purity, the diastereomers of formula IIa and IIb can be separated by methods known to the person skilled in the art like phase separation, which is the preferred method. Phase separation is usually performed by adding a further solvent to the obtained Pictet-Spengler-products, in which the desired disastereomer is insoluble and the undesired diastereomer is soluble. Suitable solvents are esters such as ethyl acetate, toluene, xylene and dichloromethane. A preferred solvent is toluene.

The yield of the desired disastereomer can be increased by repeated isomerization of the undesired diastereomer by e.g. heating the undesired diastereomer in a solvent like toluene in the presence of trifluoroacetic acid as catalyst at elevated temperatures.

Step c) Optional Protection of Compound IIa at the 3-hydroxyphenyl Moiety to Protect the Free Hydroxy Group Protection of compounds of formula IIa at the 3-hydroxyphenyl moiety to obtain compound IIa*:

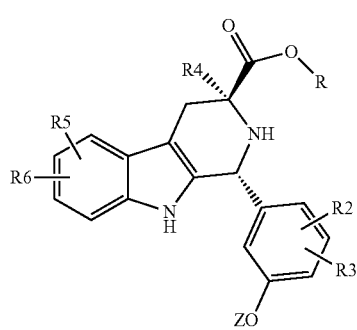

IIa* can be achieved by protecting said hydroxy group using protective groups known to the skilled person such as a variety of common silylating agents, or by adding an acetyl, trifluoracetyl, benzyl or trityl group to the hydroxy group. Preferably any of a variety of common silylating agents including, but not limited to, tri(alkyl)silyl halides are used. More preferably tri(alkyl)silyl halides, most preferably trimethylsilyl chloride are used.

Suitable solvents for the selective silylation reaction are ethereal solvents such as tetrahydrofuran (THF), 2-methyl-THF, or toluene, acetonitrile, propionitrile, or mixtures thereof. Preferably toluene or mixtures thereof such as toluene/acetonitrile or toluene/THF are used. The reaction is usually carried out at elevated temperature in a range of between 40-70° C.

The protection of the 3-hydroxyphenyl moiety of compound of formula IIa before building up the hydantoin ring significantly increases the overall yield and is, together with the deprotection step e) as described below, therefore preferred.

Step d) Heterocyclization of the Compounds of Formula IIa* or the Compounds of Formula IIa by Means of in situ Prepared Isocanate R1-N═C═O by Adding a Reaction Mixture of carbonyldiimidazole (CDI) and an Amine R1NH2 in a Solvent In case of the heterocyclization of the compounds of formula IIa*, the isocyanate is prepared in situ as outlined in Scheme 5 and added to the protected compounds of formula IIa* to obtain compounds of formula Ia. After deprotection at the 3-hydroxyphenyl moiety of compound Ia, compound I is obtained. In case of the heterocyclization of the compounds of formula IIa without the optional step c) the isocyanate is prepared in situ and added to the compounds of formula IIa to obtain compounds of formula I.

Reaction scheme 5

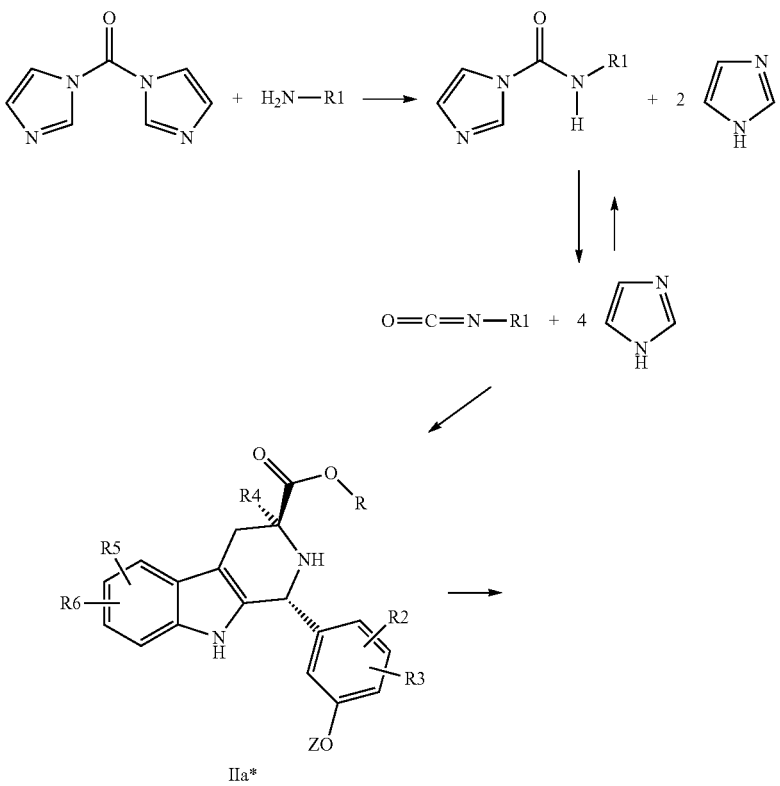

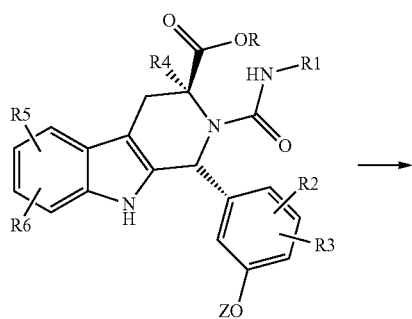
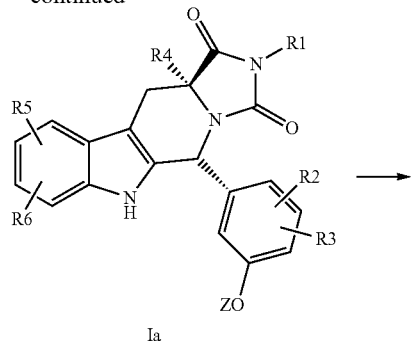

-continued

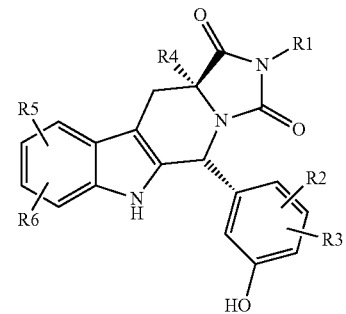

As carbonyldiimidazole (CD), carbonyldiimidazole or carbonyldiimidazole derivatives comprising substituted imidazole moieties can be used, preferably carbonyldiimidazole is used. Suitable solvents for the Hydantoin cyclisation are, for example, toluene or xylene or mixtures such as toluene/acetonitrile or toluene/benzonitrile. The reaction is carried out at a temperature range of about 60 to about 130° C. preferably at a temperature range of about 90 to about 120° C., more preferably at a temperature range of about 100 to about 105° C. Usually the dosing temperature is adapted to the optimum activation temperature of the isocyanate-precursor, which lies within the range of about 90 to about 120° C. and the dosing speed of the imidazolide is adapted to the reaction speed of the annulation step.

The above described process is preferably run in two alternative ways. In case technical grade carbonyldiimidazole with purity of around 90-95% is used, the preferred reaction-solvent is a mixture of acetonitrile/toluene, whereas the imidazolide is added to the compounds of formula IIa* or to the compounds of formula IIa within about 1 to about 4 hours and the reaction temperature is continuously increased e.g. from around 55 to around 105° C. by distilling off acetonitrile.

In case purum grade carbonyldiimidazole with purity >97% is used, the preferred reaction-solvent is pure toluene, whereas the imidazolide is added to the compounds of formula IIa* or to the compounds of formula IIa within about 5 to about 20 hours, preferably within about 8 to about 12 hours under isothermal conditions at optimum activation temperature, i.e. around 100-105° C.

It has been surprisingly found that step d) carried out as described above enables significant reduction of by-products and a distinct increase of overall yield.

Step e) Deprotection

Provided that compounds of formula IIa have been protected at the 3-hydroxyphenyl moiety in step c), a deprotection step is carried out, whereas the deprotection of the protected OH group is achieved using acid/base catalyzed hydrolysis. More preferably, the hydrolysis is achieved using aqueous HCl to obtain a pH of around 6-7. Usually the deprotection step is carried out during the aqueous work-up of step d), thereby avoiding a separate deprotection step.

This new one-pot protocol for the above described preferred heteroannulation process (steps d) and e)) combines three otherwise sequential chemical transformations, namely:

1. Protection of enantiomeric pure β-carboline at the 3 hydroxyphenyl moiety to: a) increase solubility in solvents best suited for the high temperature annulation step, b) protect the free hydroxygroup.

2. Heterocyclization of the β-carboline with a carbonyldiimidazole-derivatized building block at the appropriate reaction temperature for activation of the isocyanate-precursor, circumventing the amination step. Initial-quench conditions avoid critical handling of toxic isocyanates and reduce unfavourable side reactions of the reactive intermediate, e.g. self-condensation.

3. Mild deprotection at the 3-hydroxyphenyl moiety during work-up, followed by isolation of high purity annulation product, avoiding a separate deprotection step.

4. High yield of compound I up to about 90% having an optical purity of 99.0% ee by chiral HPLC.

In case R111 is as defined above and R112 is hydrogen in the —N(R111)R112 group of the amine R1NH2 used in step d) of the process of the invention, R111 is usually a sterically hindered group, preferably a sterically hindered alkyl-group such as isopropyl-, sec-butyl, tert.-butyl or neopentyl. Optionally bulky protecting groups can be introduced at the nitrogen of the —N(R111)H group of the amine R1NH2 in this case or, more suitably, are introduced in situ onto the carbonyldiimidazole-derivatized imidazolide-moiety built as first product after the reaction of the amine R1NH2 with carbonyldiimidazole as shown in scheme 5. Corresponding protecting groups have to show thermal and chemical stability under the desribed conditions and are selected from e.g. acetyl or trifluoracetyl.

Step f) Conversion into Salts

Optionally, compounds of the formula I can be converted into their salts, or, optionally, salts of the compounds of the formula I can be converted into the free compounds. Corresponding processes are customary for the skilled person.

When one of the final steps or purification is carried out under the presence of an inorganic or organic acid (e.g. hydrochloric, trifluoroacetic, acetic or formic acid or the like), the compounds of formula I may be obtained—depending on their individual chemical nature and the individual nature of the acid used—as free base or containing said acid in an stoechiometric or non-stoechiometric quantity. The amount of the acid contained can be determined according to art-known procedures, e.g. by titration or NMR.

Salts can be obtained by dissolving the free compound in a suitable solvent (e.g. a ketone, such as acetone, methyl ethyl ketone or methyl isobutyl ketone, an ether, such as diethyl ether, diisopropyl ether, tetrahydrofuran or dioxane, a chlorinated hydrocarbon, such as methylene chloride or chloroform, a low-molecular-weight aliphatic alcohol, such as methanol, ethanol or isopropanol, or an ester, such as ethyl acetate) which contains the desired acid or base, or to which the desired acid or base is then added. The salts can be obtained by filtering, reprecipitating, precipitating with a nonsolvent for the addition salt or by evaporating the solvent. Salts obtained can be converted into the free compounds, which can in turn be converted into salts, by alkalization or by acidification. In this manner, pharmacologically unacceptable salts can be converted into pharmacologically acceptable salts.

Suitable salts for compounds of formula I according to this invention—depending on substitution—are all acid addition salts or all salts with bases. Particular mention may be made of the pharmacologically tolerable inorganic and organic acids and bases customarily used in pharmacy. Those suitable are, on the one hand, water-insoluble and, particularly, water-soluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid such as (−)-L-malic acid or (+)-D-malic acid, fumaric acid, succinic acid, oxalic acid, tartaric acid such as (+)-L-tartaric acid or (−)-D-tartaric acid or meso-tartaric acid, embonic acid, stearic acid, toluenesulphonic acid, methanesulphonic acid or 3-hydroxy-2-naphthoic acid, the acids being employed in salt preparation—depending on whether a mono- or polybasic acid is concerned and depending on which salt is desired—in an equimolar quantitative ratio or one differing therefrom.

On the other hand, salts with bases are—depending on substitution—also suitable. As examples of salts with bases are mentioned the lithium, sodium, potassium, calcium, aluminium, magnesium, titanium, ammonium, meglumine or guanidinium salts, here, too, the bases being employed in salt preparation in an equimolar quantitative ratio or one differing therefrom.

Salts which are unsuitable for pharmaceutical uses but which can be employed, for example, for the isolation or purification of free compounds of formula I or their pharmaceutically acceptable salts, are also included.

Pharmacologically intolerable salts, which can be obtained, for example, as process products during the preparation of the compounds according to this invention on an industrial scale, are converted into pharmacologically tolerable salts by processes known to the person skilled in the art.

According to expert's knowledge the compounds of formula I according to this invention as well as their salts may contain, e.g. when isolated in crystalline form, varying amounts of solvents. Included within the scope of the invention are therefore all solvates and in particular all hydrates of the compounds of formula I according to this invention as well as all solvates and in particular all hydrates of the salts of the compounds of formula I according to this invention.

In a preferred embodiment of this invention, salts of compounds of formula I include a salt of a compound of formula I with hydrochloric acid (a hydrochloride salt). In another preferred embodiment of this invention, salts of compounds of formula I include a salt of a compound of formula I with methanesulfonic acids. Most preferably, salts of compounds of formula I include a salt of a compound of formula I with hydrochloric acid (a hydrochloride salt).

Preferences of the Process

Preferred is a process wherein the enantiomerically pure (stereomerically pure) tryptophane derivative of the formula IVa (step a)) is provided by optical resolution of a racemic tryptophane-ester of formula IV,

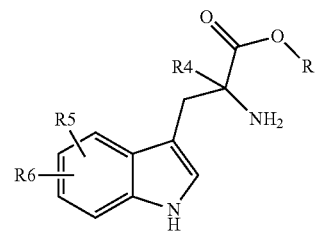

IV wherein R is methyl or ethyl and R4, R5 and R6 are as defined above, by salt formation with optically active acids and subsequent resolution of the salt by crystallization from a solvent system to obtain an enantiomerically pure (stereomerically pure) tryptophane derivative salt of formula IVa*,

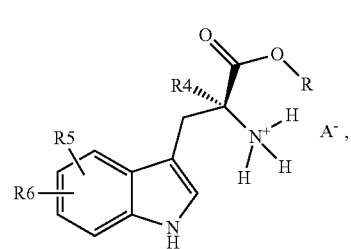

IVa* wherein R, R4, R5 and R6 are as defined above and A is the anion derived from the optically active acid, and subsequent liberation of compounds of formula IVa,

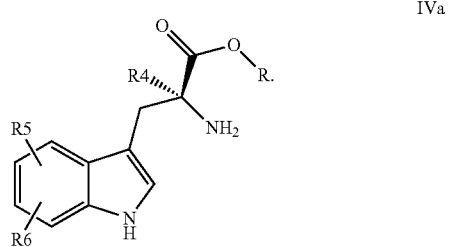

Even more preferred is a process wherein the optical resolution of the racemic tryptophane-ester of the formula IV (step a)) is achieved by salt formation with D-(2S,3S)-(+)-di-(4-methoxybenzoyl)tartaric acid.

Preferred is a process, wherein the protection step c) is carried out using tri(alkyl)silyl halides as protective group Z.

Preferred is a process, wherein the compounds of formula IIa are protected in step c) and the compounds of formula Ia are deprotected in step e).

Preferred is a process, wherein in step d) the solvent is a mixture of acetonitrile/toluene, whereas the reaction mixture of carbonyldiimidazole and the amine R1NH2 is added to the compounds of formula IIa* or to the compounds of formula IIa within about 1 to about 4 hours and the reaction temperature is continuously increased from around 55 to around 105° C. by distilling off acetonitrile or, wherein in step d) the solvent is pure toluene, whereas the reaction mixture of carbonyldiimidazole and the amine R1NH2 is added to the compounds of formula IIa* or to the compounds of formula IIa within about 5 to about 20 hours, preferably within about 8 to about 12 hours under isothermal conditions at optimum activation temperature of around 100-105° C.

Definition of the Substituents

As used herein, "alkyl" alone or as part of another group refers to both branched and straight chain saturated aliphatic hydrocarbon groups having the specified numbers of carbon atoms, such as for example:

1-4C-Alkyl is a straight-chain or branched alkyl radical having 1 to 4 carbon atoms. Examples are the butyl, isobutyl, sec-butyl, tert-butyl, propyl, isopropyl, ethyl and methyl radicals, of which propyl, isopropyl, and, particularly, ethyl and methyl are more worthy to be mentioned.

2-7C-Alkyl is a straight-chain or branched alkyl radical having 2 to 7 carbon atoms. Examples are the heptyl, isoheptyl(5-methylhexyl), hexyl, isohexyl(4-methylpentyl), neohexyl(3,3-dimethylbutyl), pentyl, isopentyl(3-methylbutyl), neopentyl(2,2-dimethylpropyl), butyl, isobutyl, sec-butyl, tert-butyl, isopropyl, and, in particular, the propyl and ethyl radicals.

2-4C-Alkyl is a straight-chain or branched alkyl radical having 2 to 4 carbon atoms. Examples are the butyl, isobutyl, sec-butyl, tert-butyl, isopropyl, and, particularly, the propyl and ethyl radical.

Halogen within the meaning of the present invention is iodine or, in particular, bromine, chlorine or fluorine.

1-4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy, ethoxy and methoxy radicals, of which propoxy, isopropoxy, and, particularly, ethoxy and methoxy are more worthy to be mentioned.

The term "cycloalkyl" alone or as part of another group refers to a monocyclic saturated aliphatic hydrocarbon group having the specified numbers of ring carbon atoms, such as for example:

3-7C-Cycloalkyl stands for cyclopropyl, cyclobutyl, cyclopentyl, cyclohexyl and cycloheptyl, of which cyclopropyl, cyclobutyl and cyclopentyl are in particular to be mentioned.

3-7C-Cycloalkyl-1-4C-alkyl stands for one of the abovementioned 1-4C-alkyl radicals, which is substituted by one of the abovementioned 3-7C-cycloalkyl radicals. Examples which may be mentioned are the 3-7C-cycloalkylmethyl radicals, such as e.g. cyclopropylmethyl, cyclobutylmethyl or cyclopentylmethyl, of which cyclopropylmethyl is in particular to be mentioned.

2-4C-Alkenyl is a straight chain or branched alkenyl radical having 2 to 4 carbon atoms. Examples are the 2-butenyl, 3-butenyl(homoalkyl), 1-propenyl, 2-propenyl(allyl) and the ethenyl(vinyl) radicals.

2-4C-Alkenyl is a straight chain or branched alkenyl radical having 2 to 4 carbon atoms. Examples are the 2-butinyl, 3-butinyl(homopropargyl), 1-propinyl, 2-propinyl(propargyl), 1-methyl-2-propinyl(1-methyl-propargyl) and the ethenyl radicals.

2-4C-Alkoxy represents radicals which, in addition to the oxygen atom, contain a straight-chain or branched alkyl radical having 2 to 4 carbon atoms. Examples which may be mentioned are the butoxy, isobutoxy, sec-butoxy, tert-butoxy, propoxy, isopropoxy and particularly the ethoxy radicals.

1-4C-Alkoxy-2-4C-alkoxy represents one of the abovementioned 2-4C-alkoxy radicals, which is substituted by one of the abovementioned 1-4C-alkoxy radicals. Examples which may be mentioned are the 2-methoxyethoxy, 2-ethoxyethoxy and the 2-isopropoxyethoxy radicals.

Hydroxy-2-4C-alkoxy represents one of the abovementioned 2-4C-alkoxy radicals, which is substituted by a hydroxyl radical. Examples which may be mentioned are the 2-hydroxyethoxy and the 3-hydroxypropoxy radicals.

3-7C-Cycloalkoxy stands for cyclopropyloxy, cyclobutyloxy, cyclopentyloxy, cyclohexyloxy or cycloheptyloxy, of which cyclopropyloxy, cyclobutyloxy and cyclopentyloxy are in particular to be mentioned.

3-7C-Cycloalkyl-1-4C-alkoxy stands for one of the abovementioned 1-4C-alkoxy radicals substituted by one of the abovementioned 3-7C-cycloalkyl radicals. Examples which may be mentioned are the 3-7C-cycloalkylmethoxy radicals, such as e.g. cyclopropylmethoxy, cyclobutylmethoxy or cyclopentylmethoxy, of which cyclopropylmethoxy is in particular to be mentioned.

Completely or predominantly fluorine-substituted 1-4C-alkoxy is, for example, the 2,2,3,3,3-pentafluoropropoxy, the perfluoroethoxy, the 1,2,2-trifluoroethoxy and in particular the 1,1,2,2-tetrafluoroethoxy, the 2,2,2-trifluoroethoxy, the trifluoromethoxy and the difluoromethoxy radical, of which the trifluoromethoxy and the difluoromethoxy radicals are preferred. "Predominantly" in this connection means that more than half of the hydrogen atoms of the 1-4C-alkoxy groups are replaced by fluorine atoms.

Phenyl-1-4C-alkoxy represents one of the abovementioned 1-4C-alkoxy radicals, which is substituted by a phenyl radical. Examples which may be mentioned are the phenethoxy and the benzyloxy radicals.

1-4C-Alkylcarbonyl is a carbonyl group, to which one of the abovementioned 1-4C-alkyl radicals is bonded. An example is the acetyl radical ($CH_3CO$—).

1N-(1-4C-alkyl)-pyrazolyl or 1N—(H)-pyrazolyl, respectively, stands for a pyrazolyl radical which is substituted on the ring nitrogen atom in 1-position with 1-4C-alkyl or hydrogen, respectively; such as especially the 1-methyl-pyrazol-5-yl or 1-methyl-pyrazol-3-yl radical.

As completely or partially fluorine-substituted 1-4C-alkyl, for example, the 2,2,3,3,3-penta-fluoropropyl, the perfluoroethyl, the 1,2,2-trifluoroethyl, the 1,1,2,2-tetrafluoroethyl, the 2,2,2-trifluoroethyl, the trifluoromethyl, the difluoromethyl, the monofluoromethyl, the 2-fluoroethyl and the 2,2-difluoroethyl radicals may be mentioned, particularly the 2,2,2-trifluoroethyl, 2,2-difluoroethyl and 2-fluoroethyl radicals.

Het is optionally substituted by one or two substituents independently selected from 1-4C-alkyl and fluorine, and is piperidin-1-yl, morpholin-4-yl, thiomorpholin-4-yl, S-oxo-thiomorpholin-4-yl, S,S-dioxo-thiomorpholin-4-yl, pyrrolidin-1-yl, azetidin-1-yl, homopiperidin-1-yl, 4N—(R113)-piperazin-1-yl, 4N—(R113)-homopiperazin-1-yl, 2,5-dihydro-pyrrol-1-yl, 1,2,3,6-tetrahydropyridin-1-yl, pyrrol-1-yl, pyrazol-1-yl, imidazol-1-yl, triazol-1-yl, or tetrazol-1-yl, in which R113 is hydrogen, 1-4C-alkyl, 3-7C-cycloalkyl, 3-7C-cycloalkyl-1-4C-alkyl, 1-4C-alkylcarbonyl, amidino, or completely or partially fluorine-substituted 1-4C-alkyl, in particular R113 is hydrogen, 1-3C-alkyl, cyclopropyl, cyclopropylmethyl, 1-2C-alkylcarbonyl, or partially fluorine-substituted 1-3C-alkyl (e.g. 2-fluoroethyl, 2,2,2-trifluoroethyl or, particularly, 2,2-difluoroethyl).

In a first embodiment, Het is piperidin-1-yl, morpholin-4-yl, pyrrolidin-1-yl or azetidin-1-yl.

In a second embodiment, Het is 4N—(R113)-piperazin-1-yl, in which

R113 is H, methyl, ethyl, isopropyl, cyclopropyl, cyclopropylmethyl, 1-2C-alkylcarbonyl, 2-fluoroethyl, 2,2,2-trifluoroethyl or 2,2-difluoroethyl;

such as e.g. 4-methyl-piperazin-1-yl or 4-acetyl-piperazin-1-yl.

In a third embodiment, Het is optionally substituted by one or two substituents independently selected from methyl and fluorine, and is piperidin-1-yl, pyrrolidin-1-yl, azetidin-1-yl or homopiperidin-1-yl; such as e.g. piperidin-1-yl, pyrrolidin-1-yl or azetidin-1-yl, or 4-methyl-piperidin-1-yl, 4-fluoro-piperidin-1-yl, 4,4-difluoro-piperidin-1-yl, (S)-3-fluoro-pyrrolidin-1-yl, (R)-3-fluoro-pyrrolidin-1-yl, 3,3-difluoro-pyrrolidin-1-yl, 3-fluoro-azetidin-1-yl or 3,3-difluoro-azetidin-1-yl.

In a fourth embodiment, Het is pyrazol-1-yl, imidazol-1-yl or triazol-1-yl, especially imidazol-1-yl.

In a fifth embodiment, Het is 2,5-dihydro-pyrrol-1-yl or 1,2,3,6-tetrahydropyridin-1-yl.

Amino-1-4C-alkyl denotes abovementioned 1-4C-alkyl radicals which are substituted by an amino group. Examples which may be mentioned are the aminomethyl, the 2-aminoethyl and the 3-aminopropyl radicals.

Hydroxy-2-4C-alkyl denotes abovementioned 2-4C-alkyl radicals which are substituted by a hydroxyl group. Examples which may be mentioned are the 2-hydroxyethyl and the 3-hydroxypropyl radicals.

1-4C-Alkoxy-2-4C-alkyl denotes abovementioned 2-4C-alkyl radicals which are substituted by one of the abovementioned 1-4C-alkoxy radicals. Examples which may be mentioned are the 2-methoxyethyl and the 3-methoxypropyl radicals.

Mono- or di-1-4C-alkylamino radicals contain, in addition to the nitrogen atom, one or two of the abovementioned 1-4C-alkyl radicals. Examples which may be mentioned are mono-1-4C-alkylamino radicals, like methylamino, ethylamino or isopropylamino, and di-1-4C-alkylamino radicals, like dimethylamino, diethylamine or diisopropylamino.

Mono- or di-1-4C-alkylamino-1-4C-alkyl represents one of the aforementioned 1-4C-alkyl groups, which is substituted by one of the aforementioned mono- or di-1-4C-alkylamino groups. Examples which may be mentioned are the methylamino-methyl, dimethylamino-methyl, 2-methylamino-ethyl, 2-dimethylamino-ethyl, 3-methylamino-propyl or 3-dimethylamino-propyl radicals.

4N—(R113)-piperazin-1-yl or 4N—(R113)-homopiperazin-1-yl stands for a piperazin-1-yl or homopiperazin-1-yl radical, respectively, which is substituted by R113 on the ring nitrogen atom in 4-position.

The term 2-(R11)-ethyl stands for ethyl which is substituted in 2-position by R11. The term 3-(R11)-propyl stands for propyl which is substituted in 3-position by R11. The term 4-(R11)-butyl stands for butyl which is substituted in 4-position by R11.

In general and unless otherwise mentioned, the heterocyclic radicals include all the possible isomeric forms thereof, e.g. the positional isomers thereof. Thus, for example, the term triazol-1-yl includes [1,2,3]triazol-1-yl, [1,3,4]triazol-1-yl and [1,2,4]triazol-1-yl, or the term isoxazolyl includes isoxazol-3-yl, isoxazol-4-yl and isoxazol-5-yl.

Constituents which optionally substituted as stated herein, may be substituted, unless otherwise noted, at any possible position.

Unless otherwise noted, the carbocyclic radicals mentioned herein may be substituted by its substituents or parent molecular groups at any possible position.

The heterocyclic groups mentioned herein may be substituted by their given substituents or parent molecular groups, unless otherwise noted, at any possible position, such as e.g. at any substitutable ring carbon or ring nitrogen atom.

Unless otherwise noted, rings containing quaternizable amino- or imino-type ring nitrogen atoms (—N=) may be preferably not quaternized on these amino- or imino-type ring nitrogen atoms by the mentionned substituents or parent molecular groups.

When any variable occurs more than one time in any constituent, each definition is independent.

The substituents R2 and R3 of compounds of formula I can be attached in the ortho, meta or para position with respect to the binding position in which the phenyl ring is bonded to the scaffold. In one embodiment R3 is hydrogen. In a particular embodiment R2 and R3 are both hydrogen.

The substituents R5 and R6 may be attached, unless otherwise noted, at any position of the benzene moiety of the scaffold, whereby preference is given to the attachment of none of R5 and R6 to the 8-position of the scaffold. In one embodiment, R5 is attached in the 5-position of the scaffold; in another embodiment, R5 is attached in the 7-position of the scaffold; and in yet another embodiment R5 is attached in the 6-position of the scaffold; wherein, especially, R6 is hydrogen, respectively; or wherein R6 is fluorine, respectively. In a particular embodiment, R5 is attached in the 6-position of the scaffold. In a more particular embodiment, R5 is attached in the 6-position of the scaffold, and R6 is hydrogen. In another embodiment, R5 is attached in the 6-position of the scaffold, and R6 is attached to the 7-position of the scaffold and is fluorine. In yet another embodiment, R5 is attached in the 6-position of the scaffold, and R6 is attached to the 5-position of the scaffold and is fluorine.

Numbering:

(I)

The compounds of formula I are chiral compounds having chiral centers at least in positions 3a and 10.

Preferences of the Compounds

Preferred compounds according to this invention worthy to be mentioned are those compounds of formula I, in which R1 is 2-4C-alkyl substituted by N(R111)R112, in which R111 is 1-4C-alkyl, 2-4C-alkenyl, 2-4C-alkenyl, cyclopropyl, cyclobutyl, cyclopropylmethyl, hydroxy-2-4C-alkyl, 1-2C-alkoxy-2-4C-alkyl, isoxazolyl, 1N-(1-3C-alkyl)-pyrazolyl, or mono-, di- or tri-fluorine-substituted 1-4C-alkyl, R112 is hydrogen, 1-4C-alkyl, cyclopropyl, or cyclopropylmethyl, or R111 and R112 together and with inclusion of the nitrogen atom, to which they are bonded, form a ring Het, in which Het is piperidin-1-yl, morpholin-4-yl, thiomorpholin-4-yl, S-oxo-thiomorpholin-4-yl, S,S-dioxo-thiomorpholin-4-yl, pyrrolidin-1-yl, azetidin-1-yl, homopiperidin-1-yl, 4N—(R113)-piperazin-1-yl, 4N—(R113)-homopiperazin-1-yl, 2,5-dihydro-pyrrol-1-yl, 1,2,3,6-tetrahydropyridin-1-yl, pyrrol-1-yl, pyrazol-1-yl, imidazol-1-yl, triazol-1-yl, or, tetrazol-1-yl, in which R113 is hydrogen, 1-3C-alkyl, cyclopropyl, cyclopropylmethyl, 1-3C-alkylcarbonyl, 2-fluoroethyl, 2,2-difluoroethyl, or 2,2,2-trifluoroethyl, wherein said Het may be optionally substituted by one or two substituents independently selected from fluorine and methyl, R2 is hydrogen, R3 is hydrogen, R4 is methyl or ethyl, in particular, R4 is methyl, R5 is methyl, ethyl, propyl, isopropyl, fluorine, chlorine, bromine, methoxy, ethoxy, propoxy, isopropoxy, trifluoromethyl, 2-methoxy-ethoxy, cyclopropyloxy, cyclopropylmethoxy, or completely or predominantly fluorine-substituted 1-2C-alkoxy, in particular, R5 is chlorine, bromine, fluorine, methoxy, ethoxy, difluoromethoxy or trifluoromethoxy, R6 is hydrogen or fluorine, wherein R5 is bonded to the 5-, 7- or, particularly, 6-position of the scaffold, and wherein R6 is bonded to the 5- or 7-position of the scaffold, and the salts of these compounds.

Compounds according to this invention in particular worthy to be mentioned are those compounds of formula I, in which R1 is 2-(R11)-ethyl, or 3-(R11)-propyl, in which R11 is —N(R111)R112, in which either R111 is methyl, ethyl, propyl, isopropyl, isobutyl, tertbutyl, allyl, propargyl, 1-methyl-propargyl, cyclopropyl, cyclobutyl, cyclopropylmethyl, 2-hydroxyethyl, 2-methoxyethyl, 2-fluoroethyl, 2,2-difluoroethyl, or 2,2,2-trifluoroethyl, and R112 is hydrogen, or R111 is methyl, ethyl, propyl, isopropyl, isobutyl, tertbutyl, allyl, propargyl, 1-methyl-propargyl, cyclopropyl, cyclobutyl, cyclopropylmethyl, 2-hydroxyethyl, 2-methoxyethyl, 2-fluoroethyl, 2,2-difluoroethyl, or 2,2,2-trifluoroethyl, and R112 is methyl, or R111 is ethyl, propyl, isopropyl, allyl, propargyl, 1-methyl-propargyl, cyclopropyl, cyclobutyl, cyclopropylmethyl, 2-hydroxyethyl, 2-methoxyethyl, 2-fluoroethyl, 2,2-difluoroethyl, or 2,2,2-trifluoroethyl, and R112 is ethyl, or R111 and R112 together and with inclusion of the nitrogen atom, to which they are bonded, form a ring Het, in which either Het is piperidin-1-yl, morpholin-4-yl, pyrrolidin-1-yl, azetidin-1-yl, homopiperidin-1-yl, 4N—(R113)-piperazin-1-yl, 4N—(R113)-homopiperazin-1-yl, 2,5-dihydro-pyrrol-1-yl, 1,2,3,6-tetrahydropyridin-1-yl, 4-methyl-piperidin-1-yl, 4-fluoro-piperidin-1-yl, 4,4-difluoropiperidin-1-yl, (S)-3-fluoro-pyrrolidin-1-yl, (R)-3-fluoro-pyrrolidin-1-yl, or 3,3-difluoro-pyrrolidin-1-yl, in which R113 is methyl or acetyl, or Net is pyrazol-1-yl, or imidazol-1-yl, R2 is hydrogen, R3 is hydrogen, R4 is methyl, R5 is chlorine, bromine, fluorine, ethoxy, methoxy, difluoromethoxy or trifluoromethoxy, in more particular, R5 is chlorine, bromine, ethoxy, methoxy or difluoromethoxy, R6 is hydrogen or fluorine, wherein R5 is bonded to the 6-position of the scaffold, and wherein R6 is bonded to the 5- or, particularly, 7-position of the scaffold, and the salts of these compounds.

Compounds according to this invention in more particular worthy to be mentioned are those compounds of formula I, in which R1 is 2-(R11)-ethyl, or 3-(R11)-propyl, in which R11 is —N(R111)R112, in which either R111 is methyl, ethyl, isopropyl, isobutyl, tertbutyl, allyl, cyclopropyl, cyclobutyl, cyclopropylmethyl, 2-hydroxyethyl, or 2-methoxyethyl, and R112 is hydrogen, or R111 is methyl, ethyl, isopropyl, allyl, cyclopropyl, cyclobutyl, cyclopropylmethyl, 2-hydroxyethyl, or 2-methoxyethyl, and R112 is methyl, or R111 is ethyl, 2-hydroxyethyl, or 2-methoxyethyl, and R112 is ethyl, or
R111 and R112 together and with inclusion of the nitrogen atom, to which they are bonded, form a ring Het, in which Het is piperidin-1-yl, pyrrolidin-1-yl, azetidin-1-yl, 2,5-dihydro-pyrrol-1-yl, or 1,2,3,6-tetrahydropyridin-1-yl,
R2 is hydrogen,
R3 is hydrogen,
R4 is methyl,
R5 is chlorine, bromine, ethoxy, methoxy or difluoromethoxy,
R6 is hydrogen or fluorine,
wherein R5 is bonded to the 6-position of the scaffold, and
wherein R6 is bonded to the 7-position of the scaffold,
and the salts of these compounds.

Most preferred are those compounds of formula I, in which
R1 and R5 are listed in Table 1
R2 and R3 and R6 are hydrogen, and
R4 is methyl,
and the salts thereof,

TABLE 1

| No. | R1 | R5 |
|---|---|---|
| 1.12 | 2-(dimethylamino)-ethyl | —CH$_3$ |
| 1.13 | 2-(dimethylamino)-ethyl | —Br |
| 1.14 | 2-(dimethylamino)-ethyl | —F |
| 1.15 | 2-(dimethylamino)-ethyl | —OCH$_3$ |
| 1.16 | 2-(dimethylamino)-ethyl | —OCH$_2$CH$_3$ |
| 1.17 | 2-(dimethylamino)-ethyl | —Cl |
| 1.18 | 2-(dimethylamino)-ethyl | —OCH$_2$CH$_2$OCH$_3$ |
| 1.19 | 2-(dimethylamino)-ethyl | cyclopropylmethoxy |
| 1.20 | 2-(dimethylamino)-ethyl | —CF$_3$ |
| 1.21 | 2-(dimethylamino)-ethyl | difluoromethoxy |
| 1.22 | 2-(dimethylamino)-ethyl | trifluoromethoxy |
| 1.23 | 3-(dimethylamino)-propyl | —CH$_3$ |
| 1.24 | 3-(dimethylamino)-propyl | —Br |
| 1.25 | 3-(dimethylamino)-propyl | —F |
| 1.26 | 3-(dimethylamino)-propyl | —OCH$_3$ |
| 1.27 | 3-(dimethylamino)-propyl | —OCH$_2$CH$_3$ |
| 1.28 | 3-(dimethylamino)-propyl | —Cl |
| 1.29 | 3-(dimethylamino)-propyl | —OCH$_2$CH$_2$OCH$_3$ |
| 1.30 | 3-(dimethylamino)-propyl | cyclopropylmethoxy |
| 1.31 | 3-(dimethylamino)-propyl | —CF$_3$ |
| 1.32 | 3-(dimethylamino)-propyl | difluoromethoxy |
| 1.33 | 3-(dimethylamino)-propyl | trifluoromethoxy |
| 1.34 | 2-(morpholin-4-yl)-ethyl | —CH$_3$ |
| 1.35 | 2-(morpholin-4-yl)-ethyl | —Br |
| 1.36 | 2-(morpholin-4-yl)-ethyl | —F |
| 1.37 | 2-(morpholin-4-yl)-ethyl | —OCH$_3$ |
| 1.38 | 2-(morpholin-4-yl)-ethyl | —OCH$_2$CH$_3$ |
| 1.39 | 2-(morpholin-4-yl)-ethyl | —Cl |
| 1.40 | 2-(morpholin-4-yl)-ethyl | —OCH$_2$CH$_2$OCH$_3$ |
| 1.41 | 2-(morpholin-4-yl)-ethyl | cyclopropylmethoxy |
| 1.42 | 2-(morpholin-4-yl)-ethyl | —CF$_3$ |
| 1.43 | 2-(morpholin-4-yl)-ethyl | difluoromethoxy |
| 1.44 | 2-(morpholin-4-yl)-ethyl | trifluoromethoxy |
| 1.45 | 2-(pyrrolidin-1-yl)-ethyl | —CH$_3$ |
| 1.46 | 2-(pyrrolidin-1-yl)-ethyl | —Br |
| 1.47 | 2-(pyrrolidin-1-yl)-ethyl | —F |
| 1.48 | 2-(pyrrolidin-1-yl)-ethyl | —OCH$_3$ |
| 1.49 | 2-(pyrrolidin-1-yl)-ethyl | —OCH$_2$CH$_3$ |
| 1.50 | 2-(pyrrolidin-1-yl)-ethyl | —Cl |
| 1.51 | 2-(pyrrolidin-1-yl)-ethyl | —OCH$_2$CH$_2$OCH$_3$ |
| 1.52 | 2-(pyrrolidin-1-yl)-ethyl | cyclopropylmethoxy |
| 1.53 | 2-(pyrrolidin-1-yl)-ethyl | —CF$_3$ |
| 1.54 | 2-(pyrrolidin-1-yl)-ethyl | difluoromethoxy |
| 1.55 | 2-(pyrrolidin-1-yl)-ethyl | trifluoromethoxy |
| 1.56 | 2-(imidazol-1-yl)-ethyl | —CH$_3$ |
| 1.57 | 2-(imidazol-1-yl)-ethyl | —Br |
| 1.58 | 2-(imidazol-1-yl)-ethyl | —F |
| 1.59 | 2-(imidazol-1-yl)-ethyl | —OCH$_3$ |
| 1.60 | 2-(imidazol-1-yl)-ethyl | —OCH$_2$CH$_3$ |
| 1.61 | 2-(imidazol-1-yl)-ethyl | —Cl |
| 1.62 | 2-(imidazol-1-yl)-ethyl | —OCH$_2$CH$_2$OCH$_3$ |
| 1.63 | 2-(imidazol-1-yl)-ethyl | cyclopropylmethoxy |
| 1.64 | 2-(imidazol-1-yl)-ethyl | —CF$_3$ |

TABLE 1-continued

| No. | R1 | R5 |
|---|---|---|
| 1.65 | 2-(imidazol-1-yl)-ethyl | difluoromethoxy |
| 1.66 | 2-(imidazol-1-yl)-ethyl | trifluoromethoxy |
| 1.67 | 2-(4-methyl-piperazin-1-yl)-ethyl | —CH$_3$ |
| 1.68 | 2-(4-methyl-piperazin-1-yl)-ethyl | —Br |
| 1.69 | 2-(4-methyl-piperazin-1-yl)-ethyl | —F |
| 1.70 | 2-(4-methyl-piperazin-1-yl)-ethyl | —OCH$_3$ |
| 1.71 | 2-(4-methyl-piperazin-1-yl)-ethyl | —OCH$_2$CH$_3$ |
| 1.72 | 2-(4-methyl-piperazin-1-yl)-ethyl | —Cl |
| 1.73 | 2-(4-methyl-piperazin-1-yl)-ethyl | —OCH$_2$CH$_2$OCH$_3$ |
| 1.74 | 2-(4-methyl-piperazin-1-yl)-ethyl | cyclopropylmethoxy |
| 1.75 | 2-(4-methyl-piperazin-1-yl)-ethyl | —CF$_3$ |
| 1.76 | 2-(4-methyl-piperazin-1-yl)-ethyl | difluoromethoxy |
| 1.77 | 2-(4-methyl-piperazin-1-yl)-ethyl | trifluoromethoxy |
| 1.78 | 3-(morpholin-4-yl)-propyl | —CH$_3$ |
| 1.79 | 3-(morpholin-4-yl)-propyl | —Br |
| 1.80 | 3-(morpholin-4-yl)-propyl | —F |
| 1.81 | 3-(morpholin-4-yl)-propyl | —OCH$_3$ |
| 1.82 | 3-(morpholin-4-yl)-propyl | —OCH$_2$CH$_3$ |
| 1.83 | 3-(morpholin-4-yl)-propyl | —Cl |
| 1.84 | 3-(morpholin-4-yl)-propyl | —OCH$_2$CH$_2$OCH$_3$ |
| 1.85 | 3-(morpholin-4-yl)-propyl | cyclopropylmethoxy |
| 1.86 | 3-(morpholin-4-yl)-propyl | —CF$_3$ |
| 1.87 | 3-(morpholin-4-yl)-propyl | difluoromethoxy |
| 1.88 | 3-(morpholin-4-yl)-propyl | trifluoromethoxy |
| 1.89 | 3-(pyrrolidin-1-yl)-propyl | —CH$_3$ |
| 1.90 | 3-(pyrrolidin-1-yl)-propyl | —Br |
| 1.91 | 3-(pyrrolidin-1-yl)-propyl | —F |
| 1.92 | 3-(pyrrolidin-1-yl)-propyl | —OCH$_3$ |
| 1.93 | 3-(pyrrolidin-1-yl)-propyl | —OCH$_2$CH$_3$ |
| 1.94 | 3-(pyrrolidin-1-yl)-propyl | —Cl |
| 1.95 | 3-(pyrrolidin-1-yl)-propyl | —OCH$_2$CH$_2$OCH$_3$ |
| 1.96 | 3-(pyrrolidin-1-yl)-propyl | cyclopropylmethoxy |
| 1.97 | 3-(pyrrolidin-1-yl)-propyl | —CF$_3$ |
| 1.98 | 3-(pyrrolidin-1-yl)-propyl | difluoromethoxy |
| 1.99 | 3-(pyrrolidin-1-yl)-propyl | trifluoromethoxy |
| 1.100 | 3-(imidazol-1-yl)-propyl | —CH$_3$ |
| 1.101 | 3-(imidazol-1-yl)-propyl | —Br |
| 1.102 | 3-(imidazol-1-yl)-propyl | —F |
| 1.103 | 3-(imidazol-1-yl)-propyl | —OCH$_3$ |
| 1.104 | 3-(imidazol-1-yl)-propyl | —OCH$_2$CH$_3$ |
| 1.105 | 3-(imidazol-1-yl)-propyl | —Cl |
| 1.106 | 3-(imidazol-1-yl)-propyl | —OCH$_2$CH$_2$OCH$_3$ |
| 1.107 | 3-(imidazol-1-yl)-propyl | cyclopropylmethoxy |
| 1.108 | 3-(imidazol-1-yl)-propyl | —CF$_3$ |
| 1.109 | 3-(imidazol-1-yl)-propyl | difluoromethoxy |
| 1.110 | 3-(imidazol-1-yl)-propyl | trifluoromethoxy |
| 1.111 | 3-(4-methyl-piperazin-1-yl)-propyl | —CH$_3$ |
| 1.112 | 3-(4-methyl-piperazin-1-yl)-propyl | —Br |
| 1.113 | 3-(4-methyl-piperazin-1-yl)-propyl | —F |
| 1.114 | 3-(4-methyl-piperazin-1-yl)-propyl | —OCH$_3$ |
| 1.115 | 3-(4-methyl-piperazin-1-yl)-propyl | —OCH$_2$CH$_3$ |
| 1.116 | 3-(4-methyl-piperazin-1-yl)-propyl | —Cl |
| 1.117 | 3-(4-methyl-piperazin-1-yl)-propyl | —OCH$_2$CH$_2$OCH$_3$ |
| 1.118 | 3-(4-methyl-piperazin-1-yl)-propyl | cyclopropylmethoxy |
| 1.119 | 3-(4-methyl-piperazin-1-yl)-propyl | —CF$_3$ |
| 1.120 | 3-(4-methyl-piperazin-1-yl)-propyl | difluoromethoxy |
| 1.121 | 3-(4-methyl-piperazin-1-yl)-propyl | trifluoromethoxy |
| 1.144 | 2-(methylamino)-ethyl | —CH$_3$ |
| 1.145 | 2-(methylamino)-ethyl | —Br |
| 1.146 | 2-(methylamino)-ethyl | —F |
| 1.147 | 2-(methylamino)-ethyl | —OCH$_3$ |
| 1.148 | 2-(methylamino)-ethyl | —OCH$_2$CH$_3$ |
| 1.149 | 2-(methylamino)-ethyl | —Cl |
| 1.150 | 2-(methylamino)-ethyl | —OCH$_2$CH$_2$OCH$_3$ |
| 1.151 | 2-(methylamino)-ethyl | cyclopropylmethoxy |
| 1.152 | 2-(methylamino)-ethyl | trifluoromethyl |
| 1.153 | 2-(methylamino)-ethyl | difluoromethoxy |
| 1.154 | 2-(methylamino)-ethyl | trifluoromethoxy |
| 1.155 | 2-(ethylamino)-ethyl | —CH$_3$ |
| 1.156 | 2-(ethylamino)-ethyl | —Br |
| 1.157 | 2-(ethylamino)-ethyl | —F |
| 1.158 | 2-(ethylamino)-ethyl | —OCH$_3$ |
| 1.159 | 2-(ethylamino)-ethyl | —OCH$_2$CH$_3$ |
| 1.160 | 2-(ethylamino)-ethyl | —Cl |
| 1.161 | 2-(ethylamino)-ethyl | —OCH$_2$CH$_2$OCH$_3$ |
| 1.162 | 2-(ethylamino)-ethyl | cyclopropylmethoxy |
| 1.163 | 2-(ethylamino)-ethyl | trifluoromethyl |
| 1.164 | 2-(ethylamino)-ethyl | difluoromethoxy |

TABLE 1-continued

| No. | R1 | R5 |
|---|---|---|
| 1.165 | 2-(ethylamino)-ethyl | trifluoromethoxy |
| 1.166 | 2-(azetidin-1-yl)-ethyl | —CH$_3$ |
| 1.167 | 2-(azetidin-1-yl)-ethyl | —Br |
| 1.168 | 2-(azetidin-1-yl)-ethyl | —F |
| 1.169 | 2-(azetidin-1-yl)-ethyl | —OCH$_3$ |
| 1.170 | 2-(azetidin-1-yl)-ethyl | —OCH$_2$CH$_3$ |
| 1.171 | 2-(azetidin-1-yl)-ethyl | —Cl |
| 1.172 | 2-(azetidin-1-yl)-ethyl | —OCH$_2$CH$_2$OCH$_3$ |
| 1.173 | 2-(azetidin-1-yl)-ethyl | cyclopropylmethoxy |
| 1.174 | 2-(azetidin-1-yl)-ethyl | trifluoromethyl |
| 1.175 | 2-(azetidin-1-yl)-ethyl | difluoromethoxy |
| 1.176 | 2-(azetidin-1-yl)-ethyl | trifluoromethoxy |
| 1.177 | 2-(4-acetyl-piperazin-1-yl)-ethyl | —CH$_3$ |
| 1.178 | 2-(4-acetyl-piperazin-1-yl)-ethyl | —Br |
| 1.179 | 2-(4-acetyl-piperazin-1-yl)-ethyl | —F |
| 1.180 | 2-(4-acetyl-piperazin-1-yl)-ethyl | —OCH$_3$ |
| 1.181 | 2-(4-acetyl-piperazin-1-yl)-ethyl | —OCH$_2$CH$_3$ |
| 1.182 | 2-(4-acetyl-piperazin-1-yl)-ethyl | —Cl |
| 1.183 | 2-(4-acetyl-piperazin-1-yl)-ethyl | —OCH$_2$CH$_2$OCH$_3$ |
| 1.184 | 2-(4-acetyl-piperazin-1-yl)-ethyl | cyclopropylmethoxy |
| 1.185 | 2-(4-acetyl-piperazin-1-yl)-ethyl | trifluoromethyl |
| 1.186 | 2-(4-acetyl-piperazin-1-yl)-ethyl | difluoromethoxy |
| 1.187 | 2-(4-acetyl-piperazin-1-yl)-ethyl | trifluoromethoxy |
| 1.188 | 2-(3,3-difluoropyrrolidin-1-yl)-ethyl | —CH$_3$ |
| 1.189 | 2-(3,3-difluoropyrrolidin-1-yl)-ethyl | —Br |
| 1.190 | 2-(3,3-difluoropyrrolidin-1-yl)-ethyl | —F |
| 1.191 | 2-(3,3-difluoropyrrolidin-1-yl)-ethyl | —OCH$_3$ |
| 1.192 | 2-(3,3-difluoropyrrolidin-1-yl)-ethyl | —OCH$_2$CH$_3$ |
| 1.193 | 2-(3,3-difluoropyrrolidin-1-yl)-ethyl | —Cl |
| 1.194 | 2-(3,3-difluoropyrrolidin-1-yl)-ethyl | —OCH$_2$CH$_2$OCH$_3$ |
| 1.195 | 2-(3,3-difluoropyrrolidin-1-yl)-ethyl | cyclopropylmethoxy |
| 1.196 | 2-(3,3-difluoropyrrolidin-1-yl)-ethyl | trifluoromethyl |
| 1.197 | 2-(3,3-difluoropyrrolidin-1-yl)-ethyl | difluoromethoxy |
| 1.198 | 2-(3,3-difluoropyrrolidin-1-yl)-ethyl | trifluoromethoxy |
| 1.199 | 2-(2-fluoroethylamino)-ethyl | —CH$_3$ |
| 1.200 | 2-(2-fluoroethylamino)-ethyl | —Br |
| 1.201 | 2-(2-fluoroethylamino)-ethyl | —F |
| 1.202 | 2-(2-fluoroethylamino)-ethyl | —OCH$_3$ |
| 1.203 | 2-(2-fluoroethylamino)-ethyl | —OCH$_2$CH$_3$ |
| 1.204 | 2-(2-fluoroethylamino)-ethyl | —Cl |
| 1.205 | 2-(2-fluoroethylamino)-ethyl | —OCH$_2$CH$_2$OCH$_3$ |
| 1.206 | 2-(2-fluoroethylamino)-ethyl | cyclopropylmethoxy |
| 1.207 | 2-(2-fluoroethylamino)-ethyl | trifluoromethyl |
| 1.208 | 2-(2-fluoroethylamino)-ethyl | difluoromethoxy |
| 1.209 | 2-(2-fluoroethylamino)-ethyl | trifluoromethoxy |
| 1.210 | 2-(2,2-difluoroethylamino)-ethyl | —CH$_3$ |
| 1.211 | 2-(2,2-difluoroethylamino)-ethyl | —Br |
| 1.212 | 2-(2,2-difluoroethylamino)-ethyl | —F |
| 1.213 | 2-(2,2-difluoroethylamino)-ethyl | —OCH$_3$ |
| 1.214 | 2-(2,2-difluoroethylamino)-ethyl | —OCH$_2$CH$_3$ |
| 1.215 | 2-(2,2-difluoroethylamino)-ethyl | —Cl |
| 1.216 | 2-(2,2-difluoroethylamino)-ethyl | —OCH$_2$CH$_2$OCH$_3$ |
| 1.217 | 2-(2,2-difluoroethylamino)-ethyl | cyclopropylmethoxy |
| 1.218 | 2-(2,2-difluoroethylamino)-ethyl | trifluoromethyl |
| 1.219 | 2-(2,2-difluoroethylamino)-ethyl | difluoromethoxy |
| 1.220 | 2-(2,2-difluoroethylamino)-ethyl | trifluoromethoxy |
| 1.221 | 2-(2,2,2-trifluoroethylamino)-ethyl | —CH$_3$ |
| 1.222 | 2-(2,2,2-trifluoroethylamino)-ethyl | —Br |
| 1.223 | 2-(2,2,2-trifluoroethylamino)-ethyl | —F |
| 1.224 | 2-(2,2,2-trifluoroethylamino)-ethyl | —OCH$_3$ |
| 1.225 | 2-(2,2,2-trifluoroethylamino)-ethyl | —OCH$_2$CH$_3$ |
| 1.226 | 2-(2,2,2-trifluoroethylamino)-ethyl | —Cl |
| 1.227 | 2-(2,2,2-trifluoroethylamino)-ethyl | —OCH$_2$CH$_2$OCH$_3$ |
| 1.228 | 2-(2,2,2-trifluoroethylamino)-ethyl | cyclopropylmethoxy |
| 1.229 | 2-(2,2,2-trifluoroethylamino)-ethyl | trifluoromethyl |
| 1.230 | 2-(2,2,2-trifluoroethylamino)-ethyl | difluoromethoxy |
| 1.231 | 2-(2,2,2-trifluoroethylamino)-ethyl | trifluoromethoxy |
| 1.232 | 2-(isopropylamino)-ethyl | —CH$_3$ |
| 1.233 | 2-(isopropylamino)-ethyl | —Br |
| 1.234 | 2-(isopropylamino)-ethyl | —F |
| 1.235 | 2-(isopropylamino)-ethyl | —OCH$_3$ |
| 1.236 | 2-(isopropylamino)-ethyl | —OCH$_2$CH$_3$ |
| 1.237 | 2-(isopropylamino)-ethyl | —Cl |
| 1.238 | 2-(isopropylamino)-ethyl | —OCH$_2$CH$_2$OCH$_3$ |
| 1.239 | 2-(isopropylamino)-ethyl | cyclopropylmethoxy |
| 1.240 | 2-(isopropylamino)-ethyl | trifluoromethyl |
| 1.241 | 2-(isopropylamino)-ethyl | difluoromethoxy |
| 1.242 | 2-(isopropylamino)-ethyl | trifluoromethoxy |
| 1.243 | 2-(isobutylamino)-ethyl | —CH$_3$ |
| 1.244 | 2-(isobutylamino)-ethyl | —Br |
| 1.245 | 2-(isobutylamino)-ethyl | —F |
| 1.246 | 2-(isobutylamino)-ethyl | —OCH$_3$ |
| 1.247 | 2-(isobutylamino)-ethyl | —OCH$_2$CH$_3$ |
| 1.248 | 2-(isobutylamino)-ethyl | —Cl |
| 1.249 | 2-(isobutylamino)-ethyl | —OCH$_2$CH$_2$OCH$_3$ |
| 1.250 | 2-(isobutylamino)-ethyl | cyclopropylmethoxy |
| 1.251 | 2-(isobutylamino)-ethyl | trifluoromethyl |
| 1.252 | 2-(isobutylamino)-ethyl | difluoromethoxy |
| 1.253 | 2-(isobutylamino)-ethyl | trifluoromethoxy |
| 1.254 | 2-(N-cyclopropylmethyl-amino)-ethyl | —CH$_3$ |
| 1.255 | 2-(N-cyclopropylmethyl-amino)-ethyl | —Br |
| 1.256 | 2-(N-cyclopropylmethyl-amino)-ethyl | —F |
| 1.257 | 2-(N-cyclopropylmethyl-amino)-ethyl | —OCH$_3$ |
| 1.258 | 2-(N-cyclopropylmethyl-amino)-ethyl | —OCH$_2$CH$_3$ |
| 1.259 | 2-(N-cyclopropylmethyl-amino)-ethyl | —Cl |
| 1.260 | 2-(N-cyclopropylmethyl-amino)-ethyl | —OCH$_2$CH$_2$OCH$_3$ |
| 1.261 | 2-(N-cyclopropylmethyl-amino)-ethyl | cyclopropylmethoxy |
| 1.262 | 2-(N-cyclopropylmethyl-amino)-ethyl | trifluoromethyl |
| 1.263 | 2-(N-cyclopropylmethyl-amino)-ethyl | difluoromethoxy |
| 1.264 | 2-(N-cyclopropylmethyl-amino)-ethyl | trifluoromethoxy |
| 1.265 | 2-(cyclopropylamino)-ethyl | —CH$_3$ |
| 1.266 | 2-(cyclopropylamino)-ethyl | —Br |
| 1.267 | 2-(cyclopropylamino)-ethyl | —F |
| 1.268 | 2-(cyclopropylamino)-ethyl | —OCH$_3$ |
| 1.269 | 2-(cyclopropylamino)-ethyl | —OCH$_2$CH$_3$ |
| 1.270 | 2-(cyclopropylamino)-ethyl | —Cl |
| 1.271 | 2-(cyclopropylamino)-ethyl | —OCH$_2$CH$_2$OCH$_3$ |
| 1.272 | 2-(cyclopropylamino)-ethyl | cyclopropylmethoxy |
| 1.273 | 2-(cyclopropylamino)-ethyl | trifluoromethyl |
| 1.274 | 2-(cyclopropylamino)-ethyl | difluoromethoxy |
| 1.275 | 2-(cyclopropylamino)-ethyl | trifluoromethoxy |
| 1.276 | 2-(cyclobutylamino)-ethyl | —CH$_3$ |
| 1.277 | 2-(cyclobutylamino)-ethyl | —Br |
| 1.278 | 2-(cyclobutylamino)-ethyl | —F |
| 1.279 | 2-(cyclobutylamino)-ethyl | —OCH$_3$ |
| 1.280 | 2-(cyclobutylamino)-ethyl | —OCH$_2$CH$_3$ |
| 1.281 | 2-(cyclobutylamino)-ethyl | —Cl |
| 1.282 | 2-(cyclobutylamino)-ethyl | —OCH$_2$CH$_2$OCH$_3$ |
| 1.283 | 2-(cyclobutylamino)-ethyl | cyclopropylmethoxy |
| 1.284 | 2-(cyclobutylamino)-ethyl | trifluoromethyl |
| 1.285 | 2-(cyclobutylamino)-ethyl | difluoromethoxy |
| 1.286 | 2-(cyclobutylamino)-ethyl | trifluoromethoxy |
| 1.287 | 2-(N-ethyl-N-methyl-amino)-ethyl | —CH$_3$ |
| 1.288 | 2-(N-ethyl-N-methyl-amino)-ethyl | —Br |
| 1.289 | 2-(N-ethyl-N-methyl-amino)-ethyl | —F |
| 1.290 | 2-(N-ethyl-N-methyl-amino)-ethyl | —OCH$_3$ |
| 1.291 | 2-(N-ethyl-N-methyl-amino)-ethyl | —OCH$_2$CH$_3$ |
| 1.292 | 2-(N-ethyl-N-methyl-amino)-ethyl | —Cl |
| 1.293 | 2-(N-ethyl-N-methyl-amino)-ethyl | —OCH$_2$CH$_2$OCH$_3$ |
| 1.294 | 2-(N-ethyl-N-methyl-amino)-ethyl | cyclopropylmethoxy |
| 1.295 | 2-(N-ethyl-N-methyl-amino)-ethyl | trifluoromethyl |
| 1.296 | 2-(N-ethyl-N-methyl-amino)-ethyl | difluoromethoxy |
| 1.297 | 2-(N-ethyl-N-methyl-amino)-ethyl | trifluoromethoxy |
| 1.298 | 2-(diethylamino)-ethyl | —CH$_3$ |
| 1.299 | 2-(diethylamino)-ethyl | —Br |
| 1.300 | 2-(diethylamino)-ethyl | —F |
| 1.301 | 2-(diethylamino)-ethyl | —OCH$_3$ |
| 1.302 | 2-(diethylamino)-ethyl | —OCH$_2$CH$_3$ |
| 1.303 | 2-(diethylamino)-ethyl | —Cl |
| 1.304 | 2-(diethylamino)-ethyl | —OCH$_2$CH$_2$OCH$_3$ |
| 1.305 | 2-(diethylamino)-ethyl | cyclopropylmethoxy |
| 1.306 | 2-(diethylamino)-ethyl | trifluoromethyl |
| 1.307 | 2-(diethylamino)-ethyl | difluoromethoxy |
| 1.308 | 2-(diethylamino)-ethyl | trifluoromethoxy |
| 1.309 | 2-(N-isopropyl-N-methyl-amino)-ethyl | —CH$_3$ |
| 1.310 | 2-(N-isopropyl-N-methyl-amino)-ethyl | —Br |
| 1.311 | 2-(N-isopropyl-N-methyl-amino)-ethyl | —F |
| 1.312 | 2-(N-isopropyl-N-methyl-amino)-ethyl | —OCH$_3$ |
| 1.313 | 2-(N-isopropyl-N-methyl-amino)-ethyl | —OCH$_2$CH$_3$ |
| 1.314 | 2-(N-isopropyl-N-methyl-amino)-ethyl | —Cl |

TABLE 1-continued

| No. | R1 | R5 |
|---|---|---|
| 1.315 | 2-(N-isopropyl-N-methyl-amino)-ethyl | —OCH$_2$CH$_2$OCH$_3$ |
| 1.316 | 2-(N-isopropyl-N-methyl-amino)-ethyl | cyclopropylmethoxy |
| 1.317 | 2-(N-isopropyl-N-methyl-amino)-ethyl | trifluoromethyl |
| 1.318 | 2-(N-isopropyl-N-methyl-amino)-ethyl | difluoromethoxy |
| 1.319 | 2-(N-isopropyl-N-methyl-amino)-ethyl | trifluoromethoxy |
| 1.320 | 2-((R)-3-fluoro-pyrrolidin-1-yl)-ethyl | —CH$_3$ |
| 1.321 | 2-((R)-3-fluoro-pyrrolidin-1-yl)-ethyl | —Br |
| 1.322 | 2-((R)-3-fluoro-pyrrolidin-1-yl)-ethyl | —F |
| 1.323 | 2-((R)-3-fluoro-pyrrolidin-1-yl)-ethyl | —OCH$_3$ |
| 1.324 | 2-((R)-3-fluoro-pyrrolidin-1-yl)-ethyl | —OCH$_2$CH$_3$ |
| 1.325 | 2-((R)-3-fluoro-pyrrolidin-1-yl)-ethyl | —Cl |
| 1.326 | 2-((R)-3-fluoro-pyrrolidin-1-yl)-ethyl | —OCH$_2$CH$_2$OCH$_3$ |
| 1.327 | 2-((R)-3-fluoro-pyrrolidin-1-yl)-ethyl | cyclopropylmethoxy |
| 1.328 | 2-((R)-3-fluoro-pyrrolidin-1-yl)-ethyl | trifluoromethyl |
| 1.329 | 2-((R)-3-fluoro-pyrrolidin-1-yl)-ethyl | difluoromethoxy |
| 1.330 | 2-((R)-3-fluoro-pyrrolidin-1-yl)-ethyl | trifluoromethoxy |
| 1.331 | 2-((S)-3-fluoro-pyrrolidin-1-yl)-ethyl | —CH$_3$ |
| 1.332 | 2-((S)-3-fluoro-pyrrolidin-1-yl)-ethyl | —Br |
| 1.333 | 2-((S)-3-fluoro-pyrrolidin-1-yl)-ethyl | —F |
| 1.334 | 2-((S)-3-fluoro-pyrrolidin-1-yl)-ethyl | —OCH$_3$ |
| 1.335 | 2-((S)-3-fluoro-pyrrolidin-1-yl)-ethyl | —OCH$_2$CH$_3$ |
| 1.336 | 2-((S)-3-fluoro-pyrrolidin-1-yl)-ethyl | —Cl |
| 1.337 | 2-((S)-3-fluoro-pyrrolidin-1-yl)-ethyl | —OCH$_2$CH$_2$OCH$_3$ |
| 1.338 | 2-((S)-3-fluoro-pyrrolidin-1-yl)-ethyl | cyclopropylmethoxy |
| 1.339 | 2-((S)-3-fluoro-pyrrolidin-1-yl)-ethyl | trifluoromethyl |
| 1.340 | 2-((S)-3-fluoro-pyrrolidin-1-yl)-ethyl | difluoromethoxy |
| 1.341 | 2-((S)-3-fluoro-pyrrolidin-1-yl)-ethyl | trifluoromethoxy |
| 1.342 | 2-(4-methyl-piperidin-1-yl)-ethyl | —CH$_3$ |
| 1.343 | 2-(4-methyl-piperidin-1-yl)-ethyl | —Br |
| 1.344 | 2-(4-methyl-piperidin-1-yl)-ethyl | —F |
| 1.345 | 2-(4-methyl-piperidin-1-yl)-ethyl | —OCH$_3$ |
| 1.346 | 2-(4-methyl-piperidin-1-yl)-ethyl | —OCH$_2$CH$_3$ |
| 1.347 | 2-(4-methyl-piperidin-1-yl)-ethyl | —Cl |
| 1.348 | 2-(4-methyl-piperidin-1-yl)-ethyl | —OCH$_2$CH$_2$OCH$_3$ |
| 1.349 | 2-(4-methyl-piperidin-1-yl)-ethyl | cyclopropylmethoxy |
| 1.350 | 2-(4-methyl-piperidin-1-yl)-ethyl | trifluoromethyl |
| 1.351 | 2-(4-methyl-piperidin-1-yl)-ethyl | difluoromethoxy |
| 1.352 | 2-(4-methyl-piperidin-1-yl)-ethyl | trifluoromethoxy |
| 1.353 | 3-(methylamino)-propyl | —CH$_3$ |
| 1.354 | 3-(methylamino)-propyl | —Br |
| 1.355 | 3-(methylamino)-propyl | —F |
| 1.356 | 3-(methylamino)-propyl | —OCH$_3$ |
| 1.357 | 3-(methylamino)-propyl | —OCH$_2$CH$_3$ |
| 1.358 | 3-(methylamino)-propyl | —Cl |
| 1.359 | 3-(methylamino)-propyl | —OCH$_2$CH$_2$OCH$_3$ |
| 1.360 | 3-(methylamino)-propyl | cyclopropylmethoxy |
| 1.361 | 3-(methylamino)-propyl | trifluoromethyl |
| 1.362 | 3-(methylamino)-propyl | difluoromethoxy |
| 1.363 | 3-(methylamino)-propyl | trifluoromethoxy |
| 1.364 | 3-(ethylamino)-propyl | —CH$_3$ |
| 1.365 | 3-(ethylamino)-propyl | —Br |
| 1.366 | 3-(ethylamino)-propyl | —F |
| 1.367 | 3-(ethylamino)-propyl | —OCH$_3$ |
| 1.368 | 3-(ethylamino)-propyl | —OCH$_2$CH$_3$ |
| 1.369 | 3-(ethylamino)-propyl | —Cl |
| 1.370 | 3-(ethylamino)-propyl | —OCH$_2$CH$_2$OCH$_3$ |
| 1.371 | 3-(ethylamino)-propyl | cyclopropylmethoxy |
| 1.372 | 3-(ethylamino)-propyl | trifluoromethyl |
| 1.373 | 3-(ethylamino)-propyl | difluoromethoxy |
| 1.374 | 3-(ethylamino)-propyl | trifluoromethoxy |
| 1.375 | 3-(azetidin-1-yl)-propyl | —CH$_3$ |
| 1.376 | 3-(azetidin-1-yl)-propyl | —Br |
| 1.377 | 3-(azetidin-1-yl)-propyl | —F |
| 1.378 | 3-(azetidin-1-yl)-propyl | —OCH$_3$ |
| 1.379 | 3-(azetidin-1-yl)-propyl | —OCH$_2$CH$_3$ |
| 1.380 | 3-(azetidin-1-yl)-propyl | —Cl |
| 1.381 | 3-(azetidin-1-yl)-propyl | —OCH$_2$CH$_2$OCH$_3$ |
| 1.382 | 3-(azetidin-1-yl)-propyl | cyclopropylmethoxy |
| 1.383 | 3-(azetidin-1-yl)-propyl | trifluoromethyl |
| 1.384 | 3-(azetidin-1-yl)-propyl | difluoromethoxy |
| 1.385 | 3-(azetidin-1-yl)-propyl | trifluoromethoxy |
| 1.386 | 3-(4-acetyl-piperazin-1-yl)-propyl | —CH$_3$ |
| 1.387 | 3-(4-acetyl-piperazin-1-yl)-propyl | —Br |
| 1.388 | 3-(4-acetyl-piperazin-1-yl)-propyl | —F |
| 1.389 | 3-(4-acetyl-piperazin-1-yl)-propyl | —OCH$_3$ |
| 1.390 | 3-(4-acetyl-piperazin-1-yl)-propyl | —OCH$_2$CH$_3$ |
| 1.391 | 3-(4-acetyl-piperazin-1-yl)-propyl | —Cl |
| 1.392 | 3-(4-acetyl-piperazin-1-yl)-propyl | —OCH$_2$CH$_2$OCH$_3$ |
| 1.393 | 3-(4-acetyl-piperazin-1-yl)-propyl | cyclopropylmethoxy |
| 1.394 | 3-(4-acetyl-piperazin-1-yl)-propyl | trifluoromethyl |
| 1.395 | 3-(4-acetyl-piperazin-1-yl)-propyl | difluoromethoxy |
| 1.396 | 3-(4-acetyl-piperazin-1-yl)-propyl | trifluoromethoxy |
| 1.397 | 3-(3,3-difluoropyrrolidin-1-yl)-propyl | —CH$_3$ |
| 1.398 | 3-(3,3-difluoropyrrolidin-1-yl)-propyl | —Br |
| 1.399 | 3-(3,3-difluoropyrrolidin-1-yl)-propyl | —F |
| 1.400 | 3-(3,3-difluoropyrrolidin-1-yl)-propyl | —OCH$_3$ |
| 1.401 | 3-(3,3-difluoropyrrolidin-1-yl)-propyl | —OCH$_2$CH$_3$ |
| 1.402 | 3-(3,3-difluoropyrrolidin-1-yl)-propyl | —Cl |
| 1.403 | 3-(3,3-difluoropyrrolidin-1-yl)-propyl | —OCH$_2$CH$_2$OCH$_3$ |
| 1.404 | 3-(3,3-difluoropyrrolidin-1-yl)-propyl | cyclopropylmethoxy |
| 1.405 | 3-(3,3-difluoropyrrolidin-1-yl)-propyl | trifluoromethyl |
| 1.406 | 3-(3,3-difluoropyrrolidin-1-yl)-propyl | difluoromethoxy |
| 1.407 | 3-(3,3-difluoropyrrolidin-1-yl)-propyl | trifluoromethoxy |
| 1.408 | 3-(2-fluoroethylamino)-propyl | —CH$_3$ |
| 1.409 | 3-(2-fluoroethylamino)-propyl | —Br |
| 1.410 | 3-(2-fluoroethylamino)-propyl | —F |
| 1.411 | 3-(2-fluoroethylamino)-propyl | —OCH$_3$ |
| 1.412 | 3-(2-fluoroethylamino)-propyl | —OCH$_2$CH$_3$ |
| 1.413 | 3-(2-fluoroethylamino)-propyl | —Cl |
| 1.414 | 3-(2-fluoroethylamino)-propyl | —OCH$_2$CH$_2$OCH$_3$ |
| 1.415 | 3-(2-fluoroethylamino)-propyl | cyclopropylmethoxy |
| 1.416 | 3-(2-fluoroethylamino)-propyl | trifluoromethyl |
| 1.417 | 3-(2-fluoroethylamino)-propyl | difluoromethoxy |
| 1.418 | 3-(2-fluoroethylamino)-propyl | trifluoromethoxy |
| 1.419 | 3-(2,2-difluoroethylamino)-propyl | —CH$_3$ |
| 1.420 | 3-(2,2-difluoroethylamino)-propyl | —Br |
| 1.421 | 3-(2,2-difluoroethylamino)-propyl | —F |
| 1.422 | 3-(2,2-difluoroethylamino)-propyl | —OCH$_3$ |
| 1.423 | 3-(2,2-difluoroethylamino)-propyl | —OCH$_2$CH$_3$ |
| 1.424 | 3-(2,2-difluoroethylamino)-propyl | —Cl |
| 1.425 | 3-(2,2-difluoroethylamino)-propyl | —OCH$_2$CH$_2$OCH$_3$ |
| 1.426 | 3-(2,2-difluoroethylamino)-propyl | cyclopropylmethoxy |
| 1.427 | 3-(2,2-difluoroethylamino)-propyl | trifluoromethyl |
| 1.428 | 3-(2,2-difluoroethylamino)-propyl | difluoromethoxy |
| 1.429 | 3-(2,2-difluoroethylamino)-propyl | trifluoromethoxy |
| 1.430 | 3-(2,2,2-trifluoroethylamino)-propyl | —CH$_3$ |
| 1.431 | 3-(2,2,2-trifluoroethylamino)-propyl | —Br |
| 1.432 | 3-(2,2,2-trifluoroethylamino)-propyl | —F |
| 1.433 | 3-(2,2,2-trifluoroethylamino)-propyl | —OCH$_3$ |
| 1.434 | 3-(2,2,2-trifluoroethylamino)-propyl | —OCH$_2$CH$_3$ |
| 1.435 | 3-(2,2,2-trifluoroethylamino)-propyl | —Cl |
| 1.436 | 3-(2,2,2-trifluoroethylamino)-propyl | —OCH$_2$CH$_2$OCH$_3$ |
| 1.437 | 3-(2,2,2-trifluoroethylamino)-propyl | cyclopropylmethoxy |
| 1.438 | 3-(2,2,2-trifluoroethylamino)-propyl | trifluoromethyl |
| 1.439 | 3-(2,2,2-trifluoroethylamino)-propyl | difluoromethoxy |
| 1.440 | 3-(2,2,2-trifluoroethylamino)-propyl | trifluoromethoxy |
| 1.441 | 3-(isopropylamino)-propyl | —CH$_3$ |
| 1.442 | 3-(isopropylamino)-propyl | —Br |
| 1.443 | 3-(isopropylamino)-propyl | —F |
| 1.444 | 3-(isopropylamino)-propyl | —OCH$_3$ |
| 1.445 | 3-(isopropylamino)-propyl | —OCH$_2$CH$_3$ |
| 1.446 | 3-(isopropylamino)-propyl | —Cl |
| 1.447 | 3-(isopropylamino)-propyl | —OCH$_2$CH$_2$OCH$_3$ |
| 1.448 | 3-(isopropylamino)-propyl | cyclopropylmethoxy |
| 1.449 | 3-(isopropylamino)-propyl | trifluoromethyl |
| 1.450 | 3-(isopropylamino)-propyl | difluoromethoxy |
| 1.451 | 3-(isopropylamino)-propyl | trifluoromethoxy |
| 1.452 | 3-(isobutylamino)-propyl | —CH$_3$ |
| 1.453 | 3-(isobutylamino)-propyl | —Br |
| 1.454 | 3-(isobutylamino)-propyl | —F |
| 1.455 | 3-(isobutylamino)-propyl | —OCH$_3$ |
| 1.456 | 3-(isobutylamino)-propyl | —OCH$_2$CH$_3$ |
| 1.457 | 3-(isobutylamino)-propyl | —Cl |
| 1.458 | 3-(isobutylamino)-propyl | —OCH$_2$CH$_2$OCH$_3$ |
| 1.459 | 3-(isobutylamino)-propyl | cyclopropylmethoxy |
| 1.460 | 3-(isobutylamino)-propyl | trifluoromethyl |
| 1.461 | 3-(isobutylamino)-propyl | difluoromethoxy |
| 1.462 | 3-(isobutylamino)-propyl | trifluoromethoxy |
| 1.463 | 3-(N-cyclopropylmethyl-amino)-propyl | —CH$_3$ |

TABLE 1-continued

| No. | R1 | R5 |
|---|---|---|
| 1.464 | 3-(N-cyclopropylmethyl-amino)-propyl | —Br |
| 1.465 | 3-(N-cyclopropylmethyl-amino)-propyl | —F |
| 1.466 | 3-(N-cyclopropylmethyl-amino)-propyl | —OCH$_3$ |
| 1.467 | 3-(N-cyclopropylmethyl-amino)-propyl | —OCH$_2$CH$_3$ |
| 1.468 | 3-(N-cyclopropylmethyl-amino)-propyl | —Cl |
| 1.469 | 3-(N-cyclopropylmethyl-amino)-propyl | —OCH$_2$CH$_2$OCH$_3$ |
| 1.470 | 3-(N-cyclopropylmethyl-amino)-propyl | cyclopropylmethoxy |
| 1.471 | 3-(N-cyclopropylmethyl-amino)-propyl | trifluoromethyl |
| 1.472 | 3-(N-cyclopropylmethyl-amino)-propyl | difluoromethoxy |
| 1.473 | 3-(N-cyclopropylmethyl-amino)-propyl | trifluoromethoxy |
| 1.474 | 3-(cyclopropylamino)-propyl | —CH$_3$ |
| 1.475 | 3-(cyclopropylamino)-propyl | —Br |
| 1.476 | 3-(cyclopropylamino)-propyl | —F |
| 1.477 | 3-(cyclopropylamino)-propyl | —OCH$_3$ |
| 1.478 | 3-(cyclopropylamino)-propyl | —OCH$_2$CH$_3$ |
| 1.479 | 3-(cyclopropylamino)-propyl | —Cl |
| 1.480 | 3-(cyclopropylamino)-propyl | —OCH$_2$CH$_2$OCH$_3$ |
| 1.481 | 3-(cyclopropylamino)-propyl | cyclopropylmethoxy |
| 1.482 | 3-(cyclopropylamino)-propyl | trifluoromethyl |
| 1.483 | 3-(cyclopropylamino)-propyl | difluoromethoxy |
| 1.484 | 3-(cyclopropylamino)-propyl | trifluoromethoxy |
| 1.485 | 3-(cyclobutylamino)-propyl | —CH$_3$ |
| 1.486 | 3-(cyclobutylamino)-propyl | —Br |
| 1.487 | 3-(cyclobutylamino)-propyl | —F |
| 1.488 | 3-(cyclobutylamino)-propyl | —OCH$_3$ |
| 1.489 | 3-(cyclobutylamino)-propyl | —OCH$_2$CH$_3$ |
| 1.490 | 3-(cyclobutylamino)-propyl | —Cl |
| 1.491 | 3-(cyclobutylamino)-propyl | —OCH$_2$CH$_2$OCH$_3$ |
| 1.492 | 3-(cyclobutylamino)-propyl | cyclopropylmethoxy |
| 1.493 | 3-(cyclobutylamino)-propyl | trifluoromethyl |
| 1.494 | 3-(cyclobutylamino)-propyl | difluoromethoxy |
| 1.495 | 3-(cyclobutylamino)-propyl | trifluoromethoxy |
| 1.496 | 3-(N-ethyl-N-methyl-amino)-propyl | —CH$_3$ |
| 1.497 | 3-(N-ethyl-N-methyl-amino)-propyl | —Br |
| 1.498 | 3-(N-ethyl-N-methyl-amino)-propyl | —F |
| 1.499 | 3-(N-ethyl-N-methyl-amino)-propyl | —OCH$_3$ |
| 1.500 | 3-(N-ethyl-N-methyl-amino)-propyl | —OCH$_2$CH$_3$ |
| 1.501 | 3-(N-ethyl-N-methyl-amino)-propyl | —Cl |
| 1.502 | 3-(N-ethyl-N-methyl-amino)-propyl | —OCH$_2$CH$_2$OCH$_3$ |
| 1.503 | 3-(N-ethyl-N-methyl-amino)-propyl | cyclopropylmethoxy |
| 1.504 | 3-(N-ethyl-N-methyl-amino)-propyl | trifluoromethyl |
| 1.505 | 3-(N-ethyl-N-methyl-amino)-propyl | difluoromethoxy |
| 1.506 | 3-(N-ethyl-N-methyl-amino)-propyl | trifluoromethoxy |
| 1.507 | 3-(diethylamino)-propyl | —CH$_3$ |
| 1.508 | 3-(diethylamino)-propyl | —Br |
| 1.509 | 3-(diethylamino)-propyl | —F |
| 1.510 | 3-(diethylamino)-propyl | —OCH$_3$ |
| 1.511 | 3-(diethylamino)-propyl | —OCH$_2$CH$_3$ |
| 1.512 | 3-(diethylamino)-propyl | —Cl |
| 1.513 | 3-(diethylamino)-propyl | —OCH$_2$CH$_2$OCH$_3$ |
| 1.514 | 3-(diethylamino)-propyl | cyclopropylmethoxy |
| 1.515 | 3-(diethylamino)-propyl | trifluoromethyl |
| 1.516 | 3-(diethylamino)-propyl | difluoromethoxy |
| 1.517 | 3-(diethylamino)-propyl | trifluoromethoxy |
| 1.518 | 3-(N-isopropyl-N-methyl-amino)-propyl | —CH$_3$ |
| 1.519 | 3-(N-isopropyl-N-methyl-amino)-propyl | —Br |
| 1.520 | 3-(N-isopropyl-N-methyl-amino)-propyl | —F |
| 1.521 | 3-(N-isopropyl-N-methyl-amino)-propyl | —OCH$_3$ |
| 1.522 | 3-(N-isopropyl-N-methyl-amino)-propyl | —OCH$_2$CH$_3$ |
| 1.523 | 3-(N-isopropyl-N-methyl-amino)-propyl | —Cl |
| 1.524 | 3-(N-isopropyl-N-methyl-amino)-propyl | —OCH$_2$CH$_2$OCH$_3$ |
| 1.525 | 3-(N-isopropyl-N-methyl-amino)-propyl | cyclopropylmethoxy |
| 1.526 | 3-(N-isopropyl-N-methyl-amino)-propyl | trifluoromethyl |
| 1.527 | 3-(N-isopropyl-N-methyl-amino)-propyl | difluoromethoxy |
| 1.528 | 3-(N-isopropyl-N-methyl-amino)-propyl | trifluoromethoxy |
| 1.529 | 3-((R)-3-fluoro-pyrrolidin-1-yl)-propyl | —CH$_3$ |
| 1.530 | 3-((R)-3-fluoro-pyrrolidin-1-yl)-propyl | —Br |
| 1.531 | 3-((R)-3-fluoro-pyrrolidin-1-yl)-propyl | —F |
| 1.532 | 3-((R)-3-fluoro-pyrrolidin-1-yl)-propyl | —OCH$_3$ |
| 1.533 | 3-((R)-3-fluoro-pyrrolidin-1-yl)-propyl | —OCH$_2$CH$_3$ |
| 1.534 | 3-((R)-3-fluoro-pyrrolidin-1-yl)-propyl | —Cl |
| 1.535 | 3-((R)-3-fluoro-pyrrolidin-1-yl)-propyl | —OCH$_2$CH$_2$OCH$_3$ |
| 1.536 | 3-((R)-3-fluoro-pyrrolidin-1-yl)-propyl | cyclopropylmethoxy |
| 1.537 | 3-((R)-3-fluoro-pyrrolidin-1-yl)-propyl | trifluoromethyl |
| 1.538 | 3-((R)-3-fluoro-pyrrolidin-1-yl)-propyl | difluoromethoxy |
| 1.539 | 3-((R)-3-fluoro-pyrrolidin-1-yl)-propyl | trifluoromethoxy |
| 1.540 | 3-((S)-3-fluoro-pyrrolidin-1-yl)-propyl | —CH$_3$ |
| 1.541 | 3-((S)-3-fluoro-pyrrolidin-1-yl)-propyl | —Br |
| 1.542 | 3-((S)-3-fluoro-pyrrolidin-1-yl)-propyl | —F |
| 1.543 | 3-((S)-3-fluoro-pyrrolidin-1-yl)-propyl | —OCH$_3$ |
| 1.544 | 3-((S)-3-fluoro-pyrrolidin-1-yl)-propyl | —OCH$_2$CH$_3$ |
| 1.545 | 3-((S)-3-fluoro-pyrrolidin-1-yl)-propyl | —Cl |
| 1.546 | 3-((S)-3-fluoro-pyrrolidin-1-yl)-propyl | —OCH$_2$CH$_2$OCH$_3$ |
| 1.547 | 3-((S)-3-fluoro-pyrrolidin-1-yl)-propyl | cyclopropylmethoxy |
| 1.548 | 3-((S)-3-fluoro-pyrrolidin-1-yl)-propyl | trifluoromethyl |
| 1.549 | 3-((S)-3-fluoro-pyrrolidin-1-yl)-propyl | difluoromethoxy |
| 1.550 | 3-((S)-3-fluoro-pyrrolidin-1-yl)-propyl | trifluoromethoxy |
| 1.551 | 3-(4-methyl-piperidin-1-yl)-propyl | —CH$_3$ |
| 1.552 | 3-(4-methyl-piperidin-1-yl)-propyl | —Br |
| 1.553 | 3-(4-methyl-piperidin-1-yl)-propyl | —F |
| 1.554 | 3-(4-methyl-piperidin-1-yl)-propyl | —OCH$_3$ |
| 1.555 | 3-(4-methyl-piperidin-1-yl)-propyl | —OCH$_2$CH$_3$ |
| 1.556 | 3-(4-methyl-piperidin-1-yl)-propyl | —Cl |
| 1.557 | 3-(4-methyl-piperidin-1-yl)-propyl | —OCH$_2$CH$_2$OCH$_3$ |
| 1.558 | 3-(4-methyl-piperidin-1-yl)-propyl | cyclopropylmethoxy |
| 1.559 | 3-(4-methyl-piperidin-1-yl)-propyl | trifluoromethyl |
| 1.560 | 3-(4-methyl-piperidin-1-yl)-propyl | difluoromethoxy |
| 1.561 | 3-(4-methyl-piperidin-1-yl)-propyl | trifluoromethoxy |
| 1.562 | 3-[N-(2-hydroxyethyl)-amino]-propyl | —CH$_3$ |
| 1.563 | 3-[N-(2-hydroxyethyl)-amino]-propyl | —Br |
| 1.564 | 3-[N-(2-hydroxyethyl)-amino]-propyl | —F |
| 1.565 | 3-[N-(2-hydroxyethyl)-amino]-propyl | —OCH$_3$ |
| 1.566 | 3-[N-(2-hydroxyethyl)-amino]-propyl | —OCH$_2$CH$_3$ |
| 1.567 | 3-[N-(2-hydroxyethyl)-amino]-propyl | —Cl |
| 1.568 | 3-[N-(2-hydroxyethyl)-amino]-propyl | —OCH$_2$CH$_2$OCH$_3$ |
| 1.569 | 3-[N-(2-hydroxyethyl)-amino]-propyl | cyclopropylmethoxy |
| 1.570 | 3-[N-(2-hydroxyethyl)-amino]-propyl | trifluoromethyl |
| 1.571 | 3-[N-(2-hydroxyethyl)-amino]-propyl | difluoromethoxy |
| 1.572 | 3-[N-(2-hydroxyethyl)-amino]-propyl | trifluoromethoxy |
| 1.573 | 3-[N-(2-methoxyethyl)-amino]-propyl | —CH$_3$ |
| 1.574 | 3-[N-(2-methoxyethyl)-amino]-propyl | —Br |
| 1.575 | 3-[N-(2-methoxyethyl)-amino]-propyl | —F |
| 1.576 | 3-[N-(2-methoxyethyl)-amino]-propyl | —OCH$_3$ |
| 1.577 | 3-[N-(2-methoxyethyl)-amino]-propyl | —OCH$_2$CH$_3$ |
| 1.578 | 3-[N-(2-methoxyethyl)-amino]-propyl | —Cl |
| 1.579 | 3-[N-(2-methoxyethyl)-amino]-propyl | —OCH$_2$CH$_2$OCH$_3$ |
| 1.580 | 3-[N-(2-methoxyethyl)-amino]-propyl | cyclopropylmethoxy |
| 1.581 | 3-[N-(2-methoxyethyl)-amino]-propyl | trifluoromethyl |
| 1.582 | 3-[N-(2-methoxyethyl)-amino]-propyl | difluoromethoxy |
| 1.583 | 3-[N-(2-methoxyethyl)-amino]-propyl | trifluoromethoxy |
| 1.584 | 3-(tertbutylamino)-propyl | —CH$_3$ |
| 1.585 | 3-(tertbutylamino)-propyl | —Br |
| 1.586 | 3-(tertbutylamino)-propyl | —F |
| 1.587 | 3-(tertbutylamino)-propyl | —OCH$_3$ |
| 1.588 | 3-(tertbutylamino)-propyl | —OCH$_2$CH$_3$ |
| 1.589 | 3-(tertbutylamino)-propyl | —Cl |
| 1.590 | 3-(tertbutylamino)-propyl | —OCH$_2$CH$_2$OCH$_3$ |
| 1.591 | 3-(tertbutylamino)-propyl | cyclopropylmethoxy |
| 1.592 | 3-(tertbutylamino)-propyl | trifluoromethyl |
| 1.593 | 3-(tertbutylamino)-propyl | difluoromethoxy |
| 1.594 | 3-(tertbutylamino)-propyl | trifluoromethoxy |
| 1.595 | 3-(allylamino)-propyl | —CH$_3$ |
| 1.596 | 3-(allylamino)-propyl | —Br |
| 1.597 | 3-(allylamino)-propyl | —F |
| 1.598 | 3-(allylamino)-propyl | —OCH$_3$ |

TABLE 1-continued

| No. | R1 | R5 |
|---|---|---|
| 1.599 | 3-(allylamino)-propyl | —OCH₂CH₃ |
| 1.600 | 3-(allylamino)-propyl | —Cl |
| 1.601 | 3-(allylamino)-propyl | —OCH₂CH₂OCH₃ |
| 1.602 | 3-(allylamino)-propyl | cyclopropylmethoxy |
| 1.603 | 3-(allylamino)-propyl | trifluoromethyl |
| 1.604 | 3-(allylamino)-propyl | difluoromethoxy |
| 1.605 | 3-(allylamino)-propyl | trifluoromethoxy |
| 1.606 | 3-(propargylamino)-propyl | —CH₃ |
| 1.607 | 3-(propargylamino)-propyl | —Br |
| 1.608 | 3-(propargylamino)-propyl | —F |
| 1.609 | 3-(propargylamino)-propyl | —OCH₃ |
| 1.610 | 3-(propargylamino)-propyl | —OCH₂CH₃ |
| 1.611 | 3-(propargylamino)-propyl | —Cl |
| 1.612 | 3-(propargylamino)-propyl | —OCH₂CH₂OCH₃ |
| 1.613 | 3-(propargylamino)-propyl | cyclopropylmethoxy |
| 1.614 | 3-(propargylamino)-propyl | trifluoromethyl |
| 1.615 | 3-(propargylamino)-propyl | difluoromethoxy |
| 1.616 | 3-(propargylamino)-propyl | trifluoromethoxy |
| 1.617 | 3-(N-allyl-N-methyl-amino)-propyl | —CH₃ |
| 1.618 | 3-(N-allyl-N-methyl-amino)-propyl | —Br |
| 1.619 | 3-(N-allyl-N-methyl-amino)-propyl | —F |
| 1.620 | 3-(N-allyl-N-methyl-amino)-propyl | —OCH₃ |
| 1.621 | 3-(N-allyl-N-methyl-amino)-propyl | —OCH₂CH₃ |
| 1.622 | 3-(N-allyl-N-methyl-amino)-propyl | —Cl |
| 1.623 | 3-(N-allyl-N-methyl-amino)-propyl | —OCH₂CH₂OCH₃ |
| 1.624 | 3-(N-allyl-N-methyl-amino)-propyl | cyclopropylmethoxy |
| 1.625 | 3-(N-allyl-N-methyl-amino)-propyl | trifluoromethyl |
| 1.626 | 3-(N-allyl-N-methyl-amino)-propyl | difluoromethoxy |
| 1.627 | 3-(N-allyl-N-methyl-amino)-propyl | trifluoromethoxy |
| 1.628 | 3-(N-methyl-N-propargyl-amino)-propyl | —CH₃ |
| 1.629 | 3-(N-methyl-N-propargyl-amino)-propyl | —Br |
| 1.630 | 3-(N-methyl-N-propargyl-amino)-propyl | —F |
| 1.631 | 3-(N-methyl-N-propargyl-amino)-propyl | —OCH₃ |
| 1.632 | 3-(N-methyl-N-propargyl-amino)-propyl | —OCH₂CH₃ |
| 1.633 | 3-(N-methyl-N-propargyl-amino)-propyl | —Cl |
| 1.634 | 3-(N-methyl-N-propargyl-amino)-propyl | —OCH₂CH₂OCH₃ |
| 1.635 | 3-(N-methyl-N-propargyl-amino)-propyl | cyclopropylmethoxy |
| 1.636 | 3-(N-methyl-N-propargyl-amino)-propyl | trifluoromethyl |
| 1.637 | 3-(N-methyl-N-propargyl-amino)-propyl | difluoromethoxy |
| 1.638 | 3-(N-methyl-N-propargyl-amino)-propyl | trifluoromethoxy |
| 1.639 | 3-[N-(2-hydroxyethyl)-N-methyl-amino]-propyl | —CH₃ |
| 1.640 | 3-[N-(2-hydroxyethyl)-N-methyl-amino]-propyl | —Br |
| 1.641 | 3-[N-(2-hydroxyethyl)-N-methyl-amino]-propyl | —F |
| 1.642 | 3-[N-(2-hydroxyethyl)-N-methyl-amino]-propyl | —OCH₃ |
| 1.643 | 3-[N-(2-hydroxyethyl)-N-methyl-amino]-propyl | —OCH₂CH₃ |
| 1.644 | 3-[N-(2-hydroxyethyl)-N-methyl-amino]-propyl | —Cl |
| 1.645 | 3-[N-(2-hydroxyethyl)-N-methyl-amino]-propyl | —OCH₂CH₂OCH₃ |
| 1.646 | 3-[N-(2-hydroxyethyl)-N-methyl-amino]-propyl | cyclopropylmethoxy |
| 1.647 | 3-[N-(2-hydroxyethyl)-N-methyl-amino]-propyl | trifluoromethyl |
| 1.648 | 3-[N-(2-hydroxyethyl)-N-methyl-amino]-propyl | difluoromethoxy |
| 1.649 | 3-[N-(2-hydroxyethyl)-N-methyl-amino]-propyl | trifluoromethoxy |
| 1.650 | 3-[N-(2-methoxyethyl)-N-methyl-amino]-propyl | —CH₃ |
| 1.651 | 3-[N-(2-methoxyethyl)-N-methyl-amino]-propyl | —Br |
| 1.652 | 3-[N-(2-methoxyethyl)-N-methyl-amino]-propyl | —F |
| 1.653 | 3-[N-(2-methoxyethyl)-N-methyl-amino]-propyl | —OCH₃ |
| 1.654 | 3-[N-(2-methoxyethyl)-N-methyl-amino]-propyl | —OCH₂CH₃ |
| 1.655 | 3-[N-(2-methoxyethyl)-N-methyl-amino]-propyl | —Cl |
| 1.656 | 3-[N-(2-methoxyethyl)-N-methyl-amino]-propyl | —OCH₂CH₂OCH₃ |
| 1.657 | 3-[N-(2-methoxyethyl)-N-methyl-amino]-propyl | cyclopropylmethoxy |
| 1.658 | 3-[N-(2-methoxyethyl)-N-methyl-amino]-propyl | trifluoromethyl |
| 1.659 | 3-[N-(2-methoxyethyl)-N-methyl-amino]-propyl | difluoromethoxy |
| 1.660 | 3-[N-(2-methoxyethyl)-N-methyl-amino]-propyl | trifluoromethoxy |
| 1.661 | 3-[N-ethyl-N-(2-hydroxyethyl)-amino]-propyl | —CH₃ |
| 1.662 | 3-[N-ethyl-N-(2-hydroxyethyl)-amino]-propyl | —Br |
| 1.663 | 3-[N-ethyl-N-(2-hydroxyethyl)-amino]-propyl | —F |
| 1.664 | 3-[N-ethyl-N-(2-hydroxyethyl)-amino]-propyl | —OCH₃ |
| 1.665 | 3-[N-ethyl-N-(2-hydroxyethyl)-amino]-propyl | —OCH₂CH₃ |
| 1.666 | 3-[N-ethyl-N-(2-hydroxyethyl)-amino]-propyl | —Cl |
| 1.667 | 3-[N-ethyl-N-(2-hydroxyethyl)-amino]-propyl | —OCH₂CH₂OCH₃ |
| 1.668 | 3-[N-ethyl-N-(2-hydroxyethyl)-amino]-propyl | cyclopropylmethoxy |
| 1.669 | 3-[N-ethyl-N-(2-hydroxyethyl)-amino]-propyl | trifluoromethyl |
| 1.670 | 3-[N-ethyl-N-(2-hydroxyethyl)-amino]-propyl | difluoromethoxy |
| 1.671 | 3-[N-ethyl-N-(2-hydroxyethyl)-amino]-propyl | trifluoromethoxy |
| 1.672 | 3-[N-ethyl-N-(2-methoxyethyl)-amino]-propyl | —CH₃ |
| 1.673 | 3-[N-ethyl-N-(2-methoxyethyl)-amino]-propyl | —Br |
| 1.674 | 3-[N-ethyl-N-(2-methoxyethyl)-amino]-propyl | —F |
| 1.675 | 3-[N-ethyl-N-(2-methoxyethyl)-amino]-propyl | —OCH₃ |
| 1.676 | 3-[N-ethyl-N-(2-methoxyethyl)-amino]-propyl | —OCH₂CH₃ |
| 1.677 | 3-[N-ethyl-N-(2-methoxyethyl)-amino]-propyl | —Cl |
| 1.678 | 3-[N-ethyl-N-(2-methoxyethyl)-amino]-propyl | —OCH₂CH₂OCH₃ |
| 1.679 | 3-[N-ethyl-N-(2-methoxyethyl)-amino]-propyl | cyclopropylmethoxy |
| 1.680 | 3-[N-ethyl-N-(2-methoxyethyl)-amino]-propyl | trifluoromethyl |
| 1.681 | 3-[N-ethyl-N-(2-methoxyethyl)-amino]-propyl | difluoromethoxy |
| 1.682 | 3-[N-ethyl-N-(2-methoxyethyl)-amino]-propyl | trifluoromethoxy |
| 1.683 | 3-(piperidin-1-yl)-propyl | —CH₃ |
| 1.684 | 3-(piperidin-1-yl)-propyl | —Br |
| 1.685 | 3-(piperidin-1-yl)-propyl | —F |
| 1.686 | 3-(piperidin-1-yl)-propyl | —OCH₃ |
| 1.687 | 3-(piperidin-1-yl)-propyl | —OCH₂CH₃ |
| 1.688 | 3-(piperidin-1-yl)-propyl | —Cl |
| 1.689 | 3-(piperidin-1-yl)-propyl | —OCH₂CH₂OCH₃ |
| 1.690 | 3-(piperidin-1-yl)-propyl | cyclopropylmethoxy |
| 1.691 | 3-(piperidin-1-yl)-propyl | trifluoromethyl |
| 1.692 | 3-(piperidin-1-yl)-propyl | difluoromethoxy |
| 1.693 | 3-(piperidin-1-yl)-propyl | trifluoromethoxy |
| 1.694 | 3-(homopiperidin-1-yl)-propyl | —CH₃ |
| 1.695 | 3-(homopiperidin-1-yl)-propyl | —Br |
| 1.696 | 3-(homopiperidin-1-yl)-propyl | —F |
| 1.697 | 3-(homopiperidin-1-yl)-propyl | —OCH₃ |
| 1.698 | 3-(homopiperidin-1-yl)-propyl | —OCH₂CH₃ |

TABLE 1-continued

| No. | R1 | R5 |
|---|---|---|
| 1.699 | 3-(homopiperidin-1-yl)-propyl | —Cl |
| 1.700 | 3-(homopiperidin-1-yl)-propyl | —OCH$_2$CH$_2$OCH$_3$ |
| 1.701 | 3-(homopiperidin-1-yl)-propyl | cyclopropylmethoxy |
| 1.702 | 3-(homopiperidin-1-yl)-propyl | trifluoromethyl |
| 1.703 | 3-(homopiperidin-1-yl)-propyl | difluoromethoxy |
| 1.704 | 3-(homopiperidin-1-yl)-propyl | trifluoromethoxy |
| 1.705 | 3-(2,5-dihydropyrrol-1-yl)-propyl | —CH$_3$ |
| 1.706 | 3-(2,5-dihydropyrrol-1-yl)-propyl | —Br |
| 1.707 | 3-(2,5-dihydropyrrol-1-yl)-propyl | —F |
| 1.708 | 3-(2,5-dihydropyrrol-1-yl)-propyl | —OCH$_3$ |
| 1.709 | 3-(2,5-dihydropyrrol-1-yl)-propyl | —OCH$_2$CH$_3$ |
| 1.710 | 3-(2,5-dihydropyrrol-1-yl)-propyl | —Cl |
| 1.711 | 3-(2,5-dihydropyrrol-1-yl)-propyl | —OCH$_2$CH$_2$OCH$_3$ |
| 1.712 | 3-(2,5-dihydropyrrol-1-yl)-propyl | cyclopropylmethoxy |
| 1.713 | 3-(2,5-dihydropyrrol-1-yl)-propyl | trifluoromethyl |
| 1.714 | 3-(2,5-dihydropyrrol-1-yl)-propyl | difluoromethoxy |
| 1.715 | 3-(2,5-dihydropyrrol-1-yl)-propyl | trifluoromethoxy |
| 1.716 | 3-(1,2,3,6-tetrahydropyridin-1-yl)-propyl | —CH$_3$ |
| 1.717 | 3-(1,2,3,6-tetrahydropyridin-1-yl)-propyl | —Br |
| 1.718 | 3-(1,2,3,6-tetrahydropyridin-1-yl)-propyl | —F |
| 1.719 | 3-(1,2,3,6-tetrahydropyridin-1-yl)-propyl | —OCH$_3$ |
| 1.720 | 3-(1,2,3,6-tetrahydropyridin-1-yl)-propyl | —OCH$_2$CH$_3$ |
| 1.721 | 3-(1,2,3,6-tetrahydropyridin-1-yl)-propyl | —Cl |
| 1.722 | 3-(1,2,3,6-tetrahydropyridin-1-yl)-propyl | —OCH$_2$CH$_2$OCH$_3$ |
| 1.723 | 3-(1,2,3,6-tetrahydropyridin-1-yl)-propyl | cyclopropylmethoxy |
| 1.724 | 3-(1,2,3,6-tetrahydropyridin-1-yl)-propyl | trifluoromethyl |
| 1.725 | 3-(1,2,3,6-tetrahydropyridin-1-yl)-propyl | difluoromethoxy |
| 1.726 | 3-(1,2,3,6-tetrahydropyridin-1-yl)-propyl | trifluoromethoxy |
| 1.727 | 2-[N-(2-hydroxyethyl)-amino]-ethyl | —CH$_3$ |
| 1.728 | 2-[N-(2-hydroxyethyl)-amino]-ethyl | —Br |
| 1.729 | 2-[N-(2-hydroxyethyl)-amino]-ethyl | —F |
| 1.730 | 2-[N-(2-hydroxyethyl)-amino]-ethyl | —OCH$_3$ |
| 1.731 | 2-[N-(2-hydroxyethyl)-amino]-ethyl | —OCH$_2$CH$_3$ |
| 1.732 | 2-[N-(2-hydroxyethyl)-amino]-ethyl | —Cl |
| 1.733 | 2-[N-(2-hydroxyethyl)-amino]-ethyl | —OCH$_2$CH$_2$OCH$_3$ |
| 1.734 | 2-[N-(2-hydroxyethyl)-amino]-ethyl | cyclopropylmethoxy |
| 1.735 | 2-[N-(2-hydroxyethyl)-amino]-ethyl | trifluoromethyl |
| 1.736 | 2-[N-(2-hydroxyethyl)-amino]-ethyl | difluoromethoxy |
| 1.737 | 2-[N-(2-hydroxyethyl)-amino]-ethyl | trifluoromethoxy |
| 1.738 | 2-[N-(2-methoxyethyl)-amino]-ethyl | —CH$_3$ |
| 1.739 | 2-[N-(2-methoxyethyl)-amino]-ethyl | —Br |
| 1.740 | 2-[N-(2-methoxyethyl)-amino]-ethyl | —F |
| 1.741 | 2-[N-(2-methoxyethyl)-amino]-ethyl | —OCH$_3$ |
| 1.742 | 2-[N-(2-methoxyethyl)-amino]-ethyl | —OCH$_2$CH$_3$ |
| 1.743 | 2-[N-(2-methoxyethyl)-amino]-ethyl | —Cl |
| 1.744 | 2-[N-(2-methoxyethyl)-amino]-ethyl | —OCH$_2$CH$_2$OCH$_3$ |
| 1.745 | 2-[N-(2-methoxyethyl)-amino]-ethyl | cyclopropylmethoxy |
| 1.746 | 2-[N-(2-methoxyethyl)-amino]-ethyl | trifluoromethyl |
| 1.747 | 2-[N-(2-methoxyethyl)-amino]-ethyl | difluoromethoxy |
| 1.748 | 2-[N-(2-methoxyethyl)-amino]-ethyl | trifluoromethoxy |
| 1.749 | 2-(tertbutylamino)-ethyl | —CH$_3$ |
| 1.750 | 2-(tertbutylamino)-ethyl | —Br |
| 1.751 | 2-(tertbutylamino)-ethyl | —F |
| 1.752 | 2-(tertbutylamino)-ethyl | —OCH$_3$ |
| 1.753 | 2-(tertbutylamino)-ethyl | —OCH$_2$CH$_3$ |
| 1.754 | 2-(tertbutylamino)-ethyl | —Cl |
| 1.755 | 2-(tertbutylamino)-ethyl | —OCH$_2$CH$_2$OCH$_3$ |
| 1.756 | 2-(tertbutylamino)-ethyl | cyclopropylmethoxy |
| 1.757 | 2-(tertbutylamino)-ethyl | trifluoromethyl |
| 1.758 | 2-(tertbutylamino)-ethyl | difluoromethoxy |
| 1.759 | 2-(tertbutylamino)-ethyl | trifluoromethoxy |
| 1.760 | 2-(allylamino)-ethyl | —CH$_3$ |
| 1.761 | 2-(allylamino)-ethyl | —Br |
| 1.762 | 2-(allylamino)-ethyl | —F |
| 1.763 | 2-(allylamino)-ethyl | —OCH$_3$ |
| 1.764 | 2-(allylamino)-ethyl | —OCH$_2$CH$_3$ |
| 1.765 | 2-(allylamino)-ethyl | —Cl |
| 1.766 | 2-(allylamino)-ethyl | —OCH$_2$CH$_2$OCH$_3$ |
| 1.767 | 2-(allylamino)-ethyl | cyclopropylmethoxy |
| 1.768 | 2-(allylamino)-ethyl | trifluoromethyl |
| 1.769 | 2-(allylamino)-ethyl | difluoromethoxy |
| 1.770 | 2-(allylamino)-ethyl | trifluoromethoxy |
| 1.771 | 2-(propargylamino)-ethyl | —CH$_3$ |
| 1.772 | 2-(propargylamino)-ethyl | —Br |
| 1.773 | 2-(propargylamino)-ethyl | —F |
| 1.774 | 2-(propargylamino)-ethyl | —OCH$_3$ |
| 1.775 | 2-(propargylamino)-ethyl | —OCH$_2$CH$_3$ |
| 1.776 | 2-(propargylamino)-ethyl | —Cl |
| 1.777 | 2-(propargylamino)-ethyl | —OCH$_2$CH$_2$OCH$_3$ |
| 1.778 | 2-(propargylamino)-ethyl | cyclopropylmethoxy |
| 1.779 | 2-(propargylamino)-ethyl | trifluoromethyl |
| 1.780 | 2-(propargylamino)-ethyl | difluoromethoxy |
| 1.781 | 2-(propargylamino)-ethyl | trifluoromethoxy |
| 1.782 | 2-(N-allyl-N-methyl-amino)-ethyl | —CH$_3$ |
| 1.783 | 2-(N-allyl-N-methyl-amino)-ethyl | —Br |
| 1.784 | 2-(N-allyl-N-methyl-amino)-ethyl | —F |
| 1.785 | 2-(N-allyl-N-methyl-amino)-ethyl | —OCH$_3$ |
| 1.786 | 2-(N-allyl-N-methyl-amino)-ethyl | —OCH$_2$CH$_3$ |
| 1.787 | 2-(N-allyl-N-methyl-amino)-ethyl | —Cl |
| 1.788 | 2-(N-allyl-N-methyl-amino)-ethyl | —OCH$_2$CH$_2$OCH$_3$ |
| 1.789 | 2-(N-allyl-N-methyl-amino)-ethyl | cyclopropylmethoxy |
| 1.790 | 2-(N-allyl-N-methyl-amino)-ethyl | trifluoromethyl |
| 1.791 | 2-(N-allyl-N-methyl-amino)-ethyl | difluoromethoxy |
| 1.792 | 2-(N-allyl-N-methyl-amino)-ethyl | trifluoromethoxy |
| 1.793 | 2-(N-methyl-N-propargyl-amino)-ethyl | —CH$_3$ |
| 1.794 | 2-(N-ethyl-N-propargyl-amino)-ethyl | —Br |
| 1.795 | 2-(N-methyl-N-propargyl-amino)-ethyl | —F |
| 1.796 | 2-(N-methyl-N-propargyl-amino)-ethyl | —OCH$_3$ |
| 1.797 | 2-(N-methyl-N-propargyl-amino)-ethyl | —OCH$_2$CH$_3$ |
| 1.798 | 2-(N-methyl-N-propargyl-amino)-ethyl | —Cl |
| 1.799 | 2-(N-methyl-N-propargyl-amino)-ethyl | —OCH$_2$CH$_2$OCH$_3$ |
| 1.800 | 2-(N-methyl-N-propargyl-amino)-ethyl | cyclopropylmethoxy |
| 1.801 | 2-(N-methyl-N-propargyl-amino)-ethyl | trifluoromethyl |
| 1.802 | 2-(N-methyl-N-propargyl-amino)-ethyl | difluoromethoxy |
| 1.803 | 2-(N-methyl-N-propargyl-amino)-ethyl | trifluoromethoxy |
| 1.804 | 2-[N-(2-hydroxyethyl)-N-methyl-amino]-ethyl | —CH$_3$ |
| 1.805 | 2-[N-(2-hydroxyethyl)-N-methyl-amino]-ethyl | —Br |
| 1.806 | 2-[N-(2-hydroxyethyl)-N-methyl-amino]-ethyl | —F |
| 1.807 | 2-[N-(2-hydroxyethyl)-N-methyl-amino]-ethyl | —OCH$_3$ |
| 1.808 | 2-[N-(2-hydroxyethyl)-N-methyl-amino]-ethyl | —OCH$_2$CH$_3$ |
| 1.809 | 2-[N-(2-hydroxyethyl)-N-methyl-amino]-ethyl | —Cl |
| 1.810 | 2-[N-(2-hydroxyethyl)-N-methyl-amino]-ethyl | —OCH$_2$CH$_2$OCH$_3$ |
| 1.811 | 2-[N-(2-hydroxyethyl)-N-methyl-amino]-ethyl | cyclopropylmethoxy |
| 1.812 | 2-[N-(2-hydroxyethyl)-N-methyl-amino]-ethyl | trifluoromethyl |
| 1.813 | 2-[N-(2-hydroxyethyl)-N-methyl-amino]-ethyl | difluoromethoxy |
| 1.814 | 2-[N-(2-hydroxyethyl)-N-methyl-amino]-ethyl | trifluoromethoxy |
| 1.815 | 2-[N-(2-methoxyethyl)-N-methyl-amino]-ethyl | —CH$_3$ |
| 1.816 | 2-[N-(2-methoxyethyl)-N-methyl-amino]-ethyl | —Br |
| 1.817 | 2-[N-(2-methoxyethyl)-N-methyl-amino]-ethyl | —F |

TABLE 1-continued

| No. | R1 | R5 |
|---|---|---|
| 1.818 | 2-[N-(2-methoxyethyl)-N-methyl-amino]-ethyl | —OCH$_3$ |
| 1.819 | 2-[N-(2-methoxyethyl)-N-methyl-amino]-ethyl | —OCH$_2$CH$_3$ |
| 1.820 | 2-[N-(2-methoxyethyl)-N-methyl-amino]-ethyl | —Cl |
| 1.821 | 2-[N-(2-methoxyethyl)-N-methyl-amino]-ethyl | —OCH$_2$CH$_2$OCH$_3$ |
| 1.822 | 2-[N-(2-methoxyethyl)-N-methyl-amino]-ethyl | cyclopropylmethoxy |
| 1.823 | 2-[N-(2-methoxyethyl)-N-methyl-amino]-ethyl | trifluoromethyl |
| 1.824 | 2-[N-(2-methoxyethyl)-N-methyl-amino]-ethyl | difluoromethoxy |
| 1.825 | 2-[N-(2-methoxyethyl)-N-methyl-amino]-ethyl | trifluoromethoxy |
| 1.826 | 2-[N-ethyl-N-(2-hydroxyethyl)-amino]-ethyl | —CH$_3$ |
| 1.827 | 2-[N-ethyl-N-(2-hydroxyethyl)-amino]-ethyl | —Br |
| 1.828 | 2-[N-ethyl-N-(2-hydroxyethyl)-amino]-ethyl | —F |
| 1.829 | 2-[N-ethyl-N-(2-hydroxyethyl)-amino]-ethyl | —OCH$_3$ |
| 1.830 | 2-[N-ethyl-N-(2-hydroxyethyl)-amino]-ethyl | —OCH$_2$CH$_3$ |
| 1.831 | 2-[N-ethyl-N-(2-hydroxyethyl)-amino]-ethyl | —Cl |
| 1.832 | 2-[N-ethyl-N-(2-hydroxyethyl)-amino]-ethyl | —OCH$_2$CH$_2$OCH$_3$ |
| 1.833 | 2-[N-ethyl-N-(2-hydroxyethyl)-amino]-ethyl | cyclopropylmethoxy |
| 1.834 | 2-[N-ethyl-N-(2-hydroxyethyl)-amino]-ethyl | trifluoromethyl |
| 1.835 | 2-[N-ethyl-N-(2-hydroxyethyl)-amino]-ethyl | difluoromethoxy |
| 1.836 | 2-[N-ethyl-N-(2-hydroxyethyl)-amino]-ethyl | trifluoromethoxy |
| 1.837 | 2-[N-ethyl-N-(2-methoxyethyl)-amino]-ethyl | —CH$_3$ |
| 1.838 | 2-[N-ethyl-N-(2-methoxyethyl)-amino]-ethyl | —Br |
| 1.839 | 2-[N-ethyl-N-(2-methoxyethyl)-amino]-ethyl | —F |
| 1.840 | 2-[N-ethyl-N-(2-methoxyethyl)-amino]-ethyl | —OCH$_3$ |
| 1.841 | 2-[N-ethyl-N-(2-methoxyethyl)-amino]-ethyl | —OCH$_2$CH$_3$ |
| 1.842 | 2-[N-ethyl-N-(2-methoxyethyl)-amino]-ethyl | —Cl |
| 1.843 | 2-[N-ethyl-N-(2-methoxyethyl)-amino]-ethyl | —OCH$_2$CH$_2$OCH$_3$ |
| 1.844 | 2-[N-ethyl-N-(2-methoxyethyl)-amino]-ethyl | cyclopropylmethoxy |
| 1.845 | 2-[N-ethyl-N-(2-methoxyethyl)-amino]-ethyl | trifluoromethyl |
| 1.846 | 2-[N-ethyl-N-(2-methoxyethyl)-amino]-ethyl | difluoromethoxy |
| 1.847 | 2-[N-ethyl-N-(2-methoxyethyl)-amino]-ethyl | trifluoromethoxy |
| 1.848 | 2-(piperidin-1-yl)-ethyl | —CH$_3$ |
| 1.849 | 2-(piperidin-1-yl)-ethyl | —Br |
| 1.850 | 2-(piperidin-1-yl)-ethyl | —F |
| 1.851 | 2-(piperidin-1-yl)-ethyl | —OCH$_3$ |
| 1.852 | 2-(piperidin-1-yl)-ethyl | —OCH$_2$CH$_3$ |
| 1.853 | 2-(piperidin-1-yl)-ethyl | —Cl |
| 1.854 | 2-(piperidin-1-yl)-ethyl | —OCH$_2$CH$_2$OCH$_3$ |
| 1.855 | 2-(piperidin-1-yl)-ethyl | cyclopropylmethoxy |
| 1.856 | 2-(piperidin-1-yl)-ethyl | trifluoromethyl |
| 1.857 | 2-(piperidin-1-yl)-ethyl | difluoromethoxy |
| 1.858 | 2-(piperidin-1-yl)-ethyl | trifluoromethoxy |
| 1.859 | 2-(homopiperidin-1-yl)-ethyl | —CH$_3$ |
| 1.860 | 2-(homopiperidin-1-yl)-ethyl | —Br |
| 1.861 | 2-(homopiperidin-1-yl)-ethyl | —F |
| 1.862 | 2-(homopiperidin-1-yl)-ethyl | —OCH$_3$ |
| 1.863 | 2-(homopiperidin-1-yl)-ethyl | —OCH$_2$CH$_3$ |
| 1.864 | 2-(homopiperidin-1-yl)-ethyl | —Cl |
| 1.865 | 2-(homopiperidin-1-yl)-ethyl | —OCH$_2$CH$_2$OCH$_3$ |
| 1.866 | 2-(homopiperidin-1-yl)-ethyl | cyclopropylmethoxy |
| 1.867 | 2-(homopiperidin-1-yl)-ethyl | trifluoromethyl |
| 1.868 | 2-(homopiperidin-1-yl)-ethyl | difluoromethoxy |
| 1.869 | 2-(homopiperidin-1-yl)-ethyl | trifluoromethoxy |
| 1.870 | 2-(2,5-dihydropyrrol-1-yl)-ethyl | —CH$_3$ |
| 1.871 | 2-(2,5-dihydropyrrol-1-yl)-ethyl | —Br |
| 1.872 | 2-(2,5-dihydropyrrol-1-yl)-ethyl | —F |
| 1.873 | 2-(2,5-dihydropyrrol-1-yl)-ethyl | —OCH$_3$ |
| 1.874 | 2-(2,5-dihydropyrrol-1-yl)-ethyl | —OCH$_2$CH$_3$ |
| 1.875 | 2-(2,5-dihydropyrrol-1-yl)-ethyl | —Cl |
| 1.876 | 2-(2,5-dihydropyrrol-1-yl)-ethyl | —OCH$_2$CH$_2$OCH$_3$ |
| 1.877 | 2-(2,5-dihydropyrrol-1-yl)-ethyl | cyclopropylmethoxy |
| 1.878 | 2-(2,5-dihydropyrrol-1-yl)-ethyl | trifluoromethyl |
| 1.879 | 2-(2,5-dihydropyrrol-1-yl)-ethyl | difluoromethoxy |
| 1.880 | 2-(2,5-dihydropyrrol-1-yl)-ethyl | trifluoromethoxy |
| 1.881 | 2-(1,2,3,6-tetrahydropyridin-1-yl)-ethyl | —CH$_3$ |
| 1.882 | 2-(1,2,3,6-tetrahydropyridin-1-yl)-ethyl | —Br |
| 1.883 | 2-(1,2,3,6-tetrahydropyridin-1-yl)-ethyl | —F |
| 1.884 | 2-(1,2,3,6-tetrahydropyridin-1-yl)-ethyl | —OCH$_3$ |
| 1.885 | 2-(1,2,3,6-tetrahydropyridin-1-yl)-ethyl | —OCH$_2$CH$_3$ |
| 1.886 | 2-(1,2,3,6-tetrahydropyridin-1-yl)-ethyl | —Cl |
| 1.887 | 2-(1,2,3,6-tetrahydropyridin-1-yl)-ethyl | —OCH$_2$CH$_2$OCH$_3$ |
| 1.888 | 2-(1,2,3,6-tetrahydropyridin-1-yl)-ethyl | cyclopropylmethoxy |
| 1.889 | 2-(1,2,3,6-tetrahydropyridin-1-yl)-ethyl | trifluoromethyl |
| 1.890 | 2-(1,2,3,6-tetrahydropyridin-1-yl)-ethyl | difluoromethoxy |
| 1.891 | 2-(1,2,3,6-tetrahydropyridin-1-yl)-ethyl | trifluoromethoxy |

Further Embodiments of the Invention

The present invention also relates to intermediates (including their salts, stereoisomers and salts of these stereoisomers), methods and processes, which are disclosed herein and which are useful in synthesizing compounds according to this invention. Thus, the present invention also relates to processes disclosed herein for preparing compounds according to this invention, which processes comprise one or more steps of converting and/or reacting the mentioned intermediates with the appropriate reaction partners under conditions as disclosed herein.

The invention further relates to a process to prepare enantiomerically pure (stereomerically pure) intermediate compounds of formula IIa* comprising steps a) and b) and c).

The invention further relates to a process to prepare enantiomerically pure (stereomerically pure) intermediate compounds of formula Ia comprising steps a) and b) and c) and d).

The invention further relates to a process to prepare enantiomerically pure (stereomerically pure) intermediate compounds of formula Ia comprising steps c) and d).

The invention further relates to a process to prepare enantiomerically pure (stereomerically pure) compounds of formula I comprising steps c) and d) and e).

The invention further relates to a process to prepare enantiomerically pure (stereomerically pure) compounds of formula I comprising steps c) and d) and e) and f).

In a further embodiment the present invention comprises as well a process for the preparation of compounds of formula I

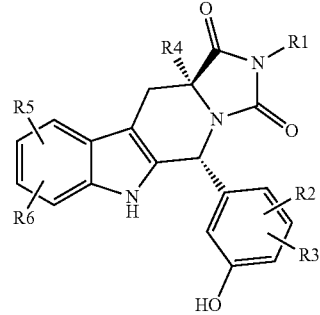

in which

R1 is 2-7C-alkyl substituted by —N(R111)R112, in which

R111 is 1-4C-alkyl, 2-4C-alkenyl, 2-4C-alkenyl, 3-7C-cycloalkyl, 3-7C-cycloalkyl-1-4C-alkyl, hydroxy-2-4C-alkyl, 1-4C-alkoxy-2-4C-alkyl, 1N-(1-4C-alkyl)-pyrazolyl, 1N—(H)-pyrazolyl, isoxazolyl, or completely or partially fluorine-substituted 1-4C-alkyl, R112 is hydrogen, 1-4C-alkyl, 3-7C-cycloalkyl, or 3-7C-cycloalkyl-1-4C-alkyl, or R111 and R112 together and with inclusion of the nitrogen atom, to which they are bonded, form a ring Het, in which Het is piperidin-1-yl, morpholin-4-yl, thiomorpholin-4-yl, S-oxo-thiomorpholin-4-yl, S,S-dioxo-thiomorpholin-4-yl, pyrrolidin-1-yl, azetidin-1-yl, homopiperidin-1-yl, 4N—(R113)-piperazin-1-yl, 4N—(R113)-homopiperazin-1-yl, 2,5-dihydro-pyrrol-1-yl, 1,2,3,6-tetra-hydropyridin-1-yl, pyrrol-1-yl, pyrazol-1-yl, imidazol-1-yl, triazol-1-yl, or tetrazol-1-yl, in which R113 is hydrogen, 1-4C-alkyl, 3-7C-cycloalkyl, 3-7C-cycloalkyl-1-4C-alkyl, 1-4C-alkylcarbonyl, amidino, or completely or partially fluorine-substituted 1-4C-alkyl, wherein said Het may be optionally substituted by one or two substituents independently selected from fluorine and 1-4C-alkyl, R2 is hydrogen, 1-4C-alkyl, halogen, trifluoromethyl, 1-4C-alkoxy or hydroxyl, R3 is hydrogen, 1-4C-alkyl, halogen, trifluoromethyl or 1-4C-alkoxy, R4 is 1-4C-alkyl, 3-7C-cycloalkyl or 3-7C-cycloalkyl-1-4C-alkyl, R5 is 1-4C-alkyl, halogen, 1-4C-alkoxy, trifluoromethyl, cyano, hydroxyl, phenyl-1-4C-alkoxy, 1-4C-alkoxy-2-4C-alkoxy, hydroxy-2-4C-alkoxy, 3-7C-cycloalkoxy, 3-7C-cycloalkyl-1-4C-alkoxy, or completely or predominantly fluorine-substituted 1-4C-alkoxy, R6 is hydrogen, 1-4C-alkyl or halogen, and the salts of these compounds, which process comprises the steps of b) providing a tryptophane derivative of formula IV,

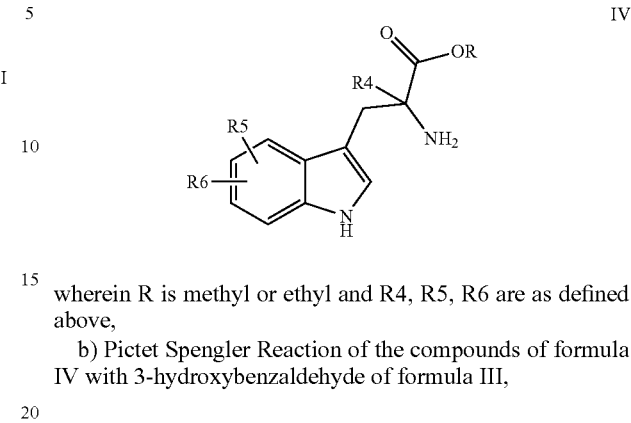

wherein R is methyl or ethyl and R4, R5, R6 are as defined above, b) Pictet Spengler Reaction of the compounds of formula IV with 3-hydroxybenzaldehyde of formula III,

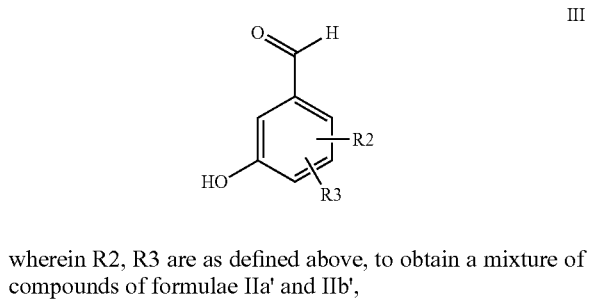

wherein R2, R3 are as defined above, to obtain a mixture of compounds of formulae IIa' and IIb',

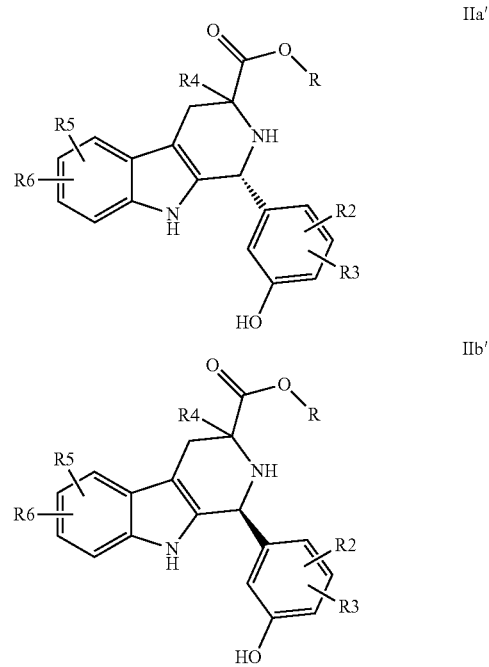

wherein R, R2, R3, R4, R5, R6 are as defined above, separation of the compounds of formulae IIa' and IIb' to obtain compounds of formula IIa', c) optional protection of the compounds of formula IIa' at the 3-hydroxyphenyl moiety to obtain compounds of formula IIa*'

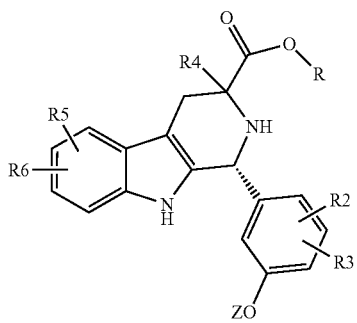

IIa*' wherein R, R2, R3, R4, R5, R6 are as defined above and Z is a protective group, d) heterocyclization of the compounds of formulae IIa*' or the compounds of formula IIa' by means of in situ prepared isocyanate R1-N=C=O by adding a reaction mixture of carbonyldiimidazole and an amine R1NH2 in a solvent to obtain compounds of formula Ia',

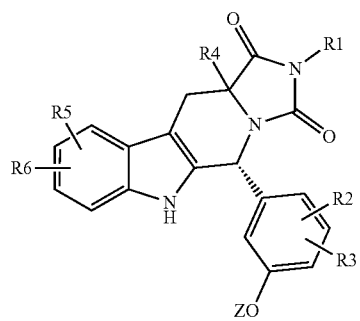

Ia' wherein R1-R6 and Z are as defined above, or to obtain compounds of formula I',

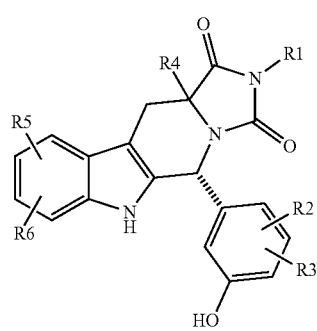

I' e) deprotection at the 3-hydroxyphenyl moiety of compounds of formula Ia' to obtain the compounds of formula I', provided that compounds of the formula IIa' have been protected at the 3-hydroxyphenyl moiety in step c), f) separation of the compounds of formula I from the compounds of formula I', g) optional conversion of the compounds of formula I into salts.

Intermediates

The invention further relates to the key intermediate compounds of formula IIa

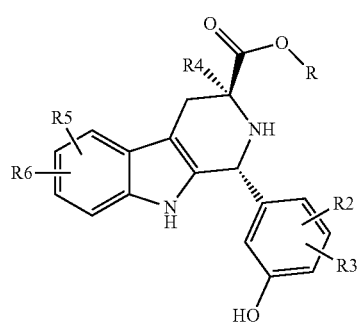

IIa wherein R and R2-R6 are as defined above.

The invention further relates to the key intermediate compounds of formula IIb

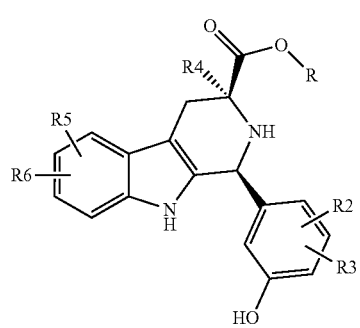

IIb wherein R and R2-R6 are as defined above.

The invention further relates to intermediate compounds of formula IIa*

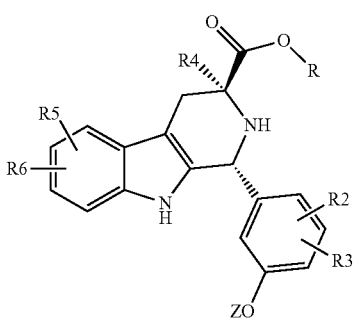

IIa* wherein R, R2-R6 and Z are as defined above.

The invention further relates to the intermediate compound of formula Ia

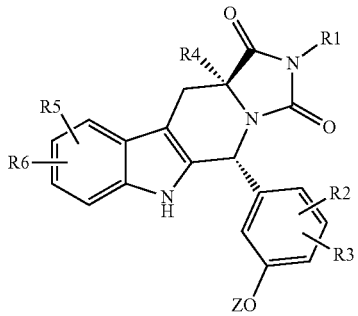

wherein R1-R6 and Z are as defined above.

Commercial Utility

The compounds according to the present invention have valuable pharmacological properties which can make them commercially applicable. Thus, for example, the compounds according to this invention can act as inhibitors of the mitotic kinesin Eg5 and these compounds are expected to be commercially applicable in the therapy of diseases responsive to the inhibition of this kinesin, such as e.g. those diseases mentioned in WO2007/096393 on page 235. Also, for example, the compounds according to this invention can display cell-cycle dependent, anti-proliferative and/or apoptosis inducing activity.

The commercial use is described in detail in WO2007/096393.

EXAMPLES

Example 1

Reaction Step a): Preparation of Enantiomerically Pure Tryptophane Derivative IVa

Example 1a

Nitro-reduction of α-methyl-α-nitro-3-(5-methoxy-1H-indolyl)-propionic acid methyl ester An inertized reactor is charged with 5.00 kg α-methyl-α-nitro-3-(5-methoxy-1H-indolyl)-propionic acid methylester, 40 L Methanol and 0.500 kg Palladium on charcoal, 10% Pd: Degussa E101NW) and the reaction mixture heated to 55-65° C. with stirring.

The reactor is pressurized with hydrogen gas to 3.5-5.0 bar with intensive stirring.

Hydrogenation is carried out at given temperature and pressure range until no more hydrogen uptake is detected. The suspension may be stirred over night at 55-65° C.

To complete conversion, the reaction mixture is stirred for 1.5-3.0 h at 4.0-5.0 bar hydrogen pressure. The hot suspension (40-60° C.) is filtered and the residue washed with 15 l prewarmed (40-60° C.) ethanol. 34-36 litres of the combined filtrates are distilled off in vacuo at 40-55° C. Then, 60 l of ethanol are added to the prewarmed (40-55° C.) solution. Under vacuum, 19-21 L solvent are distilled off at 40-55° C. The residual mixture is heated to 60-67° C. in a stirred reactor A, ready to use for the resolution process, described below.

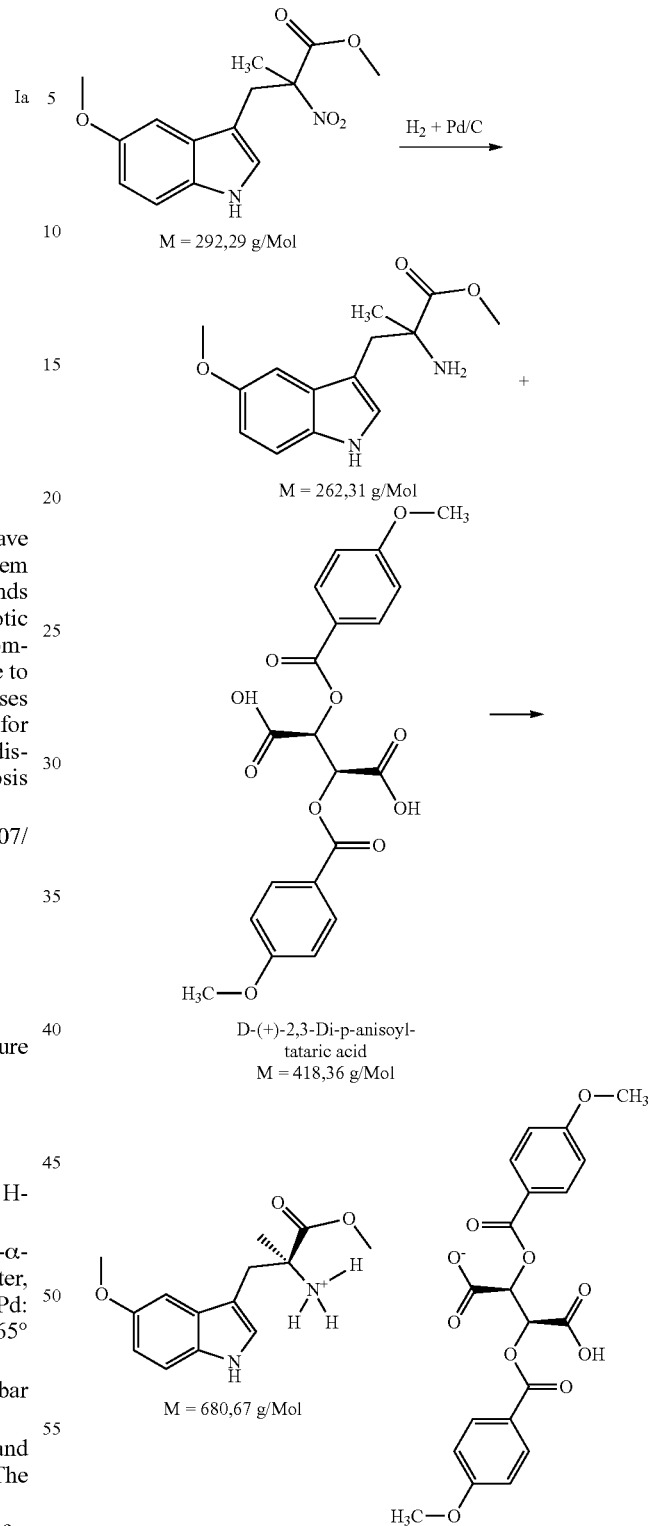

Example 1b

Resolution of Enantiomers of (R,S)-2-amino-3-(5-methoxy-1H-indolyl)-2-methyl-propionic Acid Methyl Ester via Diastereomeric Salt Formation with D-(+)-(S,S)-Di-p-anisoyl-tartaric Acid In a second reactor B, purged with nitrogen, 5.4 kg (0.75 equivalents) D-(+)-(S,S)-Di-p-anisoyl-tartaric acid (D-DATA) are dissolved in a mixture of 9 l of ethanol and 44 l of 2-propyl acetate. If necessary, the stirred mixture is warmed up to 30-40° C. for complete dissolution. The first half of this prewarmed solution is added to reactor B under stirring, during 40-80 min, keeping the temperature in reactor A in a range of 60-67° C. The second half of the prewarmed D-DATA solution is added under stirring in 2.5-4.0 hrs., keeping the reactor temperature at 60-67° C. Crystallization normally starts during addition of the second half of the DATA solution. The reaction mixture is cooled to 15-25° C. in 2-20 hrs. The obtained suspension can be stirred up to 5 d without change in purity of isolated diastereomeric salt.

The suspension is further cooled to 7-15° C. in 0.5-2.0 hrs. and stirring continued for 1-3 hrs and the solid phase isolated on a centrifuge, washed with 10-13 l of a mixture (3:2) of ethanol and 2-propyl acetate, dried in vacuum at 50° C. Yield: 4.9+/−1.2 kg.

Characterisation of isolated dry product: loss of drying <1.0%, identity correct by NMR and HPLC, Mp: 191° C. (decomp.), optical purity: >96% ee by chiral HPLC, optical rotation: $[\alpha]20D+120°+/-2°$.

Example 2

Liberation of Optically Pure α-methyl-α-amino-3-(5-methoxy-1H-indolyl)-propionic Acid Methyl Ester from its D-DATA Salt and Pictet Spengler Cyclisation to Prepare the Optically Active Key Intermediate IIa The liberation of optically pure α-methyl-α-amino-3-(5-methoxy-1H-indolyl)-propionic acid methyl ester from its D-DATA salt is connected with the subsequent Pictet-Spengler-Reaction, due to the fact, that the enantiomerically pure tryptophane-derivative is not crystalline (in contrast to the racemic mixture) but waxy and thus not easy to handle in pure form. Therefore, the free amino-ester is handeld as solution in toluene.

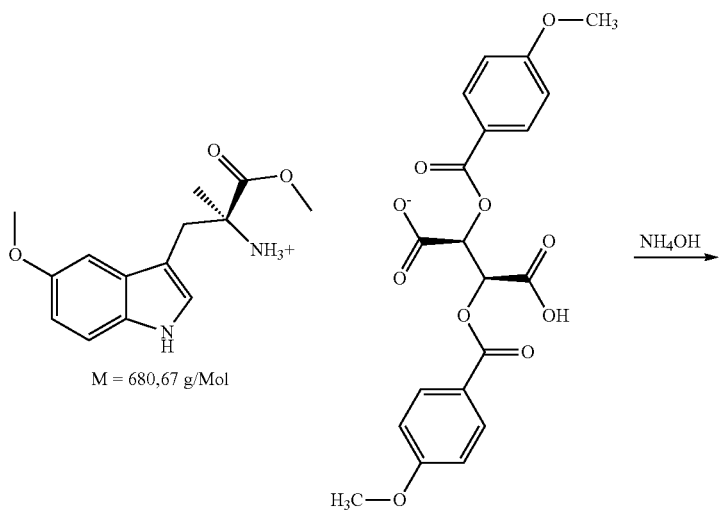

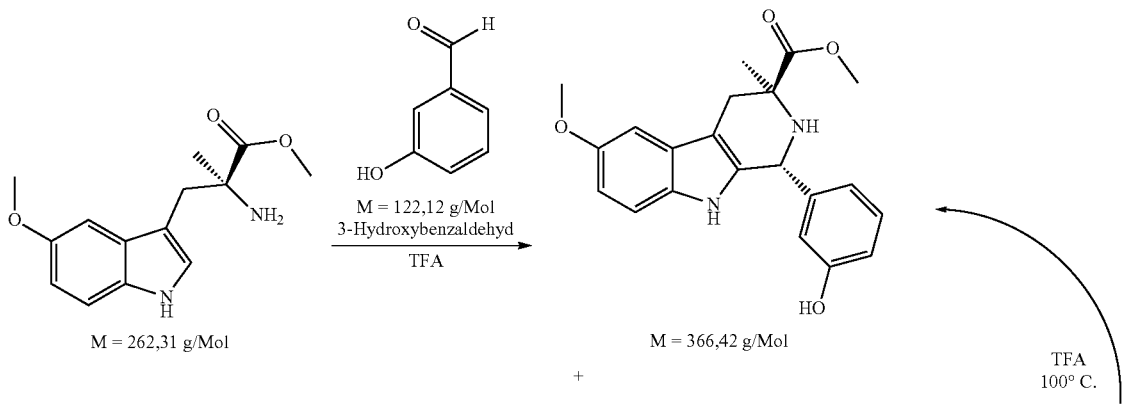

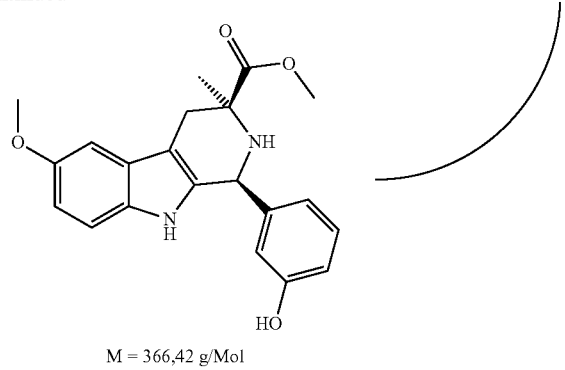

M = 366,42 g/Mol

An inertized reactor is charged with 5.00 kg α-methyl-α-amino-3-(5-methoxy-1H-indolyl)-propionic acid methylester, 12 L purified water and 22 L of ethyl acetate. 1.9 kg (3.8 equiv.) aqueous-ammonia solution (25%) are added in 10-30 min with stirring at 15-25° C. The clear biphasic solution is stirred for 20-40 min at 15-25° C.

Stirring is discontinued for >15 min at 15-25° C. to allow phase separation.

The lower (aqueous) phase is basified again with 0.35 kg (0.7 equiv.) aqueous-ammonia solution (25%) and extracted again with 10 l of ethyl acetate with stirring for 5-15 min.

Stirring is discontinued for phase separation. The combined organic phases are heated to 50-65° C. in vacuo with stirring to distill off 23-25 l of ethyl acetate.

Solvent exchange is achieved by adding 25 l of toluene to the reactor at 50-65° C. and distilling off 14-16 l in vacuo at 55-75° C. This codistillation is repeated a second time by addition of 10 l of toluene and distillation of 9-10 l at 55-75° C. in vacuo and the solution directly used in the following step.

Reaction Step b): Pictet-Spengler Cyclization

Pictet-Spengler Cyclization with 3-Hydroxybenzaldehyde to (+)-(1R,3S)-1-(3-Hydroxy-phenyl)-6-methoxy-3-methyl-2,3,4,9-tetrahydro-1H-beta-carboline-3-carboxylic acid methyl ester 0.880 kg (0.98 equiv.) 3-hydroxybenzaldehyde and 0.034 kg (0.04 equiv) of trifluoroacetic acid are charged to the reactor, containing the optically pure (S)-2-amino-3-(5-methoxy-1H-indolyl)-2-methyl-propionic acid methyl ester dissolved in toluene described above, with stirring at 53-61° C. The reaction mixture is stirred for further 15-24 hrs at 53-61° C., while the Pictet-Spengler-product is crystallizing out of the reaction mixture.

In process control by TLC: <2% of starting compound (S)-2-amino-3-(5-methoxy-1H-indolyl)-2-methyl-propionic acid methyl ester. 17 l ethyl acetate are added to the reaction mixture at a temperature of 30-55° C., which is then cooled to 20-35° C. Quench of trifluoroacetic acid is achieved by addition of 0.48 kg sodium hydrogencarbonate, dissolved in 5 l purified water, and stirring the biphasic mixture for 5-20 min at 20-35° C.

Stirring is interrupted and phase separation allowed for >15 min at 15-25° C. The upper phase, containing product, is separated and heated with stirring to 55-75° C. Under vacuum 16-18 l of solvent are distilled off. Solvent exchange is achieved by adding 20 l of toluene and distilling off 11-12 l of solvent at 70-90° C.

The reaction mixture is further heated at 100-110° C. to reflux under stirring for 15-60 min.

To crystallize the Pict-Spengler-product completely, the reaction mixture is cooled to 7-15° C. in 8-24 hrs and stirred during further >1 h at 7-15° C. before centrifugation of the cold suspension. The product is washed with 4-7 l toluene and dried in vacuo at 50° C. for 12-24 hrs. Yield: 2.0+/−0.3 kg (75+/−10%).

Product quality tested by NMR, chiral HPLC: >99.2%, optical rotation: 53+/−2°, loss of drying.

A second crop can be obtained from the mother liquor of the centrifugation step, by repeated isomerization of the unwanted diastereomer: Heating the solution in toluene in presence of trifluoroacetic acid as catalyst to 100-110° C. with stirring for 4-5 hrs and extractive workup and crystallisation as described for the first crop yields another 0.3+/−0.1 kg (11+/−5%).

Example 3

Reaction Steps 1c) and 1d): Silylation of the Pictet Spengler Product and Hydantoine Cyclization Depending on the purity of available carbonyldiimidazole used in the preparation of N,N-DMEDA-imidazolide, the above described process can be run in two alternative ways:

1. Technical Grade Carbonyldiimidazole with Purity 90-95%

Reaction-solvent: mixture acetonitrile/toluene for N,N-DMEDA-imidazolide, not completely soluble in pure toluene. Faster addition of N,N-DMEDA-imidazolide.

Reaction temperature continuously increased from 55-105° C. by distilling off acetonitrile.

2. Purum Grade Carbonyldiimidazole with Purity >97%

Reaction-solvent: pure toluene, for N,N-DMEDA-imidazolide completely soluble in pure toluene. Isothermal, slow dosage of the N,N-DMEDA-imidazolide at optimum activation temperature, i.e. 100-105° C.

Preparation of Enantiomerically Pure (3aS,10R)-2-(2-dimethylaminoethyl)-10-(3-hydroxyphenyl)-6-methoxy-3a-methyl-3a,49,10-tetrahydro-2,9,10a-triaza-cyclopenta-[b]fluorene-1,3-dione Example 3.1

Process in Toluene/MeCN Solvent Mixture, Batch-Processing

1. Silylation: In Inertized Reactor A are Suspended:

5.00 kg of (+)-(1R,3S)-1-(3-Hydroxy-phenyl)-6-methoxy-3-methyl-2,3,4,9-tetrahydro-1H-beta-carboline-3-carboxylic acid methyl ester are suspended in 14 l of acetonitril. The mixture is heated to 45-55° C., resulting in a white slurry. At this temperature, 1.70 kg (1.23 eq) triethylamine are added in 30-60 min with stirring. The dosage line is rinsed with additional 2-3 l of acetonitril and the reaction mixture stirred for 20-40 min at 45-55° C., while a clear solution is obtained. Then, 1.80 kg (1.21 eq.) of chloro-trimethylsilane are added to the reaction-mixture during 30-120 min at 45-55° C. and the dosage line rinsed with 2-3 l of acetonitrile. The reaction-mixture changes again to a white solution. The reaction mass is stirred for 30-60 min at 55-65° C., forming an orange-yellow solution.

The solution can be stored over night with stirring at 15-25° C.

2. Preparation of the N,N-DMEDA-imidazolide: In Inertized Reactor B are Suspended:

4.50 kg (2.03 eq. to Pictet-Spengler) N,N-Carbonyldiimidazole in 13 l of acetonitril and 5 l of toluene. After cooling the beige suspension to 5-15° C., 2.45 kg (2.04 eq.) N,N-Dimethylethylendiamine diluted in 5 l of toluene are added in 30-90 min at 5-25° C. to the reaction slurry, which changes to a clear solution at the end of dosage.

3. Hydantoine-cyclization: the solution of N,N-DMEDA-imidazolide in toluene/acetonitril prepared in reactor B, is dosed in 1.5-4 hrs. at reaction temperature of 55-80° C. to the reaction mixture in reactor A.

The reaction mixture can be stored over night without heating at 20-50° C. with stirring.

To start the reaction, reactor-temperature is increased to ca. 80° C. to distill off 22-25 l of acetonitril, while the boiling temperature is continuously increases. 14 l toluene are added to the reaction mixture at 80-100° C. and further solvent distilled off, until reactor temperature reaches 100° C. The reaction mixture is further heated with stirring for 8-12 hrs at 100° C. In process control: reaction mixture is cooled to 80° C. for sampling.

HPLC: if starting material <8% processing is continued with work-up. If content of starting material is >8%: mixture is stirred further at 100° C. for 8-12 hrs, followed by work-up.

4. Work-up: The reaction mixture is cooled to 45-55° C., subsequently 13 l methylethyl-ketone and 5 l purified water are added and the biphasic solution stirred at 45-55° C. during 1-2 hrs. Stirring is interrupted to allow phase-separation at 45-55° C. The aqueous phase (lower layer) is drowned into a container, the organic phase (upper layer) is washed with a solution of 0.5 kg sodium chloride in 5 l purified water by stirring at 45-55° C. for 10 min, before drowning the aqueous washings to the container. The organic phase is heated to 45-60° C. with stirring and 18-23 l of solvent distilled off.

Add 10 l of methanol at 55-65° C. during 45-120 min.

If no thin suspension is obtained, seading crystals are added to induce crystallization.

After crystalization has started, the slurry is further stirred at 50-60° C. for 30-90 min.

The stirred suspension is slowly cooled to 8-15° C. in 4-8 hrs and further kept at this temperature for complete crystallization for 12 hrs-3 days.

The suspension is centrifuged at 8-15° C. and the product washed with 2-3 l of precooled methanol. The solvent-wet product is dried at 40° C. in vacuo.

In process control: loss of drying <2%, identy by TLC and HPLC.

Yield: 3.98 kg+/−0.25 kg, 65%+/−5%.

Example 3.2

Process in Toluene, Isothermal Processing

1. Silylation: In Inertized Reactor A are Suspended:

1.00 kg of (+)-(1R,3S)-1-(3-Hydroxy-phenyl)-6-methoxy-3-methyl-2,3,4,9-tetrahydro-1H-beta-carboline-3-carboxylic acid methyl ester in 6 l THF. The mixture is heated to 50-52° C., resulting in a white slurry. At this temperature, 0.30 kg (1.20 eq) triethylamine are added in 30-40 min with stirring. The reaction mixture is stirred for 20-40 min at 50-52° C., while a white suspension is formed. Then, 0.35 kg (1.20 eq.) of chloro-trimethylsilane are added to the reaction-mixture during 90 min at 50-52° C. The reaction-mixture is stirred for further 2.5-3 hrs. at 60-62° C.

(The solution can be stored over night with stirring at 15-25° C. if necessary.)

12 l of toluene are added and the reactor-temperature continuously raised in 3.5-4.0 hrs from 60-62° C. to 100-105° C., to distill off completely the low boiling THF.

2. Preparation of the N,N-DMEDA-imidazolide: In Inertized Reactor B are Suspended:

0.882 kg (2.00 eq.) N,N-Carbonyldiimidazole in 2.64 l of toluene at 20° C. After cooling the beige suspension to 5-10° C., 0.480 kg (2.00 eq.) N,N-Dimethylethylendiamine diluted in 0.69 l toluene are added in 45-60 min at 5-10° C. to the reaction slurry. Stirring for further 3-3.5 hrs. at 10-15° C. and for 3-4 hrs. at 20-25° C., yields a clear, almost colourless solution.

3. Hydantoine-cyclization: the solution of N,N-DMEDA-imidazolide in toluene prepared in reactor B, is dosed in 9.0-9.5 hrs. via a dosage-pump with weight-control at reaction temperature of 100-105° C. to the reaction mixture in reactor A.

The reaction mixture is further heated with stirring for 8-12 hrs at 100° C.

In process control: reaction mixture is cooled to 80° C. for sampling.

TLC or HPLC: if starting material >2% processing is continued with work-up. If content of starting material is >2%: mixture is stirred further at 100° C. for 8-12 hrs, followed by work-up.

4. Work-up: The reaction mixture is cooled to 50-55° C., subsequently 2 l of methylethylketone and 2 l purified water are added and the biphasic solution stirred at 45-50° C. during 0.5-1 h. Stirring is interrupted to allow phase-separation at 45-50° C.

The aqueous phase (lower layer) is separated into a container and the organic phase (upper layer) is washed with a solution of 0.2 kg sodium chloride in 2 l purified water with stirring at 45-55° C. for 1 h, before separating the aqueous washings to the container.

5.0 l of methylethylketone are added to the organic phase to dissolve the product completely before filtration over a paper filter to take out any solid residuals. The filtrate is evaporated at 60° C. in vacuo and codistilled twice with 4 l of toluene and subsequently twice with 4 l of methanol. Crystallization starts during solvent exchange to methanol and is completed by cooling the suspension to 0-5° C. with stirring for 1-2 hrs.

The suspension is filtered at 5-15° C. and the product washed with 0.3-0.5 l of precooled methanol. The solvent-wet product is dried at 60° C. in vacuo for 24 hrs.

In process control: loss of drying <3%, identity by TLC and (chiral)-HPLC, NMR.

Yield: 1.025 kg, 84%.

It has now been surprisingly found that the integrated process described above enables significant reduction of by-products and a distinct increase of overall yield, especially because:

1. Dosing temperature is adapted to the optimum activation temperature of the isocyanate-precursor.
2. Dosing speed of the imidazolide is adapted to the reaction speed of the annulation step.

Therefore, especially synthesis protocol in pure toluene described above further reduces accumulation of impurities during the annulation reaction and thus enables higher overall product-yield and -purity.

Chemical yield in Toluene/MeCN: 60-70%, purity of crystalline cpd. >98.5% (HPLC)

Chemical yield in Toluene: 75-85%, purity of crystalline cpd. >99.0% (HPLC).

The hydantoine cyclisation is shown in Scheme 6

Scheme 6

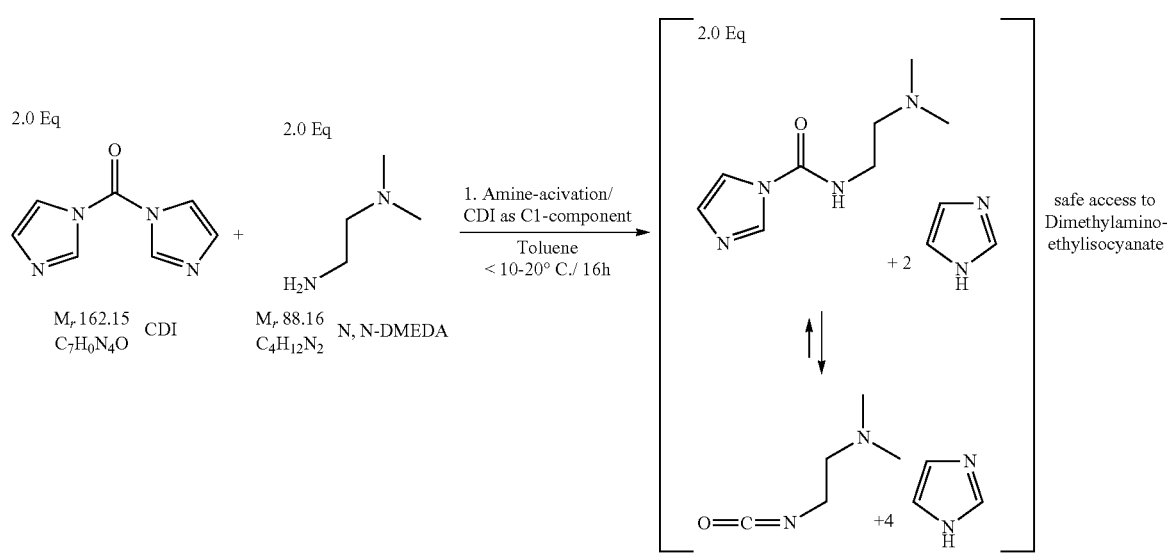

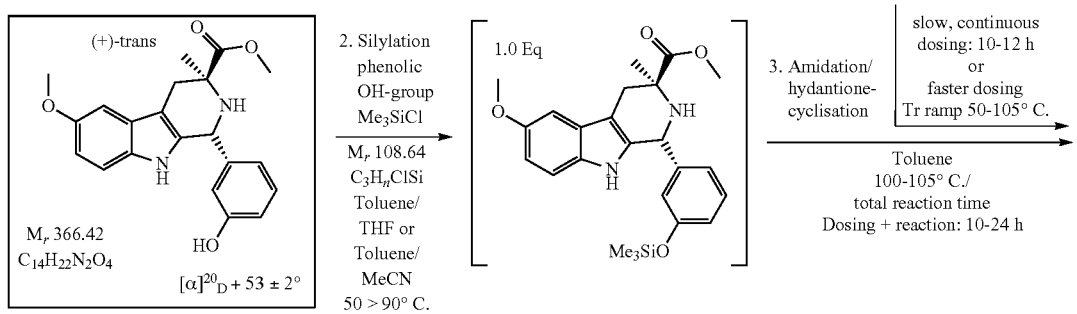

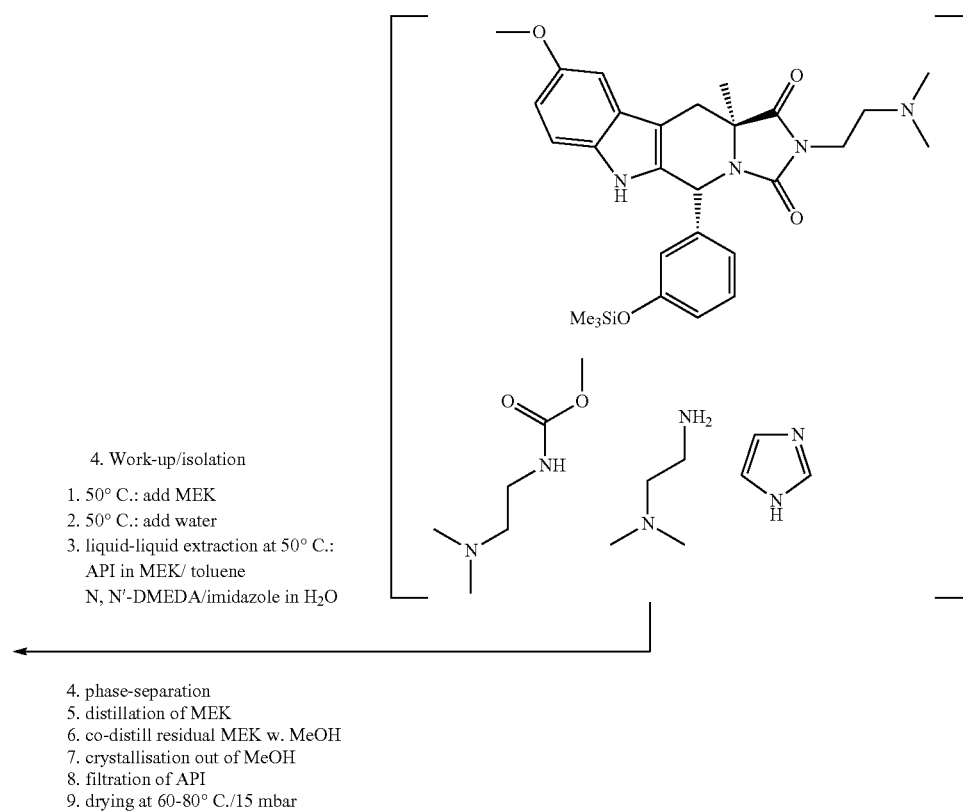

4. Work-up/isolation
1. 50° C.: add MEK
2. 50° C.: add water
3. liquid-liquid extraction at 50° C.:
   API in MEK/ toluene
   N, N′-DMEDA/imidazole in H₂O 4. phase-separation
5. distillation of MEK
6. co-distill residual MEK w. MeOH
7. crystallisation out of MeOH
8. filtration of API
9. drying at 60-80° C./15 mbar

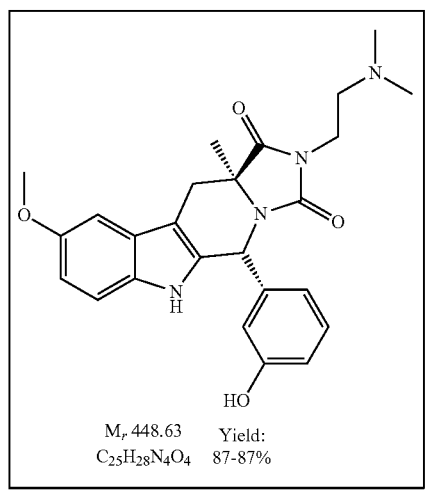

$M_r$ 448.63  Yield:
$C_{25}H_{28}N_4O_4$  87-87%

Example 4

Step f) Conversion into Hydrochloric Acid Salt

For converting the free base of (3aS,10R)-2-(2-dimethylaminoethyl)-10-(3-hydroxyphenyl)-6-methoxy-3a-methyl-3a,49,10-tetrahydro-2,9,10a-triaza-cyclopenta[b]fluorene-1,3-dione into its HCl-salt, the free base is suspended in hot methanol followed by addition of Chloro-trimethylsilane (which is solvolyzed to dry HCl and methyltrimethylsilylether) or using Hydrochloric acid, yields a HCl-salt, which is soluble in a narrow temperature range and crystallizes in definite crystalline form with cooling.

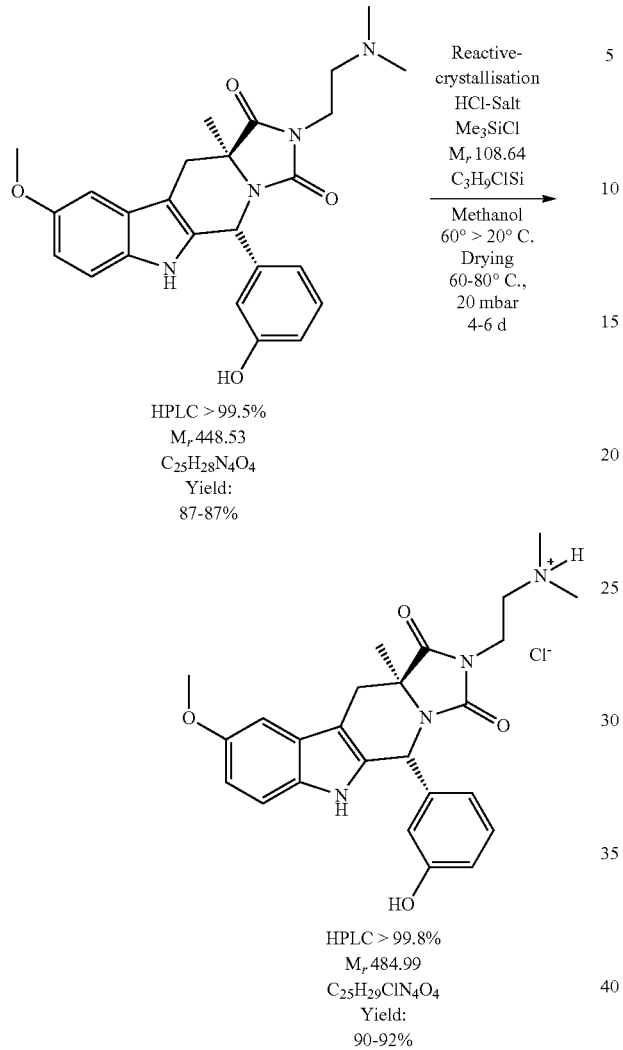

Scheme 7

HPLC > 99.5%
M$_r$ 448.53
C$_{25}$H$_{28}$N$_4$O$_4$
Yield:
87-87%

Reactive-
crystallisation
HCl-Salt
Me$_3$SiCl
M$_r$ 108.64
C$_3$H$_9$ClSi
───────────
Methanol
60° > 20° C.
Drying
60-80° C.,
20 mbar
4-6 d HPLC > 99.8%
M$_r$ 484.99
C$_{25}$H$_{29}$ClN$_4$O$_4$
Yield:
90-92%

Example 4.1

Preparation of Enantiomerically Pure (3aS,10R)-2-(2-dimethylammonioethyl)-10-(3-hydroxyphenyl)-6-methoxy-3a-methyl-3a,49,10-tetrahydro-2,9,10a-triaza-cyclopenta-[b]fluorene-1,3-dione chloride 2.0 kg (3aS,10R)-2-(2-dimethylaminoethyl)-10-(3-hydroxyphenyl)-6-methoxy-3a-methyl-3a,4,9,10-tetrahydro-2,9,10a-triaza-cyclopenta[b]fluorene-1,3-dione are dissolved in 8 l acetone and filtrated to take out any solid residuals. The solvent is evaporated at 55° C. until a thick slurry is obtained and coevaporated twice with 3 l of methanol.

The slurry is diluted with 10 l of methanol and heated to 60-65° C. in 1-2 h with stirring.

At this temperature, 0.722 kg (1.5 equ) Chloro-trimethylsilane are continuously added in 30-60 min. The product dissolves in methanol after about half of the dosing of chlorotrimethylsilane at the end of the dosing the HCl-salt starts crystallizing out of the hot solution in minor amount. The reaction mixture is cooled to 20° C. in 10 hours with programmed cooling ramp and further cooled to 5° C. in 1-2 hrs. The cool suspension is filtered, washed with 0.5 l precooled methanol and dried in vacuo at 60° C. for 4-6 days.

Yield: 2.0 kg (92%).

QC-end control: Identity by NMR, purity with chiral HPLC, Cl, residual solvents

The invention claimed is:

1. A process for preparing an enantiomerically pure (stereomerically pure) compound of formula

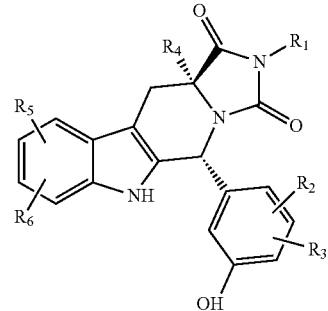

I in which

R1 is 2-7C-alkyl substituted by —N(R111)R112,

R111 is 1-4C-alkyl, 2-4C-alkenyl, 2-4C-alkinyl, 3-7C-cycloalkyl, 3-7C-cycloalkyl-1-4C-alkyl, hydroxy-2-4C-alkyl, 1-4C-alkoxy-2-4C-alkyl, 1N-(1-4C-alkyl)-pyrazolyl, 1N—(H)-pyrazolyl, isoxazolyl, or completely or partially fluorine-substituted 1-4C-alkyl, R112 is hydrogen, 1-4C-alkyl, 3-7C-cycloalkyl, or 3-7C-cycloalkyl-1-4C-alkyl, or R111 and R112 together and with inclusion of the nitrogen atom, to which they are bonded, form a ring Het, Het is piperidin-1-yl, morpholin-4-yl, thiomorpholin-4-yl, S-oxo-thiomorpholin-4-yl, S,S-dioxo-thiomorpholin-4-yl, pyrrolidin-1-yl, azetidin-1-yl, homopiperidin-1-yl, 4N—(R113)-piperazin-1-yl, 4N—(R113)-homopiperazin-1-yl, 2,5-dihydro-pyrrol-1-yl, 1,2,3,6-tetra-hydropyridin-1-yl, pyrrol-1-yl, pyrazol-1-yl, imidazol-1-yl, triazol-1-yl, or tetrazol-1-yl, wherein said Het may be optionally substituted by one or two substituents independently selected from fluorine and 1-4C-alkyl, R113 is hydrogen, 1-4C-alkyl, 3-7C-cycloalkyl, 3-7C-cycloalkyl-1-4C-alkyl, 1-4C-alkylcarbonyl, amidino, or completely or partially fluorine-substituted 1-4C-alkyl, R2 is hydrogen, 1-4C-alkyl, halogen trifluoromethyl, 1-4C-alkoxy or hydroxyl, R3 is hydrogen, 1-4C-alkyl, halogen, trifluoromethyl or 1-4C-alkoxy, R4 is 1-4C-alkyl, 3-7C-cycloalkyl or 3-7C-cycloalkyl-1-4C-alkyl, R5 is 1-4C-alkyl, halogen, 1-4C-alkoxy, trifluoromethyl, cyano, hydroxyl, phenyl-1-4C-alkoxy, 1-4C-alkoxy-2-4C-alkoxy, hydroxy-2-4C-alkoxy, 3-7C-cycloalkoxy, 3-7C-cycloalkyl-1-4C-alkoxy, or completely or predominantly fluorine-substituted 1-4C-alkoxy, and R6 is hydrogen, 1-4C-alkyl or halogen, or a salt thereof which process comprises
c) optionally protecting the compound of formula IIa

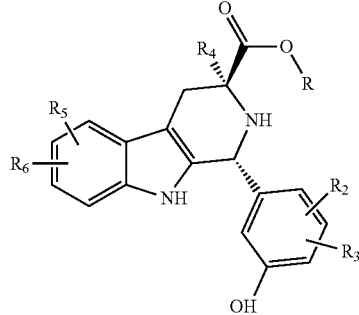

wherein R, R2, R3, R4, R5, and R6 are as defined above,
at the 3-hydroxyphenyl moiety to obtain a compound of formula IIa*,

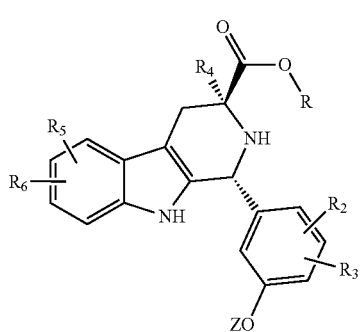

wherein R, R2, R3, R4, R5, and R6 are as defined above
and Z is a protective group, d) heterocyclizing the compound of formula IIa* or the compound of formula IIa by in situ prepared isocyanate R1-N=C=O by adding a reaction mixture of carbonyldiimidazole and an amine R1NH$_2$ in a solvent selected from the group consisting of toluene, xylene, a mixture of toluene and acetonitrile and a mixture of toluene and benzonitrile to obtain a compound of formula Ia,

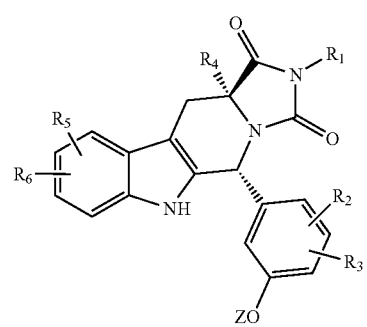

wherein R1-R6 and Z are as defined above,
or to obtain the compound of formula I, and
e) deprotecting the 3-hydroxyphenyl moiety of the compound of formula Ia to obtain the compound of formula I, provided that the compound of formula IIa have been protected at the 3-hydroxyphenyl moiety in c).

2. A process for preparing an enantiomerically pure (stereomerically pure) compound of formula Ia

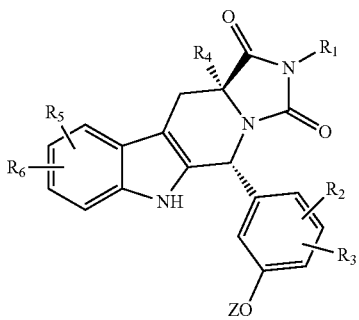

wherein

R1 is 2-7C-alkyl substituted by —N(R111)R112,

R111 is 1-4C-alkyl, 2-4C-alkenyl, 2-4C-alkinyl, 3-7C-cycloalkyl, 3-7C-cycloalkyl-1-4C-alkyl, hydroxy-2-4C-alkyl, 1-4C-alkoxy-2-4C-alkyl, 1N-(1-4C-alkyl)-pyrazolyl, 1N—(H)-pyrazolyl, isoxazolyl, or completely or partially fluorine-substituted 1-4C-alkyl, R112 is hydrogen, 1-4C-alkyl, 3-7C-cycloalkyl, or 3-7C-cycloalkyl-1-4C-alkyl, or R111 and R112 together and with inclusion of the nitrogen atom, to which they are bonded, form a ring Het, Het is piperidin-1-yl, morpholin-4-yl, thiomorpholin-4-yl, S-oxo-thiomorpholin-4-yl, S,S-dioxo-thiomorpholin-4-yl, pyrrolidin-1-yl, azetidin-1-yl, homopiperidin-1-yl, 4N—(R113)-piperazin-1-yl, 4N—(R113)-homopiperazin-1-yl, 2,5-dihydro-pyrrol-1-yl, 1,2,3,6-tetra-hydropyridin-1-yl, pyrrol-1-yl, pyrazol-1-yl, imidazol-1-yl, triazol-1-yl, or tetrazol-1-yl, wherein said Het may be optionally substituted by one or two substituents independently selected from fluorine and 1-4C-alkyl, R113 is hydrogen, 1-4C-alkyl, 3-7C-cycloalkyl, 3-7C-cycloalkyl-1-4C-alkyl, 1-4C-alkylcarbonyl, amidino, or completely or partially fluorine-substituted 1-4C-alkyl, R2 is hydrogen, 1-4C-alkyl, halogen trifluoromethyl, 1-4C-alkoxy or hydroxyl, R3 is hydrogen, 1-4C-alkyl, halogen, trifluoromethyl or 1-4C-alkoxy, R4 is 1-4C-alkyl, 3-7C-cycloalkyl or 3-7C-cycloalkyl-1-4C-alkyl, R5 is 1-4C-alkyl, halogen, 1-4C-alkoxy, trifluoromethyl, cyano, hydroxyl, phenyl-1-4C-alkoxy, 1-4C-alkoxy-2-4C-alkoxy, hydroxy-2-4C-alkoxy, 3-7C-cycloalkoxy, 3-7C-cycloalkyl-1-4C-alkoxy, or completely or predominantly fluorine-substituted 1-4C-alkoxy, R6 is hydrogen, 1-4C-alkyl or halogen, and Z is a protective group, which process comprises
c) optionally protecting the compound of formula IIa

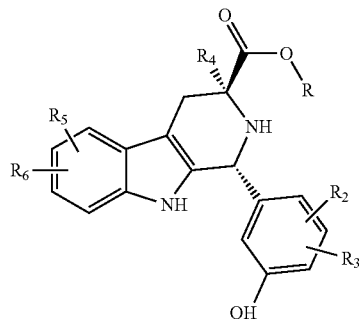

wherein R, R2, R3, R4, R5, and R6 are as defined above, at the 3-hydroxyphenyl moiety to obtain a compound of formula IIa*,

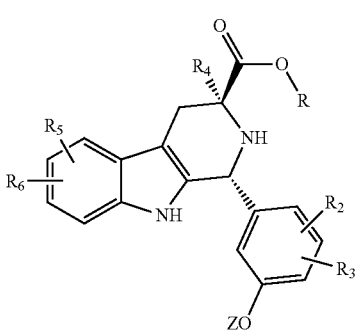

wherein R, R2, R3, R4, R5, and R6 are as defined above and Z is a protective group, and
d) heterocyclizing the compound of formula IIa* or the compound of formula IIa by in situ prepared isocyanate R1-N=C=O by adding a reaction mixture of carbonyldiimidazole and an amine R1NH$_2$ in a solvent selected from the group consisting of toluene, xylene, a mixture of toluene and acetonitrile and a mixture of toluene and benzonitrile to obtain a compound of formula Ia.

3. A process according to claim 1 for preparing a compound of formula I

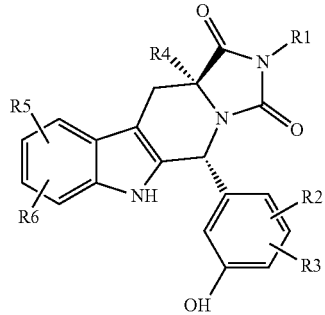

in which

R1 is 2-7C-alkyl substituted by —N(R111)R112,

R111 is 1-4C-alkyl, 2-4C-alkenyl, 2-4C-alkinyl, 3-7C-cycloalkyl, 3-7C-cycloalkyl-1-4C-alkyl, hydroxy-2-4C-alkyl, 1-4C-alkoxy-2-4C-alkyl, 1N-(1-4C-alkyl)-pyrazolyl, 1N—(H)-pyrazolyl, isoxazolyl, or completely or partially fluorine-substituted 1-4C-alkyl, R112 is hydrogen, 1-4C-alkyl, 3-7C-cycloalkyl, or 3-7C-cycloalkyl-1-4C-alkyl, or R111 and R112 together and with inclusion of the nitrogen atom, to which they are bonded, form a ring Het, Het is piperidin-1-yl, morpholin-4-yl, thiomorpholin-4-yl, S-oxo-thiomorpholin-4-yl, S,S-dioxo-thiomorpholin-4-yl, pyrrolidin-1-yl, azetidin-1-yl, homopiperidin-1-yl, 4N—(R113)-piperazin-1-yl, 4N—(R113)-homopiperazin-1-yl, 2,5-dihydro-pyrrol-1-yl, 1,2,3,6-tetra-hydropyridin-1-yl, pyrrol-1-yl, pyrazol-1-yl, imidazol-1-yl, triazol-1-yl, or tetrazol-1-yl, wherein said Het may be optionally substituted by one or two substituents independently selected from fluorine and 1-4C-alkyl, R113 is hydrogen, 1-4C-alkyl, 3-7C-cycloalkyl, 3-7C-cycloalkyl-1-4C-alkyl, 1-4C-alkylcarbonyl, amidino, or completely or partially fluorine-substituted 1-4C-alkyl, R2 is hydrogen, 1-4C-alkyl, halogen trifluoromethyl, 1-4C-alkoxy or hydroxyl, R3 is hydrogen, 1-4C-alkyl, halogen, trifluoromethyl or 1-4C-alkoxy, R4 is 1-4C-alkyl, 3-7C-cycloalkyl or 3-7C-cycloalkyl-1-4C-alkyl, R5 is 1-4C-alkyl, halogen, 1-4C-alkoxy, trifluoromethyl, cyano, hydroxyl, phenyl-1-4C-alkoxy, 1-4C-alkoxy-2-4C-alkoxy, hydroxy-2-4C-alkoxy, 3-7C-cycloalkoxy, 3-7C-cycloalkyl-1-4C-alkoxy, or completely or predominantly fluorine-substituted 1-4C-alkoxy, and R6 is hydrogen, 1-4C-alkyl or halogen, or a salt thereof which process comprises
a) providing an enantiomerically pure (stereomerically pure) tryptophane compound of formula IVa,

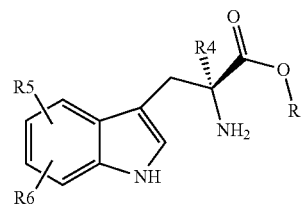

wherein R is methyl or ethyl and R4, R5, and R6 are as defined above,
b) reacting the compound Pictet Spengler Reaction of the compounds of formula IVa with 3-hydroxybenzaldehyde of formula III in a Pictet Spengler Reaction,

63

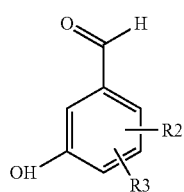

III wherein R2, and R3 are as defined above,
to obtain a mixture of compounds of formulae IIa and IIb,

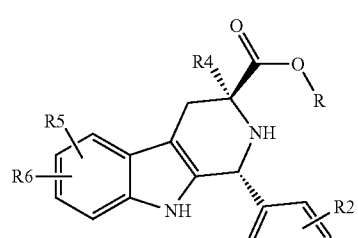

IIa

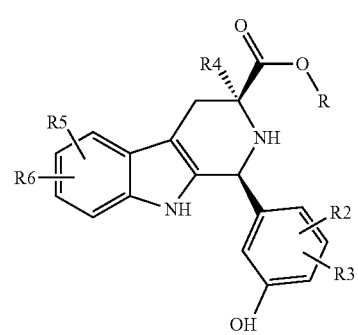

IIb wherein R, R2, R3, R4, R5, and R6 are as defined above,
and separating of the compounds of formulae IIa and IIb
to obtain a compound of formula IIa, c) optionally protecting the compound of formula IIa at the 3-hydroxyphenyl moiety to obtain a compound of formula IIa*,

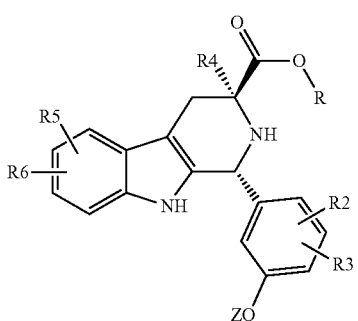

IIa* wherein R, R2, R3, R4, R5, and R6 are as defined above
and Z is a protective group, d) heterocyclizing the compound of formula IIa* or the compound of formula IIa by in situ prepared isocyanate R1-N=C=O by adding a reaction mixture of carbonyldiimidazole and an amine R1NH$_2$ in a solvent selected from the group consisting of toluene, xylene, a mixture of toluene and acetonitrile and a mixture of toluene and benzonitrile to obtain a compound of formula Ia,

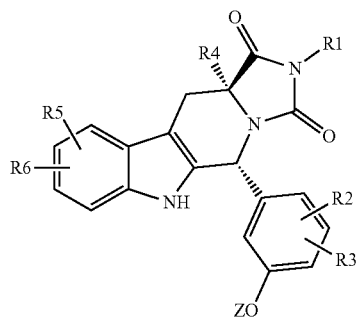

Ia wherein R1-R6 and Z are as defined above,
or to obtain the compound of formula I, e) deprotecting at the 3-hydroxyphenyl moiety of the compound of formula Ia to obtain the compound of formula I, provided that the compound of formula IIa have been protected at the 3-hydroxyphenyl moiety in c), and optionally converting the compound of formula I into a salt thereof.

4. A process according to claim 3, wherein the enantiomerically pure (stereomerically pure) tryptophane compound of formula IVa of a) is provided by optical resolution of a racemic tryptophane-ester of formula IV,

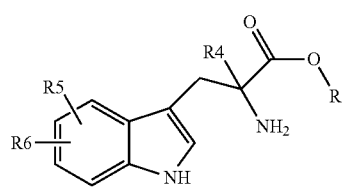

IV wherein R is methyl or ethyl and R4, R5 and R6 are as defined for the compound of formula I, by salt formation with an optically active acid and subsequent resolution of the salt by crystallization from a solvent system to obtain an enantiomerically pure (stereomerically pure) tryptophane compound salt of formula IVa*,

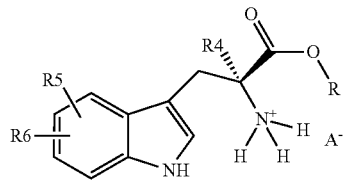

IVa* wherein R, R4, R5 and R6 are as defined above and A is the anion derived from the optically active acid, and
subsequent liberation of the compound of formula IVa

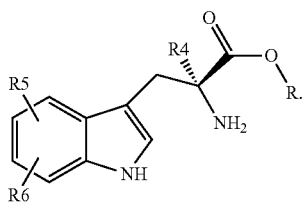

5. A process according to claim 4, wherein the optical resolution of the racemic tryptophane-ester of formula IV is achieved by salt formation with (2S,3S)-(+)-Di(p-anisoyl) tartaric acid.

6. A process according to claim 3, wherein in c), Z is a tri(alkyl)silyl halide.

7. A process according to claim 3, wherein the compound of formula IIa is protected in c) and the compound of formula Ia is deprotected in e).

8. A process according to claim 3, wherein in d) the solvent is a mixture of acetonitrile and toluene, and wherein the reaction mixture of carbonyldiimidazole and the amine $R1NH_2$ is added to the compound of formula IIa* or to the compound of formula IIa within about 1 to about 4 hours and the reaction temperature is continuously increased from around 55 to around 105° C. by distilling off acetonitrile.

9. A process according to claim 3, wherein in d) the solvent is pure toluene, and wherein the reaction mixture of carbonyldiimidazole and the amine $R1NH_2$ is added to the compound of formula IIa* or to the compound of formula IIa within about 5 to about 20 hours, under an isothermal condition at an activation temperature of around 100-105° C.

10. A process according to claim 3, wherein
R1 is 2-(R11)-ethyl, or 3-(R11)-propyl,
R11 is —N(R111)R112,
R111 is methyl, ethyl, propyl, isopropyl, isobutyl, tertbutyl, allyl, propargyl, 1-methyl-propargyl, cyclopropyl, cyclobutyl, cyclopropylmethyl, 2-hydroxyethyl, 2-methoxyethyl, 2-fluoroethyl, 2,2-difluoroethyl, or 2,2,2-trifluoroethyl, and
R112 is hydrogen,
or
R111 is methyl, ethyl, propyl, isopropyl, isobutyl, tertbutyl, allyl, propargyl, 1-methyl-propargyl, cyclopropyl, cyclobutyl, cyclopropylmethyl, 2-hydroxyethyl, 2-methoxyethyl, 2-fluorethyl, 2,2-difluoroethyl, or 2,2,2-trifluoroethyl, and
R112 is methyl,
or
R111 is ethyl, propyl, isopropyl, allyl, propargyl, 1-methyl-propargyl, cyclopropyl, cyclobutyl, cyclopropylmethyl, 2-hydroxyethyl, 2-methoxyethyl, 2-fluoroethyl, 2,2,-difluoroethyl, or 2,2,2-trifluoroethyl, and
R112 is ethyl,
or
R111 and R112 together and with inclusion of the nitrogen atom, to which they are bonded, form a ring Het,
Het is piperidin-1-yl, morpholin-4-yl, pyrrolidin-1-yl, azetidin-1-yl, homopiperidin-1-yl, 4N—(R113)-piperazin-1-yl, 4N—(R113)-homopiperazin-1-yl, 2,5-dihydro-pyrrol-1-yl, 1,2,3,6-tetrahydropyridin-1-yl, 4-methyl-piperidin-1-yl, 4-fluoro-piperidin-1-yl, 4,4-difluoro-piperidin-1-yl, (S)-3-fluoro-pyrrolidin-1-yl, (R)-3-fluoro-pyrrolidin-1-yl, or 3,3,-difluoro-pyrrolidin-1-yl,
R113 is methyl or acetyl,
or
Het is pyrazol-1-yl, or imidazol-1-yl,
R2 is hydrogen,
R3 is hydrogen,
R4 is methyl,
R5 is chlorine, bromine, fluorine, ethoxy, methoxy, difluoromethoxy or trifluoromethoxy, and
R6 is hydrogen or fluorine,
wherein R5 is bonded to the 6-position, and R6 is bonded to the 5- or 7 position,
or a salt thereof.

11. A process according to claim 2 for preparing an enantiomerically pure (stereomerically pure) compound of formula Ia

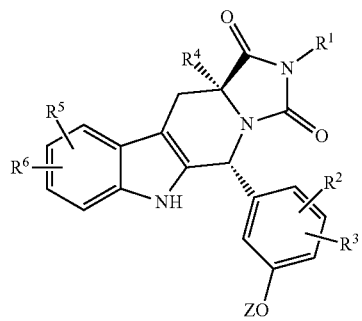

wherein
R1 is 2-7C-alkyl substituted by —N(R111)R112,
R111 is 1-4C-alkyl, 2-4C-alkenyl, 2-4C-alkinyl, 3-7C-cycloalkyl, 3-7C-cycloalkyl-1-4C-alkyl, hydroxy-2-4C-alkyl, 1-4C-alkoxy-2-4C-alkyl, 1N-(1-4C-alkyl)-pyrazolyl, 1N—(H)-pyrazolyl, isoxazolyl, or completely or partially fluorine-substituted 1-4C-alkyl,
R112 is hydrogen, 1-4C-alkyl, 3-7C-cycloalkyl, or 3-7C-cycloalkyl-1-4C-alkyl,
or
R111 and R112 together and with inclusion of the nitrogen atom, to which they are bonded, form a ring Het,
Het is piperidin-1-yl, morpholin-4-yl, thiomorpholin-4-yl, S-oxo-thiomorpholin-4-yl, S,S-dioxo-thiomorpholin-4-yl, pyrrolidin-1-yl, azetidin-1-yl, homopiperidin-1-yl, 4N—(R113)-piperazin-1-yl, 4N—(R113)-homopiperazin-1-yl, 2,5-dihydro-pyrrol-1-yl, 1,2,3,6-tetra-hydropyridin-1-yl, pyrrol-1-yl, pyrazol-1-yl, imidazol-1-yl, triazol-1-yl, or tetrazol-1-yl, wherein said Het may be optionally substituted by one or two substituents independently selected from fluorine and 1-4C-alkyl,
R113 is hydrogen, 1-4C-alkyl, 3-7C-cycloalkyl, 3-7C-cycloalkyl-1-4C-alkyl, 1-4C-alkylcarbonyl, amidino, or completely or partially fluorine-substituted 1-4C-alkyl,
R2 is hydrogen, 1-4C-alkyl, halogen trifluoromethyl, 1-4C-alkoxy or hydroxyl,
R3 is hydrogen, 1-4C-alkyl, halogen, trifluoromethyl or 1-4C-alkoxy,
R4 is 1-4C-alkyl, 3-7C-cycloalkyl or 3-7C-cycloalkyl-1-4C-alkyl,
R5 is 1-4C-alkyl, halogen, 1-4C-alkoxy, trifluoromethyl, cyano, hydroxyl, phenyl-1-4C-alkoxy, 1-4C-alkoxy-2-4C-alkoxy, hydroxy-2-4C-alkoxy, 3-7C-cycloalkoxy, 3-7C-cycloalkyl-1-4C-alkoxy, or completely or predominantly fluorine-substituted 1-4C-alkoxy,
R6 is hydrogen, 1-4C-alkyl or halogen, and
Z is a protective group, which process comprises
a) providing an enantiomerically pure (stereomerically pure) tryptophane compound of formula IVa,

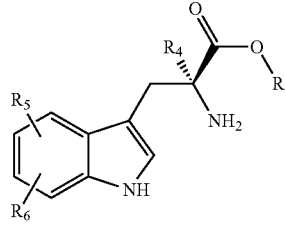

wherein R is methyl or ethyl and R4, R5, and R6 are as defined above,
b) reacting the compound of formula IVa with 3-hydroxybenzaldehyde of formula III in a Pictet Spengler Reaction,

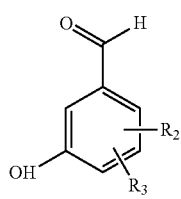

wherein R2, and R3 are as defined above,
to obtain a mixture of compounds of formulae IIa and IIb,

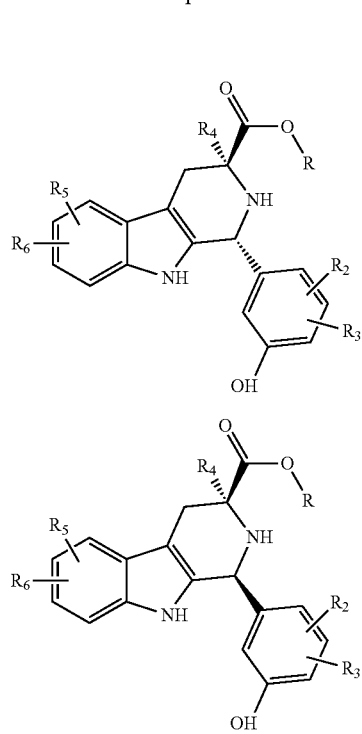

wherein R, R2, R3, R4, R5, and R6 are as defined above, and separating the compounds of formulae IIa and IIb to obtain a compound of formula IIa, c) optionally protecting the compound of formula IIa at the 3-hydroxyphenyl moiety to obtain a compound of formula IIa*,

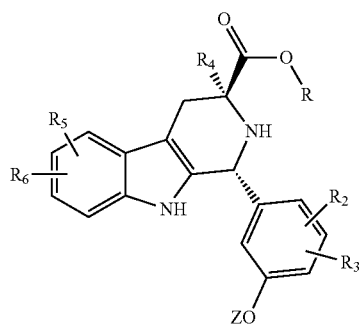

wherein R, R2, R3, R4, R5, and R6 are as defined above and Z is a protective group,
d) heterocyclizing the compound of formula IIa* or the compound of formula IIa by in situ prepared isocyanate R1-N=C=O by adding a reaction mixture of carbonyldiimidazole and an amine R1NH$_2$ in a solvent selected from the group consisting of toluene, xylene, a mixture of toluene and acetonitrile and a mixture of toluene and benzonitrile to obtain a compound of formula Ia.

12. A process according to claim 1 for preparing an enantiomerically pure (stereomerically pure) compound of formula I

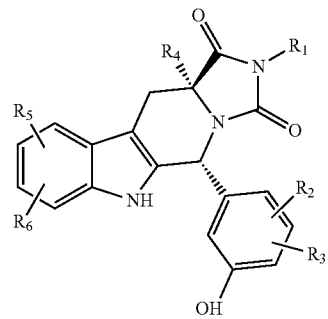

in which
R1 is 2-7C-alkyl substituted by —N(R111)R112,
R111 is 1-4C-alkyl, 2-4C-alkenyl, 2-4C-alkinyl, 3-7C-cycloalkyl, 3-7C-cycloalkyl-1-4C-alkyl, hydroxy-2-4C-alkyl, 1-4C-alkoxy-2-4C-alkyl, 1N-(1-4C-alkyl)-pyrazolyl, 1N—(H)-pyrazolyl, isoxazolyl, or completely or partially fluorine-substituted 1-4C-alkyl,
R112 is hydrogen, 1-4C-alkyl, 3-7C-cycloalkyl, or 3-7C-cycloalkyl-1-4C-alkyl,
or
R111 and R112 together and with inclusion of the nitrogen atom, to which they are bonded, form a ring Het,
Het is piperidin-1-yl, morpholin-4-yl, thiomorpholin-4-yl, S-oxo-thiomorpholin-4-yl, S,S-dioxo-thiomorpholin-4-yl, pyrrolidin-1-yl, azetidin-1-yl, homopiperidin-1-yl, 4N—(R113)-piperazin-1-yl, 4N—(R113)-homopiperazin-1-yl, 2,5-dihydro-pyrrol-1-yl, 1,2,3,6-tetra-hydropyridin-1-yl, pyrrol-1-yl, pyrazol-1-yl, imidazol-1-yl, triazol-1-yl, or tetrazol-1-yl, wherein said Het may be optionally substituted by one or two substituents independently selected from fluorine and 1-4C-alkyl, R113 is hydrogen, 1-4C-alkyl, 3-7C-cycloalkyl, 3-7C-cycloalkyl-1-4C-alkyl, 1-4C-alkylcarbonyl, amidino, or completely or partially fluorine-substituted 1-4C-alkyl, R2 is hydrogen, 1-4C-alkyl, halogen trifluoromethyl, 1-4C-alkoxy or hydroxyl, R3 is hydrogen, 1-4C-alkyl, halogen, trifluoromethyl or 1-4C-alkoxy, R4 is 1-4C-alkyl, 3-7C-cycloalkyl or 3-7C-cycloalkyl-1-4C-alkyl, R5 is 1-4C-alkyl, halogen, 1-4C-alkoxy, trifluoromethyl, cyano, hydroxyl, phenyl-1-4C-alkoxy, 1-4C-alkoxy-2-4C-alkoxy, hydroxy-2-4C-alkoxy, 3-7C-cycloalkoxy, 3-7C-cycloalkyl-1-4C-alkoxy, or completely or predominantly fluorine-substituted 1-4C-alkoxy, and R6 is hydrogen, 1-4C-alkyl or halogen, or a salt thereof which process comprises c) optionally protecting the compound of formula IIa

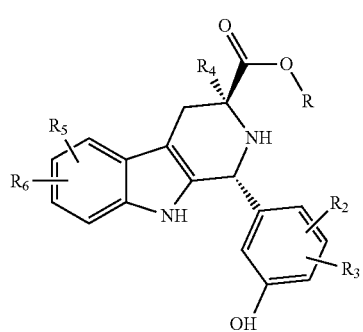

wherein R, R2, R3, R4, R5, and R6 are as defined above, at the 3-hydroxyphenyl moiety to obtain a compound of formula IIa*,

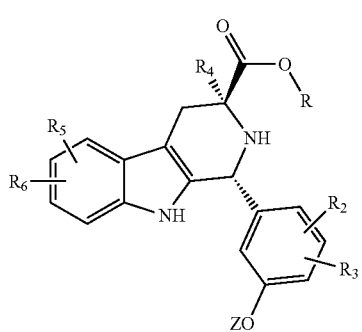

wherein R, R2, R3, R4, R5, and R6 are as defined above and Z is a protective group, d) heterocyclizing the compound of formula IIa* or the compound of formula IIa by in situ prepared isocyanate R1-N=C=O by adding a reaction mixture of carbonyldiimidazole and an amine R1NH$_2$ in a solvent selected from the group consisting of toluene, xylene, a mixture of toluene and acetonitrile and a mixture of toluene and benzonitrile to obtain a compound of formula Ia,

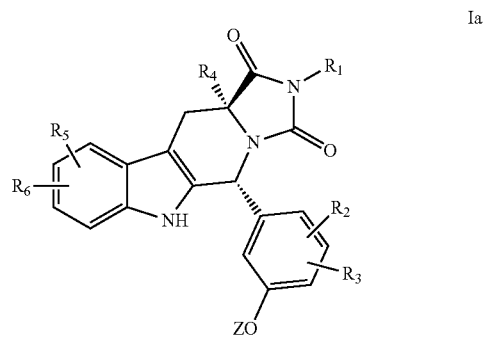

wherein R1-R6 and Z are as defined above, or to obtain the compound of formula I, e) deprotecting the 3-hydroxyphenyl moiety of the compound of formula Ia to obtain the compound of formula I, provided that the compound of formula IIa have been protected at the 3-hydroxyphenyl moiety in c), and f) optionally converting the compound of formula I into a salt thereof.

13. A process according to claim 1, wherein in d), the solvent is toluene.

14. A process according to claim 1, wherein in d), the solvent is xylene.

15. A process according to claim 1, wherein in d), the solvent is a mixture of toluene and acetonitrile.

16. A process according to claim 1, wherein in d), the solvent is a mixture of toluene and benzonitrile.

17. A process according to claim 3, wherein in d), the solvent is toluene.

18. A process according to claim 3, wherein in d), the solvent is xylene.

19. A process according to claim 3, wherein in d), the solvent is a mixture of toluene and acetonitrile.

20. A process according to claim 3, wherein in d), the solvent is a mixture of toluene and benzonitrile.

* * * * *

UNITED STATES PATENT AND TRADEMARK OFFICE
CERTIFICATE OF CORRECTION

PATENT NO.       : 8,557,991 B2
APPLICATION NO.  : 12/920990
DATED            : October 15, 2013
INVENTOR(S)      : Muller et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 362 days.

Signed and Sealed this
Fifteenth Day of September, 2015

Michelle K. Lee
*Director of the United States Patent and Trademark Office*